(12) United States Patent
Verma et al.

(10) Patent No.: US 10,940,183 B2
(45) Date of Patent: Mar. 9, 2021

(54) ALBUMIN-BASED NON-COVALENT COMPLEXES AND METHODS OF USE THEREOF

(71) Applicant: Spectral Platforms, Inc., Monrovia, CA (US)

(72) Inventors: Ravi Verma, Monrovia, CA (US); Changjun Yu, Pasadena, CA (US)

(73) Assignee: Spectral Platforms, Inc., Monrovia, CA (US)

(*) Notice: Subject to any disclaimer, the term of this patent is extended or adjusted under 35 U.S.C. 154(b) by 0 days.

(21) Appl. No.: 16/422,704

(22) Filed: May 24, 2019

(65) Prior Publication Data

US 2020/0121763 A1 Apr. 23, 2020

Related U.S. Application Data

(62) Division of application No. 16/056,366, filed on Aug. 6, 2018, now Pat. No. 10,342,855, which is a division of application No. 15/148,587, filed on May 6, 2016, now Pat. No. 10,071,141.

(60) Provisional application No. 62/158,670, filed on May 8, 2015, provisional application No. 62/294,931, filed on Feb. 12, 2016.

(51) Int. Cl.
| | |
|---|---|
| *A01N 43/90* | (2006.01) |
| *A61K 38/38* | (2006.01) |
| *A61K 9/00* | (2006.01) |
| *C12Q 1/04* | (2006.01) |

(52) U.S. Cl.
CPC ............ *A61K 38/385* (2013.01); *A01N 43/90* (2013.01); *A61K 9/00* (2013.01); *C12Q 1/04* (2013.01)

(58) Field of Classification Search
CPC ........ A61K 38/385; A61K 9/00; A01N 43/90; C12Q 1/04
See application file for complete search history.

(56) References Cited

U.S. PATENT DOCUMENTS

| | | | |
|---|---|---|---|
| 4,187,285 A | 2/1980 | Meeks et al. | |
| 4,226,846 A | 10/1980 | Saklad | |
| 5,134,126 A * | 7/1992 | Rodriguez | |
| 5,916,596 A | 6/1999 | Desai et al. | |
| 2004/0014655 A1 | 1/2004 | Hegedus et al. | |
| 2005/0004011 A1 | 1/2005 | Cavaleri et al. | |
| 2005/0009788 A1 | 1/2005 | Lockwood et al. | |
| 2005/0064028 A1 | 3/2005 | Hegedus et al. | |
| 2005/0075337 A1 | 4/2005 | Lockwood et al. | |
| 2005/0089901 A1 | 4/2005 | Porter et al. | |
| 2007/0232536 A1 | 10/2007 | Hegedus et al. | |
| 2008/0220989 A1 | 9/2008 | Tseng et al. | |
| 2010/0143883 A1 | 6/2010 | Wilson et al. | |
| 2013/0052636 A1 | 2/2013 | Verma et al. | |
| 2014/0081133 A1 | 3/2014 | Nie et al. | |
| 2015/0309040 A1 | 10/2015 | Chang et al. | |
| 2016/0299135 A1 | 10/2016 | Cameron et al. | |
| 2016/0324933 A1 | 11/2016 | Verma et al. | |

FOREIGN PATENT DOCUMENTS

| | | |
|---|---|---|
| EP | 0326618 | 8/1989 |
| EP | 1711823 | 10/2006 |
| EP | 2359859 | 8/2011 |
| JP | S63297664 | 12/1988 |
| WO | WO 1998014174 | 4/1998 |
| WO | WO 1999013914 | 3/1999 |
| WO | WO 2003106699 | 12/2003 |
| WO | WO 2004011423 | 2/2004 |
| WO | WO 2005066612 | 7/2005 |
| WO | WO 2007078635 | 7/2007 |
| WO | WO 2009018544 | 2/2009 |

OTHER PUBLICATIONS

Baron (Medical Microbiology 4th edition, Galveston TX, University of Texas Medical Branch at Galveston, Chapter 6, 1996, pp. 1-10) (Year: 1996).*
BioNavis Ltd.; "Interactions of small molecular weight drugs with human serum albumin"; Application Note # 121. 2 pages; downloaded off the web Jun. 17, 2015.
Fasano Mauro, et al; (2005) The Extraordinary Ligand Binding Properties of Human Serum Albumin; IUBMB Life. 57(12): pp. 787-796.
Gülseren Ibrahim, et al; (2007) "Structural and functional changes in ultrasonicated bovine serum albumin solutions"; Ultrasonics Sonochemistry 14; pp. 173-183.
Hoskins (1984) "Resonance Raman Spectroscopy of β-Carotene and lycopene"; Journal of Chemical Education 61, No. 5; pp. 460-462.
Khana Salman, et al (2015) "Improved efficiency and stability of secnidazole—An ideal delivery system"; Saudi J Biol Sci.22(1); pp. 42-49.
López-Ramírez, et al (2010) "Trans—cis isomerisation of the carotenoid lycopene upon complexation with cholesteric polyester carriers investigated by Raman spectroscopy and density functional theory"; Journal of Raman Spectroscopy; pp. 1170-1177.
Merlin, Jean Claude (1985) "Resonance Raman spectroscopy of carotenoids and carotenoid-containing systems"; Pure and Applied Chemistry 57(5); pp. 785-792.
Militello, Valeria, et al (2004) "Aggregation kinetics of bovine serum albumin studied by FTIR spectroscopy and light scattering"; Biophysical Chemistry 107; pp. 175-187.

(Continued)

*Primary Examiner* — Alma Pipic
(74) *Attorney, Agent, or Firm* — Khin K. Chin; Bozicevic, Field & Francis LLP

(57) ABSTRACT

A non-covalent complex of an albumin molecule and a hydrophobic ligand, compositions containing the same, and methods of use thereof are provided. The present complex may find use in delivering the hydrophobic ligand to microorganisms that have albumin-binding outer surfaces, such as a cell wall.

14 Claims, 27 Drawing Sheets

Specification includes a Sequence Listing.

(56) References Cited

OTHER PUBLICATIONS

Paál, Krisztina, et al; (2001) "High affinity binding of paclitaxel to human serum albumin"; Eur. J. Biochem. 268; pp. 2187-2191.

Rehman and Khan (2015) "Understanding the interaction between human serum albumin and anti-bacterial/ anti-cancer compounds"; Curr Pharm Des. 21(14); pp. 1785-1799.

Rodríguez, Galdón B, et al; (2013) "Spectroscopic study of the interaction between lycopene and bovine serum albumin"; Luminescence. 28(5); pp. 765-770.

Sivertsen, Annfrid, et al; (2014) "Synthetic cationic antimicrobial peptides bind with their hydrophobic parts to drug site II of human serum albumin"; BMC Struct Biol. 14/4; doi: 10.1186/1472-6807-14/4; pp. 1-14.

Tang K, et al; (2005) "Interaction of daunomycin antibiotic with human serum albumin. investigation by resonant mirror biosensor technique, fluorescence spectroscopy and molecular modeling methods"; J Pharm Biomed Anal. 39(3-4); pp. 404-410.

Varshney A, et al; (2010) "Ligand binding strategies of human serum albumin: how can the cargo be utilized?"; Chirality. 22(1); pp. 77-87.

Wang, Rongsheng E, et al; (2012) "A Homogeneous Fluorescent Sensor for Human Serum Albumin"; J Pharm Biomed Anal. 63; pp. 165-169.

Yang F, et al; (2014) "Interactive association of drugs binding to human serum albumin"; Int J Mol Sci. 15(3); pp. 3580-3595.

Zhong Dongping, et al; (2000) "Femtosecond studies of protein-ligand hydrophobic binding and dynamics. human serum albumin"; Proc Natl Acad Sci U S A. 97(26); pp. 14056-14061.

Henmi, et al (1989) "Astaxanthin and/or Canthaxanthin-actomyosin Complex in Salmon Muscle"; *Nippon Suisan Gakkaishi* 55(9); pp. 1583-1589.

Jehlička, et al (2014) "Potential and Limits of Raman Spectroscopy for Carotenoid Detection in Microorganisms: Implications for Astrobiology"; *Philos Trans of Royal Soc. A Math Phys Eng Sci*, 372 (2030); pp. 1-17.

Li, et al (2015) "β-Carotene and Astaxanthin With Human and Bovine Serum Albumins"; Food Chem 179; pp. 213-221.

Partali et al. (1985) "Carotenoids in food chain studies—I. Zooplankton (*Daphnia magna*) response to a unialgal (*Scenedesmus acutus*) carotenoid diet, to spinach, and to yeast diets supplemented with individual carotenoids"; Comparative Biochemistry and Physiology, Part B: Biochemistry & Molecular Bioi. 82B(4): pp. 767-772.

\* cited by examiner

Figure 25

NCBI Reference Sequence: NP_000468.1 (SEQ ID NO:1)

```
1   mkwvtfisll flfssaysrg vfrrdahkse vahrfkdlge enfkalvlia faqylqqcpf
61  edhvklvnev tefaktcvad esaencdksl htlfgdklct vatlretyge madccakqep
121 ernecflqhk ddnpnlprlv rpevdvmcta fhdneetflk kylyeiarrh pyfyapellf
181 fakrykaaft eccqaadkaa cllpkldelr degkassakq rlkcaslqkf gerafkawav
241 arlsqrfpka efaevsklvt dltkvhtecc hgdllecadd radlakyice nqdsisslk
301 eccekpllek shciaevend empadlpsla adfveskdvc knyaeakdvf lgmflyeyar
361 rhpdysvvll lrlaktyett lekccaaadp hecyakvfde fkplveepqn likqncelfe
421 qlgeykfqna llvrytkkvp qvstptlvev srnlgkvgsk cckhpeakrm pcaedylsvv
481 lnqlcvlhek tpvsdrvtkc cteslvnrrp cfsalevdet yvpkefnaet ftfhadictl
541 sekerqikkq talvelvkhk pkatkeqlka vmddfaafve kccaddket cfaeegkklv
601 aasqaalgl
```

Figure 26

NCBI Reference Sequence: NP_851335.1 (SEQ ID NO:2)

```
1   mkwvtfisll llfssaysrg vfrrdthkse iahrfkdlge ehfkglvlia fsqylqqcpf
61  dehvklvnel tefaktcvad eshagceksl htlfgdelck vaslretygd madccekqep
121 ernecflshk ddspdlpklk pdpntlcdef kadekkfwgk ylyeiarrhp yfyapellyy
181 ankyngvfqe ccqaedkgac llpkietmre kvltssarqr lrcasiqkfg eralkawsva
241 rlsqkfpkae fvevtklvtd ltkvhkecch gdllecaddr adlakyicdn qdtisssklke
301 ccdkplleks hciaevekda ipenlpplta dfaedkdvck nyqeakdafl gsflyeysrr
361 hpeyavsvll rlakeyeatl eeccakddph acystvfdkl khlvdepqnl ikqncdqfek
421 lgeygfqnal ivrytrkvpq vstptlvevs rslgkvgtrc ctkpesermp ctedylslil
481 nrlcvlhekt pvsekvtkcc teslvnrrpc fsaltpdety vpkafdeklf tfhadictlp
541 dtekqikkqt alvellkhkp kateeqlktv menfvafvdk ccaaddkeac favegpklvv
601 stqtala
```

Figure 27

NCBI Reference Sequence: NP_033784.2 (SEQ ID NO:3)

```
1   mkwvtfllll fvsgsafsrg vfrreahkse iahryndlge qhfkglvlia fsqylqkcsy
61  dehaklvqev tdfaktcvad esaancdksl htlfgdklca ipnlrenyge ladcctkqep
121 ernecflqhk ddnpslppfe rpeaeamcts fkenpttfmg hylhevarrh pyfyapelly
181 yaeqyneilt qccaeadkes cltpkldgvk ekalvssvrq rmkcssmqkf gerafkawav
241 arlsqtfpna dfaeitklat dltkvnkecc hgdllecadd raelakymce nqatissklq
301 tccdkpllkk ahclsevehd tmpadlpaia adfvedqevc knyaeakdvf lgtflyeysr
361 rhpdysvsll lrlakkyeat lekccaeanp pacygtvlae fqplveepkn lvktncdlye
421 klgeygfqna ilvrytqkap qvstptlvea arnlgrvgtk cctlpedqrl pcvedylsai
481 lnrvcllhek tpvsehvtkc csgslverrp cfsaltvdet yvpkefkaet ftfhsdictl
541 pekekqikkq talaelvkhk pkataeqlkt vmddfaqfld tcckaaddkdt cfstegpnlv
601 trckdala
```

Figure 28
NCBI Reference Sequence: NP_599153.2 (SEQ ID NO:4)

```
1   mkwvtfllll fisgsafsrg vfrreahkse iahrfkdlge qhfkglvlia fsqylqkcpy
61  eehiklvqev tdfaktcvad enaencdksi htlfgdklca ipklrdnyge ladccakqep
121 ernecflqhk ddnpnlppfq rpeaeamcts fqenptsflg hylhevarrh pyfyapelly
181 yaekynevlt qcctesdkaa cltpkldavk ekalvaavrq rmkcssmqrf gerafkawav
241 armsqrfpna efaeitklat dltkinkecc hgdllecadd raelakymce nqatissklq
301 accdkpvlqk sqclaeiehd nipadlpsia adfvedkevc knyaeakdvf lgtflyeysr
361 rhpdysvsll lrlakkyeat lekccaegdp pacygtvlae fqplveepkn lvktncelye
421 klgeygfqna ilvrytqkap qvstptlvea arnlgrvgtk cctlpeaqrl pcvedylsai
481 lnrlcvlhek tpvsekvtkc csgslverrp cfsaltvdet yvpkefkaet ftfhsdictl
541 pdkekqikkq talaelvkhk pkatedqlkt vmgdfaqfvd kcckaadkdn cfategpnlv
601 arskeala
```

Figure 29
NCBI Reference Sequence: XP_005681801.1 (SEQ ID NO:5)

```
1   mkwvtfisll llfssaysrg vfrrdthkse iahrfndlge enfqglvlia fsqylqqcpf
61  dehvklvkel tefaktcvad eshagcdksl htlfgdelck vatlretygd madccekqep
121 ernecflkhk ddspdlpklk pepdtlcaef kadekkfwgk ylyevarrhp yfyapellyy
181 ankyngvfqe ccqaedkgac llpkietmre kvlassarqr lrcasiqkfg eralkawsva
241 rlsqkfpkad ftdvtkivtd ltkvhkecch gdllecaddr adlakyicdh qdtlssklke
301 ccdkpvleks hciaeidkda vpenlpplta dfaedkevck nyqeakdvfl gsflyeysrr
361 hpeyavsvll rlakeyeatl edccakedph acyatvfdkl khlvdepqnl ikkncelfek
421 hgeygfqnal ivrytrkapq vstptlveis rslgkvgtkc cakpesermp ctedylslil
481 nrlcvlhekt pvsekvtkcc teslvnrrpc fsdltldety vpkpfdgesf tfhadictlp
541 dtekqikkqt alvellkhkp katdeqlktv menfvafvdk ccaaddkegc fllegpklva
601 stqaala
```

Figure 30
NCBI Reference Sequence: NP_001310707.1 (SEQ ID NO:6)

```
1   mkwvtfvsll flfssayfrg vlrrdthkse iahrfndlge khfkglvlva fsqylqqcpf
61  edhvklvnev tefakkcaad esaencdksl htlfgdklct vatlratyge ladccekqep
121 ernecflthk ddhpnlpklk pepdaqcaaf qedpdkflgk ylyevarrhp yfygpellfh
181 aeeykadfte ccpaddkagc lipkldalke rillssaker lkcssfqkfg erafkawsva
241 rlsqkfpkad faevskivtd ltkvhkecch gdllecaddr adltkyiceh qdsisgklka
301 ccdkpllqks hciaevkedd lpsdlpalaa dfaedkeick hykdakdvfl gtflyeysrr
361 hpdysvslll riaktyeatl ekccaeadpp acyatvfdqf tplveepksl vkkncdlfee
421 vgeydfqnal ivrytkkapq vstptlveig rtlgkvgsrc cklpeserlp csenhlalal
481 nrlcvlhekt pvsekitkcc tdslaerrpc fsaleldegy ipkefkaetf tfhadictlp
541 edekqikkqs alaelvkhkp katkeqlktv lgnfsafvak ccgaedkeac faeegpklva
601 ssqlala
```

Figure 31
NCBI Reference Sequence: NP_001075972.1 (SEQ ID NO:7)
```
1   mkwvtfvsll flfssaysrg vlrrdthkse iahrfndlge khfkglvlva fsqylqqcpf
61  edhvklvnev tefakkcaad esaencdksl htlfgdklct vatlratyge ladccekqep
121 ernecflthk ddhpnlpklk pepdaqcaaf qedpdkflgk ylyevarrhp yfygpellfh
181 aeeykadfte ccpaddklac lipkldalke rillssaker lkcssfqnfg eravkawsva
241 rlsqkfpkad faevskivtd ltkvhkecch gdllecaddr adlakyiceh qdsisgklka
301 ccdkpllqks hciaevkedd lpsdlpalaa dfaedkeick hykdakdvfl gtflyeysrr
361 hpdysvslll riaktyeatl ekccaeadpp acyrtvfdqf tplveepksl vkkncdlfee
421 vgeydfqnal ivrytkkapq vstptlveig rtlgkvgsrc cklpeserlp csenhlalal
481 nrlcvlhekt pvsekitkcc tdslaerrpc fsaleldegy vpkefkaetf tfhadictlp
541 edekqikkqs alaelvkhkp katkeqlktv lgnfsafvak ccgredkeac faeegpklva
601 ssqlala
```

Figure 32
NCBI Reference Sequence: XP_010967650.1 (SEQ ID NO:8)
```
1   mkwvtfisll flfssvysrg vfrrdthkse iahrfkdlge ddfkglvlia fsqylqqcpf
61  ddhvklvnev tefaktcvad esaadcdksl htlfgdklct vaslretyge madccekqep
121 ernecflqhk sdnpdlpklk pepealctaf qenekrfggk ylyeiarrhp yfapellyy
181 ahqykhvfee cckdadkaac llpkldalke rilassarqr lrctsiqkfg dralkawsvg
241 hlsqkfpkad faeiskivtd ltkihkeccq gdllecaddr adlakyfcdn qetissklke
301 ccekplleks hciheaerde mpenlpaite qfaedkdvck hyteekdvfl gmflheyarr
361 hpeyavslll riakeyeatl edccakddph acyatvfdkl qhladepqnl vkqncelfek
421 lgeygfqndi lvrytkrlpq vstptlveva rglgrvgtkc ctlpesnrms caedylslil
481 nrlcvlhekt pvsprvtkcc teslvnrrpc fssltadety epkefdektf tfhadlcsvs
541 epekqikkqt alaellkhkp katdeqlktv mekfvafvdk ccaavdkeac ftvegpllva
601 atrtala
```

Figure 33
NCBI Reference Sequence: XP_010981066.1 (SEQ ID NO:9)
```
1   mkwvtfisll flfssvysrg vfrrdthkse iahrfkdlge ddfkglvlia fsqylqqcpf
61  ddhvklvnev tefaktcvad esaadcdksl htlfgdklct vaslretyge madccekqep
121 ernecflqhk sdnpdlpklk pepealctaf qenekrfggk ylyeiarrhp yfapellyy
181 ahqykhvfee cckdadkaac llpkldalke rilassarqr lrctsiqkfg dralkawsvg
241 hlsqkfpkad faeiskivtd ltkihkeccq gdllecaddr adlakyfcdn qetissklke
301 ccekplleks hciheaerde mpenlpaite qfaedkdvck hyteekdvfl gmflheyarr
361 hpeyavslll riakeyeatl edccakddph acyatvfdkl qhladepqnl vkqncelfek
421 lgeygfqndi lvrytkrlpq vstptlveva rglgrvgtkc ctlpesnrms caedylslil
481 nrlcvlhekt pvsprvtkcc teslvnrrpc fssltadety epkefdektf tfhadlcsvs
541 epekqikkqt alaellkhkp katdeqlktv mekfvafvdk ccaavdkeac ftvegpllva
601 atrtala
```

US 10,940,183 B2

SEQUENCE LISTING

```
<160> NUMBER OF SEQ ID NOS: 9

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110
```

```
Asp Cys Cys Ala Lys Gln Glu Pro Glu Arg Asn Glu Cys Phe Leu Gln
    115                 120                 125
His Lys Asp Asp Asn Pro Asn Leu Pro Arg Leu Val Arg Pro Glu Val
130                 135                 140
Asp Val Met Cys Thr Ala Phe His Asp Asn Glu Glu Thr Phe Leu Lys
145                 150                 155                 160
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
                180                 185                 190
Cys Gln Ala Ala Asp Lys Ala Ala Cys Leu Leu Pro Lys Leu Asp Glu
        195                 200                 205
Leu Arg Asp Glu Gly Lys Ala Ser Ser Ala Lys Gln Arg Leu Lys Cys
        210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
                260                 265                 270
Asp Leu Leu Glu Cys Ala Asp Asp Arg Ala Asp Leu Ala Lys Tyr Ile
            275                 280                 285
Cys Glu Asn Gln Asp Ser Ile Ser Ser Lys Leu Lys Glu Cys Cys Glu
        290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
                340                 345                 350
Met Phe Leu Tyr Glu Tyr Ala Arg Arg His Pro Asp Tyr Ser Val Val
            355                 360                 365
Leu Leu Leu Arg Leu Ala Lys Thr Tyr Glu Thr Thr Leu Glu Lys Cys
        370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
                420                 425                 430
Val Arg Tyr Thr Lys Lys Val Pro Gln Val Ser Thr Pro Thr Leu Val
            435                 440                 445
Glu Val Ser Arg Asn Leu Gly Lys Val Gly Ser Lys Cys Cys Lys His
        450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
            500                 505                 510
Ser Ala Leu Glu Val Asp Glu Thr Tyr Val Pro Lys Glu Phe Asn Ala
        515                 520                 525
```

```
Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu

<210> SEQ ID NO 2
<211> LENGTH: 607
<212> TYPE: PRT
<213> ORGANISM: Bos taurus

<400> SEQUENCE: 2

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
                20                  25                  30

His Arg Phe Lys Asp Leu Gly Glu Glu His Phe Lys Gly Leu Val Leu
            35                  40                  45

Ile Ala Phe Ser Gln Tyr Leu Gln Gln Cys Pro Phe Asp Glu His Val
        50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Thr Ser Ser Ala Arg Gln Arg Leu Arg Cys Ala
210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285
```

```
Asp Asn Gln Asp Thr Ile Ser Ser Lys Leu Lys Glu Cys Cys Asp Lys
    290                 295                 300
Pro Leu Glu Lys Ser His Cys Ile Ala Glu Val Glu Lys Asp Ala
305                 310                 315                 320
Ile Pro Glu Asn Leu Pro Pro Leu Thr Ala Asp Phe Ala Glu Asp Lys
                325                 330                 335
Asp Val Cys Lys Asn Tyr Gln Glu Ala Lys Asp Ala Phe Leu Gly Ser
            340                 345                 350
Phe Leu Tyr Glu Tyr Ser Arg Arg His Pro Glu Tyr Ala Val Ser Val
        355                 360                 365
Leu Leu Arg Leu Ala Lys Glu Tyr Glu Ala Thr Leu Glu Glu Cys Cys
370                 375                 380
Ala Lys Asp Asp Pro His Ala Cys Tyr Ser Thr Val Phe Asp Lys Leu
385                 390                 395                 400
Lys His Leu Val Asp Glu Pro Gln Asn Leu Ile Lys Gln Asn Cys Asp
                405                 410                 415
Gln Phe Glu Lys Leu Gly Glu Tyr Gly Phe Gln Asn Ala Leu Ile Val
            420                 425                 430
Arg Tyr Thr Arg Lys Val Pro Gln Val Ser Thr Pro Thr Leu Val Glu
        435                 440                 445
Val Ser Arg Ser Leu Gly Lys Val Gly Thr Arg Cys Cys Thr Lys Pro
450                 455                 460
Glu Ser Glu Arg Met Pro Cys Thr Glu Asp Tyr Leu Ser Leu Ile Leu
465                 470                 475                 480
Asn Arg Leu Cys Val Leu His Glu Lys Thr Pro Val Ser Glu Lys Val
                485                 490                 495
Thr Lys Cys Cys Thr Glu Ser Leu Val Asn Arg Arg Pro Cys Phe Ser
            500                 505                 510
Ala Leu Thr Pro Asp Glu Thr Tyr Val Pro Lys Ala Phe Asp Glu Lys
        515                 520                 525
Leu Phe Thr Phe His Ala Asp Ile Cys Thr Leu Pro Asp Thr Glu Lys
530                 535                 540
Gln Ile Lys Lys Gln Thr Ala Leu Val Glu Leu Leu Lys His Lys Pro
545                 550                 555                 560
Lys Ala Thr Glu Glu Gln Leu Lys Thr Val Met Glu Asn Phe Val Ala
                565                 570                 575
Phe Val Asp Lys Cys Cys Ala Ala Asp Asp Lys Glu Ala Cys Phe Ala
            580                 585                 590
Val Glu Gly Pro Lys Leu Val Val Ser Thr Gln Thr Ala Leu Ala
        595                 600                 605

<210> SEQ ID NO 3
<211> LENGTH: 608
<212> TYPE: PRT
<213> ORGANISM: Mus musculus

<400> SEQUENCE: 3

Met Lys Trp Val Thr Phe Leu Leu Leu Leu Phe Val Ser Gly Ser Ala
1               5                   10                  15
Phe Ser Arg Gly Val Phe Arg Arg Glu Ala His Lys Ser Glu Ile Ala
            20                  25                  30
His Arg Tyr Asn Asp Leu Gly Glu Gln His Phe Lys Gly Leu Val Leu
        35                  40                  45
Ile Ala Phe Ser Gln Tyr Leu Gln Lys Cys Ser Tyr Asp Glu His Ala
    50                  55                  60
```

```
Lys Leu Val Gln Glu Val Thr Asp Phe Ala Lys Thr Cys Val Ala Asp
 65                  70                  75                  80

Glu Ser Ala Ala Asn Cys Asp Lys Ser Leu His Thr Leu Phe Gly Asp
                 85                  90                  95

Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
        115                 120                 125

His Lys Asp Asp Asn Pro Ser Leu Pro Pro Phe Glu Arg Pro Glu Ala
    130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
        195                 200                 205

Val Lys Glu Lys Ala Leu Val Ser Ser Val Arg Gln Arg Met Lys Cys
    210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
                245                 250                 255

Lys Leu Ala Thr Asp Leu Thr Lys Val Asn Lys Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Thr Ile Ser Ser Lys Leu Gln Thr Cys Cys Asp
    290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
                325                 330                 335

Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
    370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Asp Leu Tyr Glu Lys Leu Gly Glu Tyr Gly Phe Gln Asn Ala Ile Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
    450                 455                 460

Pro Glu Asp Gln Arg Leu Pro Cys Val Glu Asp Tyr Leu Ser Ala Ile
465                 470                 475                 480
```

```
Leu Asn Arg Val Cys Leu Leu His Glu Lys Thr Pro Val Ser Glu His
            485                 490                 495

Val Thr Lys Cys Cys Ser Gly Ser Leu Val Glu Arg Arg Pro Cys Phe
        500                 505                 510

Ser Ala Leu Thr Val Asp Glu Thr Tyr Val Pro Lys Glu Phe Lys Ala
            515                 520                 525

Glu Thr Phe Thr Phe His Ser Asp Ile Cys Thr Leu Pro Glu Lys Glu
        530                 535                 540

Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
            565                 570                 575

Gln Phe Leu Asp Thr Cys Cys Lys Ala Ala Asp Lys Asp Thr Cys Phe
        580                 585                 590

Ser Thr Glu Gly Pro Asn Leu Val Thr Arg Cys Lys Asp Ala Leu Ala
            595                 600                 605

<210> SEQ ID NO 4
<211> LENGTH: 608
<212> TYPE: PRT
<213> ORGANISM: Rattus norvegicus

<400> SEQUENCE: 4

Met Lys Trp Val Thr Phe Leu Leu Leu Phe Ile Ser Gly Ser Ala
1               5                   10                  15

Phe Ser Arg Gly Val Phe Arg Arg Glu Ala His Lys Ser Glu Ile Ala
            20                  25                  30

His Arg Phe Lys Asp Leu Gly Glu Gln His Phe Lys Gly Leu Val Leu
        35                  40                  45

Ile Ala Phe Ser Gln Tyr Leu Gln Lys Cys Pro Tyr Glu Glu His Ile
    50                  55                  60

Lys Leu Val Gln Glu Val Thr Asp Phe Ala Lys Thr Cys Val Ala Asp
65                  70                  75                  80

Glu Asn Ala Glu Asn Cys Asp Lys Ser Ile His Thr Leu Phe Gly Asp
                85                  90                  95

Lys Leu Cys Ala Ile Pro Lys Leu Arg Asp Asn Tyr Gly Glu Leu Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Pro Phe Gln Arg Pro Glu Ala
    130                 135                 140

Glu Ala Met Cys Thr Ser Phe Gln Glu Asn Pro Thr Ser Phe Leu Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Asn Glu Val Leu Thr Gln Cys
            180                 185                 190

Cys Thr Glu Ser Asp Lys Ala Ala Cys Leu Thr Pro Lys Leu Asp Ala
        195                 200                 205

Val Lys Glu Lys Ala Leu Val Ala Ala Val Arg Gln Arg Met Lys Cys
    210                 215                 220

Ser Ser Met Gln Arg Phe Gly Glu Arg Ala Lys Ala Trp Ala Val
225                 230                 235                 240

Ala Arg Met Ser Gln Arg Phe Pro Asn Ala Glu Phe Ala Glu Ile Thr
                245                 250                 255
```

```
Lys Leu Ala Thr Asp Leu Thr Lys Ile Asn Lys Glu Cys Cys His Gly
            260                 265                 270

Asp Leu Leu Glu Cys Ala Asp Arg Ala Glu Leu Ala Lys Tyr Met
        275                 280                 285

Cys Glu Asn Gln Ala Thr Ile Ser Ser Lys Leu Gln Ala Cys Cys Asp
        290                 295                 300

Lys Pro Val Leu Gln Lys Ser Gln Cys Leu Ala Glu Ile Glu His Asp
305                 310                 315                 320

Asn Ile Pro Ala Asp Leu Pro Ser Ile Ala Ala Asp Phe Val Glu Asp
                325                 330                 335

Lys Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
    370                 375                 380

Cys Ala Glu Gly Asp Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Glu Leu Tyr Glu Lys Leu Gly Glu Tyr Gly Phe Gln Asn Ala Ile Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
    450                 455                 460

Pro Glu Ala Gln Arg Leu Pro Cys Val Glu Asp Tyr Leu Ser Ala Ile
465                 470                 475                 480

Leu Asn Arg Leu Cys Val Leu His Glu Lys Thr Pro Val Ser Glu Lys
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Asp Lys Glu
    530                 535                 540

Lys Gln Ile Lys Lys Gln Thr Ala Leu Ala Glu Leu Val Lys His Lys
545                 550                 555                 560

Pro Lys Ala Thr Glu Asp Gln Leu Lys Thr Val Met Gly Asp Phe Ala
                565                 570                 575

Gln Phe Val Asp Lys Cys Cys Lys Ala Ala Asp Lys Asp Asn Cys Phe
            580                 585                 590

Ala Thr Glu Gly Pro Asn Leu Val Ala Arg Ser Lys Glu Ala Leu Ala
        595                 600                 605

<210> SEQ ID NO 5
<211> LENGTH: 607
<212> TYPE: PRT
<213> ORGANISM: Capra hircus

<400> SEQUENCE: 5

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
```

```
            20                  25                  30
His Arg Phe Asn Asp Leu Gly Glu Glu Asn Phe Gln Gly Leu Val Leu
                35                  40                  45

Ile Ala Phe Ser Gln Tyr Leu Gln Gln Cys Pro Phe Asp Glu His Val
 50                  55                  60

Lys Leu Val Lys Glu Leu Thr Glu Phe Ala Lys Thr Cys Val Ala Asp
 65                  70                  75                  80

Glu Ser His Ala Gly Cys Asp Lys Ser Leu His Thr Leu Phe Gly Asp
                 85                  90                  95

Glu Leu Cys Lys Val Ala Thr Leu Arg Glu Thr Tyr Gly Asp Met Ala
                100                 105                 110

Asp Cys Cys Glu Lys Gln Glu Pro Glu Arg Asn Glu Cys Phe Leu Lys
                115                 120                 125

His Lys Asp Asp Ser Pro Asp Leu Pro Lys Leu Lys Pro Glu Pro Asp
            130                 135                 140

Thr Leu Cys Ala Glu Phe Lys Ala Asp Glu Lys Lys Phe Trp Gly Lys
145                 150                 155                 160

Tyr Leu Tyr Glu Val Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
                180                 185                 190

Gln Ala Glu Asp Lys Gly Ala Cys Leu Leu Pro Lys Ile Glu Thr Met
            195                 200                 205

Arg Glu Lys Val Leu Ala Ser Ser Ala Arg Gln Arg Leu Arg Cys Ala
            210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Asp Phe Thr Asp Val Thr Lys
                245                 250                 255

Ile Val Thr Asp Leu Thr Lys Val His Lys Glu Cys Cys His Gly Asp
                260                 265                 270

Leu Leu Glu Cys Ala Asp Asp Arg Ala Asp Leu Ala Lys Tyr Ile Cys
            275                 280                 285

Asp His Gln Asp Thr Leu Ser Ser Lys Leu Lys Glu Cys Cys Asp Lys
            290                 295                 300

Pro Val Leu Glu Lys Ser His Cys Ile Ala Glu Ile Asp Lys Asp Ala
305                 310                 315                 320

Val Pro Glu Asn Leu Pro Pro Leu Thr Ala Asp Phe Ala Glu Asp Lys
                325                 330                 335

Glu Val Cys Lys Asn Tyr Gln Glu Ala Lys Asp Val Phe Leu Gly Ser
                340                 345                 350

Phe Leu Tyr Glu Tyr Ser Arg Arg His Pro Glu Tyr Ala Val Ser Val
            355                 360                 365

Leu Leu Arg Leu Ala Lys Glu Tyr Glu Ala Thr Leu Glu Asp Cys Cys
            370                 375                 380

Ala Lys Glu Asp Pro His Ala Cys Tyr Ala Thr Val Phe Asp Lys Leu
385                 390                 395                 400

Lys His Leu Val Asp Glu Pro Gln Asn Leu Ile Lys Lys Asn Cys Glu
                405                 410                 415

Leu Phe Glu Lys His Gly Glu Tyr Gly Phe Gln Asn Ala Leu Ile Val
            420                 425                 430

Arg Tyr Thr Arg Lys Ala Pro Gln Val Ser Thr Pro Thr Leu Val Glu
            435                 440                 445
```

Ile Ser Arg Ser Leu Gly Lys Val Gly Thr Lys Cys Cys Ala Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
            485                 490                 495

Thr Lys Cys Cys Thr Glu Ser Leu Val Asn Arg Arg Pro Cys Phe Ser
            500                 505                 510

Asp Leu Thr Leu Asp Glu Thr Tyr Val Pro Lys Pro Phe Asp Gly Glu
            515                 520                 525

Ser Phe Thr Phe His Ala Asp Ile Cys Thr Leu Pro Asp Thr Glu Lys
            530                 535                 540

Gln Ile Lys Lys Gln Thr Ala Leu Val Glu Leu Leu Lys His Lys Pro
545                 550                 555                 560

Lys Ala Thr Asp Glu Gln Leu Lys Thr Val Met Glu Asn Phe Val Ala
                565                 570                 575

Phe Val Asp Lys Cys Cys Ala Ala Asp Lys Glu Gly Cys Phe Leu
                580                 585                 590

Leu Glu Gly Pro Lys Leu Val Ala Ser Thr Gln Ala Ala Leu Ala
                595                 600                 605

<210> SEQ ID NO 6
<211> LENGTH: 607
<212> TYPE: PRT
<213> ORGANISM: Equus asinus

<400> SEQUENCE: 6

Met Lys Trp Val Thr Phe Val Ser Leu Leu Phe Leu Phe Ser Ser Ala
1               5                   10                  15

Tyr Phe Arg Gly Val Leu Arg Arg Asp Thr His Lys Ser Glu Ile Ala
                20                  25                  30

His Arg Phe Asn Asp Leu Gly Glu Lys His Phe Lys Gly Leu Val Leu
            35                  40                  45

Val Ala Phe Ser Gln Tyr Leu Gln Gln Cys Pro Phe Glu Asp His Val
50                  55                  60

Lys Leu Val Asn Glu Val Thr Glu Phe Ala Lys Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
                100                 105                 110

Asp Cys Cys Glu Lys Gln Glu Pro Glu Arg Asn Glu Cys Phe Leu Thr
            115                 120                 125

His Lys Asp Asp His Pro Asn Leu Pro Lys Leu Lys Pro Glu Pro Asp
130                 135                 140

Ala Gln Cys Ala Ala Phe Gln Glu Asp Pro Asp Lys Phe Leu Gly Lys
145                 150                 155                 160

Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
            180                 185                 190

Pro Ala Asp Asp Lys Ala Gly Cys Leu Ile Pro Lys Leu Asp Ala Leu
            195                 200                 205

Lys Glu Arg Ile Leu Leu Ser Ser Ala Lys Glu Arg Leu Lys Cys Ser

```
                210                 215                 220
Ser Phe Gln Lys Phe Gly Glu Arg Ala Phe Lys Ala Trp Ser Val Ala
225                 230                 235                 240

Arg Leu Ser Gln Lys Phe Pro Lys Ala Asp Phe Ala Glu Val Ser Lys
                245                 250                 255

Ile Val Thr Asp Leu Thr Lys Val His Lys Glu Cys Cys His Gly Asp
                260                 265                 270

Leu Leu Glu Cys Ala Asp Asp Arg Ala Asp Leu Thr Lys Tyr Ile Cys
                275                 280                 285

Glu His Gln Asp Ser Ile Ser Gly Lys Leu Lys Ala Cys Cys Asp Lys
                290                 295                 300

Pro Leu Leu Gln Lys Ser His Cys Ile Ala Glu Val Lys Glu Asp Asp
305                 310                 315                 320

Leu Pro Ser Asp Leu Pro Ala Leu Ala Ala Asp Phe Ala Glu Asp Lys
                325                 330                 335

Glu Ile Cys Lys His Tyr Lys Asp Ala Lys Asp Val Phe Leu Gly Thr
                340                 345                 350

Phe Leu Tyr Glu Tyr Ser Arg Arg His Pro Asp Tyr Ser Val Ser Leu
                355                 360                 365

Leu Leu Arg Ile Ala Lys Thr Tyr Glu Ala Thr Leu Glu Lys Cys Cys
370                 375                 380

Ala Glu Ala Asp Pro Pro Ala Cys Tyr Ala Thr Val Phe Asp Gln Phe
385                 390                 395                 400

Thr Pro Leu Val Glu Glu Pro Lys Ser Leu Val Lys Lys Asn Cys Asp
                405                 410                 415

Leu Phe Glu Glu Val Gly Glu Tyr Asp Phe Gln Asn Ala Leu Ile Val
                420                 425                 430

Arg Tyr Thr Lys Lys Ala Pro Gln Val Ser Thr Pro Thr Leu Val Glu
                435                 440                 445

Ile Gly Arg Thr Leu Gly Lys Val Gly Ser Arg Cys Cys Lys Leu Pro
                450                 455                 460

Glu Ser Glu Arg Leu Pro Cys Ser Glu Asn His Leu Ala Leu Ala Leu
465                 470                 475                 480

Asn Arg Leu Cys Val Leu His Glu Lys Thr Pro Val Ser Glu Lys Ile
                485                 490                 495

Thr Lys Cys Cys Thr Asp Ser Leu Ala Glu Arg Arg Pro Cys Phe Ser
                500                 505                 510

Ala Leu Glu Leu Asp Glu Gly Tyr Ile Pro Lys Glu Phe Lys Ala Glu
                515                 520                 525

Thr Phe Thr Phe His Ala Asp Ile Cys Thr Leu Pro Glu Asp Glu Lys
                530                 535                 540

Gln Ile Lys Lys Gln Ser Ala Leu Ala Glu Leu Val Lys His Lys Pro
545                 550                 555                 560

Lys Ala Thr Lys Glu Gln Leu Lys Thr Val Leu Gly Asn Phe Ser Ala
                565                 570                 575

Phe Val Ala Lys Cys Cys Gly Ala Glu Asp Lys Glu Ala Cys Phe Ala
                580                 585                 590

Glu Glu Gly Pro Lys Leu Val Ala Ser Ser Gln Leu Ala Leu Ala
                595                 600                 605

<210> SEQ ID NO 7
<211> LENGTH: 607
<212> TYPE: PRT
<213> ORGANISM: Equus caballus
```

<400> SEQUENCE: 7

```
Met Lys Trp Val Thr Phe Val Ser Leu Leu Phe Leu Phe Ser Ser Ala
1               5                   10                  15

Tyr Ser Arg Gly Val Leu Arg Arg Asp Thr His Lys Ser Glu Ile Ala
            20                  25                  30

His Arg Phe Asn Asp Leu Gly Glu Lys His Phe Lys Gly Leu Val Leu
        35                  40                  45

Val Ala Phe Ser Gln Tyr Leu Gln Gln Cys Pro Phe Glu Asp His Val
    50                  55                  60

Lys Leu Val Asn Glu Val Thr Glu Phe Ala Lys Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
            100                 105                 110

Asp Cys Cys Glu Lys Gln Glu Pro Glu Arg Asn Glu Cys Phe Leu Thr
        115                 120                 125

His Lys Asp Asp His Pro Asn Leu Pro Lys Leu Lys Pro Glu Pro Asp
130                 135                 140

Ala Gln Cys Ala Ala Phe Gln Glu Asp Pro Asp Lys Phe Leu Gly Lys
145                 150                 155                 160

Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
            180                 185                 190

Pro Ala Asp Asp Lys Leu Ala Cys Leu Ile Pro Lys Leu Asp Ala Leu
        195                 200                 205

Lys Glu Arg Ile Leu Leu Ser Ser Ala Lys Glu Arg Leu Lys Cys Ser
210                 215                 220

Ser Phe Gln Asn Phe Gly Glu Arg Ala Val Lys Ala Trp Ser Val Ala
225                 230                 235                 240

Arg Leu Ser Gln Lys Phe Pro Lys Ala Asp Phe Ala Glu Val Ser Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Glu His Gln Asp Ser Ile Ser Gly Lys Leu Lys Ala Cys Cys Asp Lys
290                 295                 300

Pro Leu Leu Gln Lys Ser His Cys Ile Ala Glu Val Lys Glu Asp Asp
305                 310                 315                 320

Leu Pro Ser Asp Leu Pro Ala Leu Ala Ala Asp Phe Ala Glu Asp Lys
                325                 330                 335

Glu Ile Cys Lys His Tyr Lys Asp Ala Lys Asp Val Phe Leu Gly Thr
            340                 345                 350

Phe Leu Tyr Glu Tyr Ser Arg Arg His Pro Asp Tyr Ser Val Ser Leu
        355                 360                 365

Leu Leu Arg Ile Ala Lys Thr Tyr Glu Ala Thr Leu Glu Lys Cys Cys
370                 375                 380

Ala Glu Ala Asp Pro Pro Ala Cys Tyr Arg Thr Val Phe Asp Gln Phe
385                 390                 395                 400

Thr Pro Leu Val Glu Glu Pro Lys Ser Leu Val Lys Lys Asn Cys Asp
```

```
            405                 410                 415
Leu Phe Glu Glu Val Gly Glu Tyr Asp Phe Gln Asn Ala Leu Ile Val
        420                 425                 430

Arg Tyr Thr Lys Lys Ala Pro Gln Val Ser Thr Pro Thr Leu Val Glu
        435                 440                 445

Ile Gly Arg Thr Leu Gly Lys Val Gly Ser Arg Cys Cys Lys Leu Pro
        450                 455                 460

Glu Ser Glu Arg Leu Pro Cys Ser Glu Asn His Leu Ala Leu Ala Leu
465                 470                 475                 480

Asn Arg Leu Cys Val Leu His Glu Lys Thr Pro Val Ser Glu Lys Ile
                485                 490                 495

Thr Lys Cys Cys Thr Asp Ser Leu Ala Glu Arg Arg Pro Cys Phe Ser
                500                 505                 510

Ala Leu Glu Leu Asp Glu Gly Tyr Val Pro Lys Glu Phe Lys Ala Glu
                515                 520                 525

Thr Phe Thr Phe His Ala Asp Ile Cys Thr Leu Pro Glu Asp Glu Lys
        530                 535                 540

Gln Ile Lys Lys Gln Ser Ala Leu Ala Glu Leu Val Lys His Lys Pro
545                 550                 555                 560

Lys Ala Thr Lys Glu Gln Leu Lys Thr Val Leu Gly Asn Phe Ser Ala
                565                 570                 575

Phe Val Ala Lys Cys Cys Gly Arg Glu Asp Lys Glu Ala Cys Phe Ala
                580                 585                 590

Glu Glu Gly Pro Lys Leu Val Ala Ser Ser Gln Leu Ala Leu Ala
                595                 600                 605

<210> SEQ ID NO 8
<211> LENGTH: 607
<212> TYPE: PRT
<213> ORGANISM: Camelus bactrianus

<400> SEQUENCE: 8

Met Lys Trp Val Thr Phe Ile Ser Leu Leu Phe Leu Phe Ser Ser Val
1               5                   10                  15

Tyr Ser Arg Gly Val Phe Arg Arg Asp Thr His Lys Ser Glu Ile Ala
                20                  25                  30

His Arg Phe Lys Asp Leu Gly Glu Asp Phe Lys Gly Leu Val Leu
        35                  40                  45

Ile Ala Phe Ser Gln Tyr Leu Gln Gln Cys Pro Phe Asp Asp His Val
    50                  55                  60

Lys Leu Val Asn Glu Val Thr Glu Phe Ala Lys Thr Cys Val Ala Asp
65                  70                  75                  80

Glu Ser Ala Ala Asp Cys Asp Lys Ser Leu His Thr Leu Phe Gly Asp
                85                  90                  95

Lys Leu Cys Thr Val Ala Ser Leu Arg Glu Thr Tyr Gly Glu Met Ala
                100                 105                 110

Asp Cys Cys Glu Lys Gln Glu Pro Glu Arg Asn Glu Cys Phe Leu Gln
                115                 120                 125

His Lys Ser Asp Asn Pro Asp Leu Pro Lys Leu Lys Pro Glu Pro Glu
        130                 135                 140

Ala Leu Cys Thr Ala Phe Gln Glu Asn Glu Lys Arg Phe Gly Gly Lys
145                 150                 155                 160

Tyr Leu Tyr Glu Ile Ala Arg Arg His Pro Tyr Phe Tyr Ala Pro Glu
                165                 170                 175
```

```
Leu Leu Tyr Tyr Ala His Gln Tyr Lys His Val Phe Glu Glu Cys Cys
            180                 185                 190

Lys Asp Ala Asp Lys Ala Ala Cys Leu Leu Pro Lys Leu Asp Ala Leu
            195                 200                 205

Lys Glu Arg Ile Leu Ala Ser Ser Ala Arg Gln Arg Leu Arg Cys Thr
            210                 215                 220

Ser Ile Gln Lys Phe Gly Asp Arg Ala Leu Lys Ala Trp Ser Val Gly
225                 230                 235                 240

His Leu Ser Gln Lys Phe Pro Lys Ala Asp Phe Ala Glu Ile Ser Lys
            245                 250                 255

Ile Val Thr Asp Leu Thr Lys Ile His Lys Glu Cys Cys Gln Gly Asp
            260                 265                 270

Leu Leu Glu Cys Ala Asp Asp Arg Ala Asp Leu Ala Lys Tyr Phe Cys
            275                 280                 285

Asp Asn Gln Glu Thr Ile Ser Ser Lys Leu Lys Glu Cys Cys Glu Lys
            290                 295                 300

Pro Leu Leu Glu Lys Ser His Cys Ile His Glu Ala Glu Arg Asp Glu
305                 310                 315                 320

Met Pro Glu Asn Leu Pro Ala Ile Thr Glu Gln Phe Ala Glu Asp Lys
            325                 330                 335

Asp Val Cys Lys His Tyr Thr Glu Glu Lys Asp Val Phe Leu Gly Met
            340                 345                 350

Phe Leu His Glu Tyr Ala Arg Arg His Pro Glu Tyr Ala Val Ser Leu
            355                 360                 365

Leu Leu Arg Ile Ala Lys Glu Tyr Glu Ala Thr Leu Glu Asp Cys Cys
            370                 375                 380

Ala Lys Asp Asp Pro His Ala Cys Tyr Ala Thr Val Phe Asp Lys Leu
385                 390                 395                 400

Gln His Leu Ala Asp Glu Pro Gln Asn Leu Val Lys Gln Asn Cys Glu
            405                 410                 415

Leu Phe Glu Lys Leu Gly Glu Tyr Gly Phe Gln Asn Asp Ile Leu Val
            420                 425                 430

Arg Tyr Thr Lys Arg Leu Pro Gln Val Ser Thr Pro Thr Leu Val Glu
            435                 440                 445

Val Ala Arg Gly Leu Gly Arg Val Gly Thr Lys Cys Cys Thr Leu Pro
450                 455                 460

Glu Ser Asn Arg Met Ser Cys Ala Glu Asp Tyr Leu Ser Leu Ile Leu
465                 470                 475                 480

Asn Arg Leu Cys Val Leu His Glu Lys Thr Pro Val Ser Pro Arg Val
            485                 490                 495

Thr Lys Cys Cys Thr Glu Ser Leu Val Asn Arg Arg Pro Cys Phe Ser
            500                 505                 510

Ser Leu Thr Ala Asp Glu Thr Tyr Glu Pro Lys Glu Phe Asp Glu Lys
            515                 520                 525

Thr Phe Thr Phe His Ala Asp Leu Cys Ser Val Ser Glu Pro Glu Lys
            530                 535                 540

Gln Ile Lys Lys Gln Thr Ala Leu Ala Glu Leu Leu Lys His Lys Pro
545                 550                 555                 560

Lys Ala Thr Asp Glu Gln Leu Lys Thr Val Met Glu Lys Phe Val Ala
            565                 570                 575

Phe Val Asp Lys Cys Cys Ala Ala Val Asp Lys Glu Ala Cys Phe Thr
            580                 585                 590

Val Glu Gly Pro Leu Leu Val Ala Ala Thr Arg Thr Ala Leu Ala
```

<210> SEQ ID NO 9
<211> LENGTH: 607
<212> TYPE: PRT
<213> ORGANISM: Camelus dromedarius

<400> SEQUENCE: 9

```
Met Lys Trp Val Thr Phe Ile Ser Leu Leu Phe Leu Phe Ser Ser Val
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Asp Phe Lys Gly Leu Val Leu
    35                  40                  45

Ile Ala Phe Ser Gln Tyr Leu Gln Gln Cys Pro Phe Asp Asp His Val
50                  55                  60

Lys Leu Val Asn Glu Val Thr Glu Phe Ala Lys Thr Cys Val Ala Asp
65                  70                  75                  80

Glu Ser Ala Ala Asp Cys Asp Lys Ser Leu His Thr Leu Phe Gly Asp
                85                  90                  95

Lys Leu Cys Thr Val Ala Ser Leu Arg Glu Thr Tyr Gly Glu Met Ala
            100                 105                 110

Asp Cys Cys Glu Lys Gln Glu Pro Glu Arg Asn Glu Cys Phe Leu Gln
        115                 120                 125

His Lys Ser Asp Asn Pro Asp Leu Pro Lys Leu Lys Pro Glu Pro Glu
    130                 135                 140

Ala Leu Cys Thr Ala Phe Gln Glu Asn Glu Lys Arg Phe Gly Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala His Gln Tyr Lys His Val Phe Glu Glu Cys Cys
            180                 185                 190

Lys Asp Ala Asp Lys Ala Ala Cys Leu Leu Pro Lys Leu Asp Ala Leu
        195                 200                 205

Lys Glu Arg Ile Leu Ala Ser Ser Ala Arg Gln Arg Leu Arg Cys Thr
    210                 215                 220

Ser Ile Gln Lys Phe Gly Asp Arg Ala Leu Lys Ala Trp Ser Val Gly
225                 230                 235                 240

His Leu Ser Gln Lys Phe Pro Lys Ala Asp Phe Ala Glu Ile Ser Lys
                245                 250                 255

Ile Val Thr Asp Leu Thr Lys Ile His Lys Glu Cys Cys Gln Gly Asp
            260                 265                 270

Leu Leu Glu Cys Ala Asp Asp Arg Ala Asp Leu Ala Lys Tyr Phe Cys
        275                 280                 285

Asp Asn Gln Glu Thr Ile Ser Ser Lys Leu Lys Glu Cys Cys Glu Lys
    290                 295                 300

Pro Leu Leu Glu Lys Ser His Cys Ile His Glu Ala Glu Arg Asp Glu
305                 310                 315                 320

Met Pro Glu Asn Leu Pro Ala Ile Thr Glu Gln Phe Ala Glu Asp Lys
                325                 330                 335

Asp Val Cys Lys His Tyr Thr Glu Glu Lys Asp Val Phe Leu Gly Met
            340                 345                 350

Phe Leu His Glu Tyr Ala Arg Arg His Pro Glu Tyr Ala Val Ser Leu
        355                 360                 365
```

-continued

```
Leu Leu Arg Ile Ala Lys Glu Tyr Glu Ala Thr Leu Glu Asp Cys Cys
    370             375                 380

Ala Lys Asp Asp Pro His Ala Cys Tyr Ala Thr Val Phe Asp Lys Leu
385             390                 395                 400

Gln His Leu Ala Asp Glu Pro Gln Asn Leu Val Lys Gln Asn Cys Glu
            405                 410                 415

Leu Phe Glu Lys Leu Gly Glu Tyr Gly Phe Gln Asn Asp Ile Leu Val
            420                 425             430

Arg Tyr Thr Lys Arg Leu Pro Gln Val Ser Thr Pro Thr Leu Val Glu
        435                 440             445

Val Ala Arg Gly Leu Gly Arg Val Gly Thr Lys Cys Cys Thr Leu Pro
450                 455                 460

Glu Ser Asn Arg Met Ser Cys Ala Glu Asp Tyr Leu Ser Leu Ile Leu
465             470                 475                 480

Asn Arg Leu Cys Val Leu His Glu Lys Thr Pro Val Ser Pro Arg Val
                485                 490             495

Thr Lys Cys Cys Thr Glu Ser Leu Val Asn Arg Arg Pro Cys Phe Ser
            500             505                 510

Ser Leu Thr Ala Asp Glu Thr Tyr Glu Pro Lys Glu Phe Asp Glu Lys
            515                 520             525

Thr Phe Thr Phe His Ala Asp Leu Cys Ser Val Ser Glu Pro Glu Lys
            530             535             540

Gln Ile Lys Lys Gln Thr Ala Leu Ala Glu Leu Leu Lys His Lys Pro
545             550                 555                 560

Lys Ala Thr Asp Glu Gln Leu Lys Thr Val Met Glu Lys Phe Val Ala
            565                 570                 575

Phe Val Asp Lys Cys Cys Ala Ala Val Asp Lys Glu Ala Cys Phe Thr
            580             585                 590

Val Glu Gly Pro Leu Leu Val Ala Ala Thr Arg Thr Ala Leu Ala
            595             600             605
```

ALBUMIN-BASED NON-COVALENT COMPLEXES AND METHODS OF USE THEREOF

CROSS-REFERENCE

This application is a divisional of U.S. patent application Ser. No. 16/056,366 filed on Aug. 6, 2018, now U.S. Pat. No. 10,342,855, which is a divisional of U.S. patent application Ser. No. 15/148,587 filed on May 6, 2016, now U.S. Pat. No. 10,071,141, which application claims the benefit of U.S. Provisional Patent Application No. 62/294,931, filed Feb. 12, 2016, and U.S. Provisional Patent Application No. 62/158,670, filed May 8, 2015, which applications are incorporated herein by reference in their entireties.

GOVERNMENT RIGHTS

This Invention was made with government support under (W911NF13C0047) awarded by the US Department of Defense. The government has certain rights in the invention.

INTRODUCTION

Albumin is the most abundant protein in plasma, accounting for more than half of human plasma protein. It is important for various physiological processes such as providing colloid osmotic pressure, solubilizing long chain fatty acids, delivery of water insoluble nutrients to cells, and balancing plasma pH. Albumin naturally accumulates at tumors and sites of inflammation, a characteristic which can be augmented by the addition of targeting ligands. Albumin has two hydrophobic binding sites, in which it can transport a hydrophobic ligand that would normally be insoluble in water.

Bacterial/fungal cells produce various proteins that bind to albumin and likely impart survival ability against vertebrate host defense mechanisms and/or virulence to the bacterial cells. Many gram-positive bacteria express surface proteins with ability to bind serum proteins. The surface proteins typically contain repeated tandem serum protein-binding domains with one or several specificities, which often include albumin binding. The bacteria can thereby camouflage themselves with bound host-proteins to evade the immune system and potentially also scavenge protein-bound nutrients Expression of albumin-binding proteins has been shown to promote bacterial growth and virulence. There are many different types of albumin-binding proteins with different size and function. For example, more than 40 albumin-binding domains have been found in one protein, forming a rod-like structure in a giant cell wall-associated fibronectin-binding molecule. Protein G-related albumin-binding (GA) modules occur on the surface of numerous Gram-positive bacterial pathogens and their presence may promote bacterial growth and virulence in mammalian hosts.

SUMMARY

Provided herein are hydrophobic ligand-albumin complexes, and methods of making and using the same. The present hydrophobic ligand-albumin complexes provide a delivery vehicle for targeting a hydrophobic molecule to a microorganism, and may find use in the detection, e.g., optical detection, of microorganisms in a sample and in the formulation of therapeutic compositions containing hydrophobic active agents, e.g., hydrophobic antibacterial or antifungal agents, for administration to an individual in need thereof.

BRIEF DESCRIPTION OF THE DRAWINGS

The skilled artisan will understand that the drawings, described below, are for illustration purposes only. The drawings are not intended to limit the scope of the present teachings in any way.

FIG. 25 provides NCBI Reference Sequence: NP_000468.1 for human serum albumin preprotein.

FIG. 26 provides NCBI Reference Sequence: NP_851335.1 for bovine serum albumin precursor.

FIG. 27 provides NCBI Reference Sequence: NP_033784.2 for mouse serum albumin preprotein.

FIG. 28 provides NCBI Reference Sequence: NP_599153.2 for rat serum albumin precursor.

FIG. 29 provides NCBI Reference Sequence: XP_005681801.1 for goat serum albumin (predicted).

FIG. 30 provides NCBI Reference Sequence: NP_001310707.1 for donkey serum albumin precursor.

FIG. 31 provides NCBI Reference Sequence: NP_001075972.1 for horse serum albumin precursor.

FIG. 32 provides NCBI Reference Sequence: XP_010967650.1 for camel serum albumin (predicted).

FIG. 33 provides NCBI Reference Sequence: XP_010981066.1 for camel serum albumin (predicted).

DEFINITIONS

Figure 1:
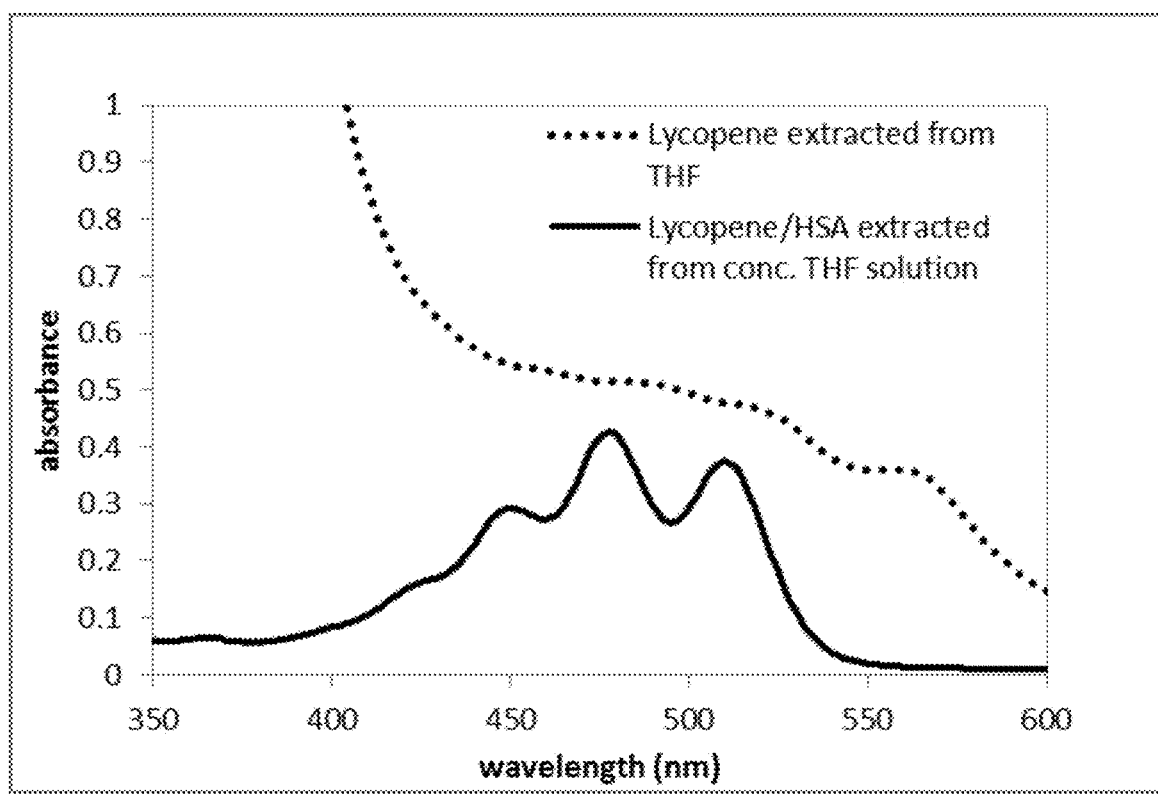
FIG. 1 is a graph showing the absorption spectrum of concentrated lycopene solution in hexane, extracted from a tetra-hydro furan (THF) solution; and dilute lycopene in human serum albumin (HSA) extracted from THF, according to embodiments of the present disclosure.

The term "about" as used herein when referring to a measurable value such as an amount, a temporal duration, and the like, is meant to encompass variations of ±20% or ±10%, e.g., ±5%, ±1%, and including ±0.1% from the specified value, as such variations are appropriate to perform the disclosed methods or achieve the desired results.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

A "microorganism" as used herein, may refer to any organism that is characterized by having a cell wall. Such organisms may include, without limitation, prokaryotes (such as Bacteria and Archaea) and fungi.

"Complex" as used herein, may refer to two or more entities that physically associate with each other, but not with other entities. The two or more entities may be able to migrate or diffuse through a medium as a single unit.

"Hydrophobic" as used herein, may describe a molecule or compound that is poorly soluble in water, at least around physiological pH. In some cases, the molecule or compound may have solubility in water of 1.0 mg/mL or less, e.g., at 25° C.

"Functionally associate", as used herein, may be used to describe a first entity and a second entity physically interacting, directly or indirectly, with each other such that a property of the first entity and/or the second entity is altered as a result of the interaction. In some cases, the physical interaction may include the first entity binding to, or forming a complex with, the second entity, or the first entity being transferred to the second entity.

As used herein, "Raman scattering," and other similar terms and/or phrases, may refer to any method whereby light incident on a sample at a fixed wavelength is scattered at other wavelengths. The scattering may be by an incoherent process due to the absorption of the incident photon by the excitation of the structure from an initially lower (the ground state) to a higher vibrational level, and subsequent relaxation down to a different ground state level.

As used herein, "Raman band" and similar terms and/or phrases may refer to the spectral profile (e.g. intensity versus frequency) corresponding to the Raman scattering from a particular chemical bond within a molecule. It is understood that each chemical bond manifests as a Raman band at distinct frequencies and that in some cases, these Raman bands may overlap, making them difficult to distinguish. Further, it is understood that the Raman cross section of a chemical bond is a "constant" that defines the intensity of the corresponding Raman peak. Furthermore, it is understood that this cross section can change with wavelength of incident light, and/or with optical resonance of the incident light with an absorption band, and/or with changes in the immediate environment of that chemical bond. Such a resonance change occurs during resonant Raman enhancement.

As used herein, it is understood that the "Raman spectrum" of a sample, and similar terms and/or phrases, refer to the sum of all the Raman bands, and the relative heights on individual Raman bands in a Raman spectrum is proportional to the relative abundance of the corresponding chemical bonds multiplied by their Raman cross section.

As used herein, "absorption" and similar terms and or phrases refer to any method wherein incident light is absorbed by a sample of interest. The incident photon may interact with a structure by any number of mechanisms, including the excitation of outer electrons (e.g. corresponding to the absorption of UV or visible radiation), or the excitation of the molecule into higher vibrational/rotational energy states.

As used herein, "Resonant Raman scattering," and similar phrases and/or terms, refers to a process that is understood to be a special type of Raman scattering process that involves the excitation of a molecule from an initial ground state to a real excited state that corresponds to a real vibrational state. Thus, for the purpose of the present discussion, resonant "Raman enhancement" (or "resonance Raman"), and other similar terms and/or phrases, refer to any method whereby the Raman cross section of a particular band is enhanced by the strong optical absorption.

As used herein, "profile" may refer to a set of measurements of a property of a sample obtained across one or more dimensions in time and/or space. A "temporal profile" may be obtained by measuring the property over a plurality of time points. A "spatial profile" may be obtained by measuring a property over a plurality of locations. In some cases, the plurality of locations is a plurality of locations substantially in one dimension (i.e., substantially along a line in space).

An "aggregate" as used herein, may refer to a collection of molecules in a liquid medium, wherein the molecular interactions are stable enough to detectably alter a physical property of the system, compared to a system in which the molecules do not exhibit the interactions among themselves in the liquid medium. The physical property altered may include an optical property (e.g., absorbance, Raman spectrum) of the system.

As used herein, "vial" and other similar terms and/or phrases refer to a test container that contains the test sample along with any other components of the assay. It is understood that the vial can be constructed out of any suitably transparent material, such as glass and plastics.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a hydrophobic molecule" includes a plurality of such hydrophobic molecules and reference to "the albumin protein" includes reference to one or more albumin proteins and equivalents thereof known to those skilled in the art, and so forth. It is further noted that the claims may be drafted to exclude any element. As such, this statement is intended to serve as antecedent basis for use of such exclusive terminology as "solely," "only" and the like in connection with the recitation of claim elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication by virtue of prior disclosure. Further, the dates of publication provided may be different from the actual publication dates which may need to be independently confirmed.

DETAILED DESCRIPTION

As summarized above, hydrophobic ligand-albumin complexes, and methods of making and using the same are provided. The present hydrophobic ligand-albumin complexes may retain many properties of albumin in uncomplexed form, such as the ability to stay unaggregated under normal operation and the ability to aggregate under specific conditions. The hydrophobic ligand-albumin complex may remain soluble in aqueous solution as prepared, and may provide an efficient way to deliver a hydrophobic molecule that is not normally soluble in aqueous solution to a target, e.g., an albumin-binding target, in aqueous solution. Many infectious or opportunistic microorganisms express albumin-binding moieties on the cell surface, e.g., on the surface of the cell wall. Thus, the hydrophobic ligand-albumin complex can deliver the hydrophobic molecule in complex with albumin to microorganisms. A hydrophobic ligand-albumin of the present disclosure may find use in detecting microorganisms in a sample, e.g., a clinical sample, or to enhance the efficacy of antimicrobial compounds. For example, in the case of a hydrophobic antimicrobial compounds, a complex of an antimicrobial compound with the albumin may provide: (a) effective solubilization of the antimicrobial agent, such that it can be transported effectively; (b) preferential transport of the antimicrobial to the pathogen (as opposed to enhanced transport in a random direction); and (c) deposition of the antimicrobial agent on the surface of the pathogenic microorganism.

Further aspects of the present disclosure are now described.

Hydrophobic L Ligand-Albumin Complexes

Provided herein is a non-covalent complex of a hydrophobic molecule/ligand and an albumin protein, where the interaction between the hydrophobic ligand and the albumin in the complex does not include a covalent bond. A complex of the present disclosure does not include an aggregate of two or more albumin protein molecules, such as nanoparticles of albumin. However, multiple complexes of the present disclosure, each containing an albumin protein, may form an aggregate in solution under certain circumstances, as described herein.

The albumin protein may be any suitable albumin. Suitable albumin proteins include, but are not limited to, human serum albumin (HSA; Gene ID: 213); bovine serum albumin (BSA; Gene ID: 280717); mouse albumin (Gene ID: 11657); rat albumin (Gene ID: 24186); goat albumin (Gene ID: 100860821); donkey albumin (Gene ID: 106835108); horse albumin (Gene ID: 100034206); camel albumin (Gene ID: 105080389 or 105091295), etc. The albumin protein may also include any albumin variants suitable for use in a hydrophobic ligand-albumin complex.

In some embodiments, a suitable human serum albumin protein comprises an amino acid sequence having at least about 80%, at least about 85%, at least about 90%, at least about 95%, at least about 98%, at least about 99%, or 100%, amino acid sequence identity to amino acids 25-609 of the amino acid sequence depicted in FIG. 25 (SEQ ID NO:1).

In some embodiments, a suitable bovine serum albumin protein comprises an amino acid sequence having at least about 80%, at least about 85%, at least about 90%, at least about 95%, at least about 98%, at least about 99%, or 100%, amino acid sequence identity to amino acids 25-607 of the amino acid sequence depicted in FIG. 26 (SEQ ID NO:2).

In some embodiments, a suitable mouse serum albumin protein comprises an amino acid sequence having at least about 80%, at least about 85%, at least about 90%, at least about 95%, at least about 98%, at least about 99%, or 100%, amino acid sequence identity to amino acids 25-608 of the amino acid sequence depicted in FIG. 27 (SEQ ID NO:3).

In some embodiments, a suitable rat serum albumin protein comprises an amino acid sequence having at least about 80%, at least about 85%, at least about 90%, at least about 95%, at least about 98%, at least about 99%, or 100%, amino acid sequence identity to amino acids 25-608 of the amino acid sequence depicted in FIG. 28 (SEQ ID NO:4).

In some embodiments, a suitable goat serum albumin protein comprises an amino acid sequence having at least about 80%, at least about 85%, at least about 90%, at least about 95%, at least about 98%, at least about 99%, or 100%, amino acid sequence identity to amino acids 25-607 of the amino acid sequence depicted in FIG. 29 (SEQ ID NO:5).

In some embodiments, a suitable donkey serum albumin protein comprises an amino acid sequence having at least about 80%, at least about 85%, at least about 90%, at least about 95%, at least about 98%, at least about 99%, or 100%, amino acid sequence identity to amino acids 25-607 of the amino acid sequence depicted in FIG. 30 (SEQ ID NO:6).

In some embodiments, a suitable horse serum albumin protein comprises an amino acid sequence having at least about 80%, at least about 85%, at least about 90%, at least about 95%, at least about 98%, at least about 99%, or 100%, amino acid sequence identity to amino acids 25-607 of the amino acid sequence depicted in FIG. 31 (SEQ ID NO:7).

In some embodiments, a suitable camel serum albumin protein comprises an amino acid sequence having at least about 80%, at least about 85%, at least about 90%, at least about 95%, at least about 98%, at least about 99%, or 100%, amino acid sequence identity to amino acids 25-607 of the amino acid sequence depicted in FIG. 32 (SEQ ID NO:8).

In some embodiments, a suitable camel albumin protein comprises an amino acid sequence having at least about 80%, at least about 85%, at least about 90%, at least about 95%, at least about 98%, at least about 99%, or 100%, amino acid sequence identity to amino acids 25-607 of the amino acid sequence depicted in FIG. 33 (SEQ ID NO:9).

The hydrophobic ligand of the present complex may be any suitable hydrophobic molecule that can bind to an albumin molecule while substantially maintaining desired properties of albumin molecule, e.g., solubility, binding ability to other albumin molecules and/or albumin receptors, etc. In some cases, a suitable hydrophobic molecule can bind to an albumin molecule without significantly altering the interaction with other albumin molecules that would in turn significantly alter aggregation of albumin in solution.

The hydrophobic molecule may have any suitable molecular weight to bind a hydrophobic binding site of albumin. In some cases, the hydrophobic molecule has a molecular weight of 100 kD or less, e.g., 50 kD or less, 20 kD or less, 10 kD or less, 5.0 kD or less, including 1.0 kD or less, and has a molecular weight of 0.05 kD or more, e.g., 0.1 kD or more, 0.2 kD or more, 0.3 kD or more, including 0.5 kD or more. In some embodiments, the hydrophobic molecule has a molecular weight in the range of 0.05 kD to 100 kD, e.g., 0.05 kD to 50 kD, 0.1 kD to 20 kD, including 0.1 kD to 10 kD. Binding of a hydrophobic molecule to albumin can be measured using any suitable method, such as those described herein, and by competition assays with known albumin binding agents (see, e.g., US 20150309040, which is incorporated herein by reference), or any other suitable method.

In some cases, the hydrophobic molecule includes a chromophore, e.g., a chromophore whose optical property is concentration-dependent due to an optical interaction between adjacent molecules in close proximity. The chromophore concentration-dependent optical property may be any suitable optical property for detecting a change in the aggregation status of the chromophore-containing molecule. In some cases, the absorbance of the chromophore is altered (e.g., red-shifted or blue shifted) in a concentration-dependent manner due to optical interactions between molecules that contain the chromophore. In some cases, the Raman scattering of the chromophore is altered (e.g., more or less efficient) in a concentration-dependent manner due to optical interactions between molecules that contain the chromophore.

Suitable chromophore-containing molecules include, but are not limited to, carotenoids. Carotenoids of interest include, but are not limited to, carotene (e.g., α-carotene, β-carotene, γ-carotene, δ-carotene, ε-carotene, lycopene, etc.) and xanthophylls (e.g., lutein, zeaxanthin, neoxanthin, violaxanthin, flavoxanthin, α- and β-cryptoxanthin, etc.).

In some cases, suitable carotenoids are those compounds that have a strong resonance Raman peak. For example, excitation of many carotenoids with monochromatic light induces prominent resonance Raman peaks at wavenumbers around 1520 cm$^{-1}$ and around 1160 cm$^{-1}$ (see, e.g., Merlin. *Pure and Applied Chemistry* 57.5 (1985): 785-792). Specifically for lycopene, the Raman spectrum of lycopene excited at a wavelength of 532 nm includes two strong peaks at 1516 and 1156 cm$^{-1}$ (see, e.g., Hoskins, *Journal of Chemical Education* 61, no. 5 (1984): 460; and Lopez-Ramirez et al., *Journal of Raman Spectroscopy* 41.10 (2010): 1170-1177). The peaks at 1516 and 1156 cm$^{-1}$ correspond to the v(C=C) and v(C—C) vibrations typical of conjugated polyenes, and are referred to as $v_1$ and $v_2$ modes.

In some cases, the hydrophobic molecule includes a fluorophore, e.g., a fluorophore whose optical property is concentration-dependent due to an optical interaction between adjacent molecules in close proximity. The fluorophore concentration-dependent optical property may be any suitable optical property for detecting a change in the aggregation status of the fluorophore. In some cases, the hydrophobic molecule is one of a Förster resonance energy transfer (FRET) pair of fluorescent molecules. In such a case, the hydrophobic molecule may be a donor or an acceptor of the FRET pair, such as DiIC$_{18}$(3) (DiI) and DiOC18(3) (DiO).

In some embodiments, the hydrophobic molecule is an antimicrobial agent. The antimicrobial agent may be any suitable hydrophobic compound with antimicrobial activity. In some cases, the antimicrobial agent is an antibacterial (antibiotic) or an antifungal agent. Suitable antibacterial agents include, without limitation, clofazimine, chlorhexidine, tetracycline, tobramycin, and gentamicin. Suitable antifungal agents include, without limitation, amphotericin B, pimaricin, filipin, nystatin, itraconazole, ketoconazole, fluconazole, saperconazole, miconazole, ravunconazole, posaconazole, voriconazole, ciclopirox olamine, butoconazole and tolnaftate.

In some cases, the antimicrobial agent is a pharmacologically active agent. Any suitable hydrophobic pharmacologically active agent may be complexed with albumin. In some cases, the pharmacologically active agent is an anti-cancer drug, an anti-viral drug or a cardiovascular drug. Suitable anti-cancer drugs include, without limitation, camptothecin, silatecan 7-t-butyldimethyl silyl-10-hydroxycamptothecin (DB-67), 7-ethyl-10-hydroxy-20(S)-camptothecin (SN-38), topotecan, irinotecan, 9-nitro-camptothecin, lurtotecan, exatecan, gimatecan, karenitecin, paclitaxel, 5-fluorouracil, prednisone, medroxyprogesterone, megestrol, diethylstilbestrol, melphalan and chlorambucil. Suitable anti-viral drugs include, without limitation, disoxaril, adefovir, maraviroc, dipivoxil, delavirdine, efavirenz, nevirapine, darunavir, amprenavir and tipranavir. Suitable cardiovascular drugs include, without limitation, gemfibrozil, tetrahydrolipstatin, cholestyramine, colestipol, lovastatin, probucol, and squalene.

The hydrophobic ligand-albumin complex of the present disclosure may be soluble in aqueous solution, as prepared by a method described herein. Thus, in some cases, incorporation of the hydrophobic molecule in albumin does not perturb the molecular interactions between albumin sufficiently to cause aggregation of albumin at standard conditions (e.g., at standard temperature and pressure (STP), or at physiological conditions).

While albumin can incorporate hydrophobic ligands, the incorporation of hydrophobic ligands may alter the solubility of the albumin in a manner that may enable density fluctuations. As examples, lycopene and β-carotene are considered as hydrophobic ligands. The phase separation of albumins with and without lycopene and beta carotene can be understood with 4 terms: (a) HSA/Lyc-HSA interaction parameter ($\chi_{12}$), (b) HSA/Lyc-water and HSA-water interaction parameters ($\chi_{1w}$, $\chi_{2w}$), (c) molecular weights of the two protein molecules, and (d) conformation states of the two proteins.

From the Flory-Huggins solution theory, the critical interaction parameter, $\chi_C$, for a binary mixture of polymers is 0 (two components will be miscible only if their interaction parameter is below $\chi_C$). However, in a ternary system with a solvent, if the solvent (water in the case of albumin in serum with and without a ligand) is equally good for both proteins $|\chi_{1w}-\chi_{2w}|=0$; then the two proteins can be totally miscible solution in spite of a small positive value of $\chi_{12}$. Likewise, two proteins in water may be incompatible if they have a different interaction with water $|\chi_{1w}-\chi_{2w}|$; with a difference of as little as 0.03 sufficing for incompatibility, and the threshold for phase separation being lowered as $|\chi_{1w}-\chi_{2w}|$ increases.

The albumin-water interaction parameters $\chi_{1w}$ and $\chi_{2w}$ can be estimated from the Hildebrand solubility parameters δ.

$$\chi_{pw} = \frac{V_o}{RT}(\delta_p - \delta_w)^2$$

Where Vo is the molar volume of the solvent (water). In turn, δ can be calculated from the group contribution method of Van Krevelen.

When comparing albumin with and without lycopene (as an example of a hydrophobic ligand~the values will be very similar for β-carotene), the Hildebrand parameters δ for water, albumin and β-carotene (are 43, 23.31 and 14.29 J$^{1/2}$ cm$^{-3/2}$, respectively) are used; and using those values, $\delta_2$=23.31 for HSA and $\delta_1$=23.24 for HSA/lyc J$^{1/2}$ cm$^{-3/2}$. With these numbers, $\chi_{1w}$=2.81 and $\chi_{2w}$=2.79, and $|\chi_{1w}-\chi_{2w}|$=0.02.

It is noted that this difference is just below the previously noted threshold for incompatibility between two proteins in water. Thus, while outright phase separation is unlikely in the absence of an additional stimulus, fluctuations in lycopene density is possible/likely. Further, it is noted that albumin has two binding sites; and if it carries two lycopene molecules (one at each binding site), then $|\chi_{1w}-\chi_{2w}|$=0.04; which is above the threshold of 0.03. Thus the double filled albumin may phase separate into aggregates.

These density fluctuations may result in scattering if the length scale of these fluctuations is comparable to the length scale of light, and if the light is tuned such that it is absorbed only by the lycopene. Thus, depending on the magnitude and length scale of these fluctuations, a finite and variable number of lycopene dense pockets may be observed by the collecting lens and it may appear that the observed lycopene levels are quantized, and that these levels are reduced below the expected values.

A single albumin molecule may be complexed with any suitable number of hydrophobic ligands based, e.g., on the hydrophobicity of the ligands. In some cases, the albumin is complexed with a single hydrophobic ligand (single filled). In some cases, the albumin is complexed with two hydrophobic ligands (double filled). The extent of the number of hydrophobic ligands on a single albumin protein may be controlled as described further below.

Compositions

Also provided herein are compositions that include a hydrophobic ligand-albumin complex, as described above. A composition of interest includes an aqueous solution that includes an amount of the present hydrophobic ligand-albumin complex. The hydrophobic ligand-albumin complex may be in solution (i.e., does not form aggregates), e.g., when the composition is initially prepared, or reconstituted from a powder from, as described herein. The present composition may find use in assays performed in vitro, e.g., to detect the presence of bacteria in a clinical sample, or in delivering a hydrophobic ligand to a site in vivo, e.g., to administer a pharmaceutically active agent to an individual. As such, the present composition may include any other suitable components for its intended use.

The composition may include any suitable amount of the hydrophobic ligand-albumin complex. In some cases, the composition includes 1.0 nM or more, e.g., 5.0 nM or more, 10 nM or more, 50 nM or more, 100 nM or more, 0.5 µM or more, 1.0 µM or more, including 5.0 µM or more, and includes 10 mM or less, e.g., 5.0 mM or less, 1.0 mM or less, 0.5 mM or less, 0.1 mM or less, 50 µM or less, 10 µM or less, including 5.0 µM or less, of the hydrophobic ligand complexed with albumin, as measured based on the amount of the hydrophobic ligand in the composition. In some embodiments, the composition includes a concentration of the hydrophobic ligand complexed with albumin in the range of 1.0 nM to 10 mM, e.g., 5.0 nM to 5.0 mM, 10 nM to 1.0 mM, 50 nM to 0.5 mM, 100 nM to 0.1 mM, including 0.5 µM to 50 µM, as measured based on the amount of the hydrophobic ligand composition.

The aqueous solution may include any suitable water-based solution. In some cases, the aqueous solution is water. In some cases, the aqueous solution is a buffer, which may include any suitable buffering agent (i.e., pH controlling agents), such as, but not limited to, phosphate, bicarbonate, citrate, tris(hydroxymethyl)aminomethane (Tris), N-Tris (hydroxymethyl)methyl-3-aminopropanesulfonic acid (TAPS), bicine, tricine, 4-(2-hydroxyethyl)-1-piperazineethanesulfonic acid (HEPES), 3-(N-morpholino)propanesulfonic acid (MOPS), 2-(N-morpholino)ethanesulfonic acid (MES) and piperazine-N,N'-bis(2-ethanesulfonic acid) (PIPES). The buffer may include any suitable components, such as minerals/salts, antioxidants (such as, e.g., ascorbic acid), chelating agents (such as, e.g., ethylenediaminetetraacetic acid (EDTA) or glutathione), amino acids (such as, e.g., glycine), proteins, preservatives, tonicity controlling agents, and the like. A suitable buffer includes, but is not limited to, phosphate-buffered saline (PBS).

The pH of the aqueous solution may be any suitable pH. In some cases, the pH of the aqueous solution is greater than 5.4, e.g., 5.5 or higher, 6.0 or higher, 6.5 or higher, 7.0 or higher, 7.5 or higher, 8.0 or higher, including 8.5 or higher, and may be 10.0 or less, e.g., 9.5 or less, 9.0 or less, 8.5 or less, including 8.0 or less. In some cases, the pH of the aqueous solution is in the range of 5.5 to 10.0, e.g., 6.0 to 9.5, 6.5 to 9.0, 6.5 to 8.5, including 6.5 to 8.0.

In some cases, the composition includes an antioxidant, e.g., ascorbic acid. The antioxidant may be present in any suitable amount. In some cases, the antioxidant is present in the composition at 0.001 mg/mL or more, e.g., 0.005 mg/mL or more, 0.01 mg/mL or more, 0.02 mg/mL or more, 0.05 mg/mL or more, including 0.1 mg/mL or more, and at 10 mg/mL or less, e.g., 1.0 mg/mL or less, 0.5 mg/mL or less, 0.1 mg/mL or less, including 0.05 mg/mL or less. In some embodiments, the antioxidant is present in the composition at a concentration in the range of 0.001 to 10 mg/mL, e.g., 0.005 to 1.0 mg/mL, 0.01 to 0.5 mg/mL, 0.01 to 0.1 mg/mL, including 0.01 to 0.05 mg/mL.

In some embodiments, the composition includes a plurality of hydrophobic molecules that have properties, e.g., optical properties, that depend on the intermolecular distance between the hydrophobic molecules, where the composition finds use in detecting microorganisms in a sample, as described further below. In such cases, the composition may further include a nutrition source that can sustain at least some level of metabolism of the microorganism. The nutrition source may be any suitable nutritional medium. In some cases, the nutritional source is trypticase soy broth (TSB), Luria-Bertani (LB) broth, nutrient broth, brain heart infusion broth (BHI), heart infusion broth, M9 broth, peptone water, SOC broth, terrific broth and vegitone.

In some cases, the composition is a therapeutic composition that is suitable for administering to an individual, e.g., to deliver a hydrophobic pharmacological agent to the individual. The hydrophobic pharmacological agent in such a therapeutic composition may be any suitable therapeutic compound, such as an antimicrobial, antiviral, anti-cancer, anti-inflammatory or a cardiovascular agent, as described above.

The therapeutic composition may contain the hydrophobic ligand-albumin complex in a pharmacological acceptable carrier or excipient. As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., ethylenediaminetetraacetic acid (EDTA) or glutathione), amino acids (such as, e.g., glycine), proteins, disintegrants, binders, lubricants, wetting agents, emulsifiers, sweeteners, colorants, flavorings, aromatisers, thickeners, agents for achieving a depot effect, coatings, antibacterial and antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated. By "pharmaceutically acceptable" is meant a material that is not biologically or otherwise undesirable, i.e., the material may be incorporated into a pharmaceutical composition administered to an individual without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

In some cases, a therapeutic composition further includes a second active agent. The second active agent may be any suitable pharmaceutical agent. In some cases, the second active agent is an antimicrobial, antiviral, anti-cancer, anti-inflammatory or a cardiovascular agent that is more soluble and/or has a better pharmacokinetic (PK) profile than the hydrophobic molecule.

A composition of the present disclosure further includes a substantially dry hydrophobic ligand-albumin complex in sheet or powder form. The substantially dry hydrophobic ligand-albumin complex retains its solubility of the hydrophobic ligand-albumin complex prior to the drying when reconstituted in a suitable aqueous solution, e.g., a buffer, as described above. The substantially dry hydrophobic ligand-albumin complex may be obtained from an aqueous composition containing the soluble hydrophobic ligand-albumin complex, as described above, by any suitable drying method that preserves the functional properties of the albumin and hydrophobic ligand when reconstituted. In some cases, the substantially dry hydrophobic ligand-albumin complex is produced by freeze drying an aqueous composition containing the soluble hydrophobic ligand-albumin complex. In other cases, the substantially dry hydrophobic ligand-albumin complex is produced by lowering the pH of the solution to the pH that is close to the isoelectric pH of the host albumin (ie, the pH at which the surface charge on the albumin is close to 0), whereby the ligand-albumin complex forms aggregates that crash out of solution, and the solution is then either decanted or filtered off.

Methods

Method of Making a Hydrophobic Ligand-Albumin Complex

Further provided herein is a method of forming a non-covalent complex of a hydrophobic molecule and an albumin protein in solution. In general terms, the method includes dissolving the hydrophobic molecule in a suitable organic solvent to form a first solution; combining the first solution with a second solution to provide a third solution, wherein the second solution is an aqueous solution of albumin; and removing the organic solvent from the third solution to provide a fourth aqueous solution which contains the non-covalent complex of the hydrophobic molecule and a single albumin protein. The organic solvent of the first solution includes at least an organic compound that has solubility, miscibility with water, presence and/or distribution of polar groups, and/or an ability to alter albumin conformation that is similar to acetone. The organic compound may be a ketone-containing compound, such as an aliphatic ketone that includes 3-5 carbon atoms (i.e., a $C_3$-$C_5$ ketone), such as, but not limited to, acetone, methyl ethyl ketone, 2-pentanone, and 3-pentanone. The albumin in the second solution may be dissolved, i.e., not aggregated, in the aqueous solution.

In some cases, the hydrophobic molecule is soluble in the $C_3$-$C_5$ ketone-containing compound, e.g., it is soluble in acetone. For such cases, in some embodiments, the hydrophobic molecule is dissolved in a first organic solvent that is the $C_3$-$C_5$ ketone-containing compound, e.g. acetone. In some cases, the hydrophobic molecule is not soluble in the $C_3$-$C_5$ ketone-containing compound, e.g., not soluble in acetone, but is at least partially soluble in a second organic solvent. For such cases, in some embodiments, the hydrophobic molecule is dissolved in a first organic solvent that contains a mixture of the $C_3$-$C_5$ ketone-containing compound as well as the second organic solvent. The second organic solvent may include any suitable organic compound that can dissolve the hydrophobic molecule, is more volatile than water, and is miscible with the ketone-containing compound, e.g., miscible with acetone. The second organic solvent may include, without limitation, methanol, ethanol, dichloromethane, acetonitrile, benzene, n-butanol, butyl acetate, carbon tetrachloride, chloroform, cyclohexane, 1,2-dichloroethane, dioxane, ethyl acetate, diethyl ether, heptane, hexane, methyl-t-butyl ether, 2-butanone, pentane, n-propanol, isopropanol, diisopropyl ether, tetrahydrofuran, toluene, trichloroethylene, and combinations thereof. In some cases, the hydrophobic molecule is initially dissolved in a second organic solvent containing one or more of the second organic compounds. Then the second organic solvent is combined with the $C_3$-$C_5$ ketone-containing compound, e.g., acetone.

The ratio of the first organic solvent to the second organic solvent may be any suitable ratio to provide for the hydrophobic ligand-albumin complex using the present method. In some cases, the ratio of the first organic solvent to the second organic solvent used to provide the first solution is about 0.001:1 or greater, e.g., about 0.01:1 or greater, about 0.1:1 or greater, about 0.2:1 or greater, including about 1:1 or greater, and is about 1,000:1 or less, about 100:1 or less, about 10:1 or less, about 5:1 or less, including about 1:1 or less, by volume. In some embodiments, the ratio of the first organic solvent to the second organic solvent is in the range from about 0.001:1 to about 1,000:1, e.g., from about 0.01:1 to about 100:1, from about 0.1:1 to about 10:1, including from about 0.2:1 to about 5:1, by volume. In some cases, the ratio of the first organic solvent to the second organic solvent is about 2:1.

The amount of hydrophobic molecule present in the first solution may vary, depending on the nature of the hydrophobic molecule and the desired outcome. In some cases, the hydrophobic molecule is present in the first solution at a concentration of 0.001 mg/mL or more, e.g., 0.005 mg/mL or more, 0.01 mg/mL or more, 0.05 mg/mL or more, 0.1 mg/mL or more, 0.5 mg/mL or more, including 1.0 mg/mL or more, and at a concentration of 50 mg/mL or less, e.g., 25 mg/mL or less, 10 mg/mL or less, 5.0 mg/mL or less, including 3 mg/mL or less. In some embodiments, the hydrophobic molecule is present in the first solution at a concentration in the range of 0.001 to 50 mg/mL, e.g., 0.01 to 25 mg/mL, 0.05 to 10 mg/mL, including 0.1 to 5.0 mg/mL.

The second solution may include albumin in any suitable amount. The second solution may contain albumin at a concentration of 0.1 mg/mL or more, e.g., 0.5 mg/mL or more, 1.0 mg/mL or more, 5.0 mg/mL or more, 10 mg/mL or more, including 20 mg/mL or more, and at a concentration of 100 mg/mL or less, 50 mg/mL or less, 30 mg/mL or less, 15 mg/mL or less, including 10 mg/mL or less. In some embodiments, the second solution may contain albumin at a concentration in the range of 0.1 to 100 mg/mL, e.g., 0.5 to 50 mg/mL, 1.0 to 30 mg/mL, including 5.0 to 30 mg/mL.

The second solution may include one or more additional components, such as a buffering agent, (i.e., pH controlling agents), such as, but not limited to, phosphate, bicarbonate, citrate, tris(hydroxymethyl)aminomethane (Tris), N-Tris (hydroxymethyl)methyl-3-aminopropanesulfonic acid (TAPS), bicine, tricine, 4-(2-hydroxyethyl)-1-piperazineethanesulfonic acid (HEPES), 3-(N-morpholino)propanesulfonic acid (MOPS), 2-(N-morpholino)ethanesulfonic acid (MES) and piperazine-N,N'-bis(2-ethanesulfonic acid) (PIPES). Other suitable additional components include, without limitation, minerals/salts, antioxidants (such as, e.g., ascorbic acid), chelating agents (such as, e.g., ethylenediaminetetraacetic acid (EDTA) or glutathione), amino acids (such as, e.g., glycine), proteins, preservatives, tonicity controlling agents, and the like. In some cases, the second solution includes phosphate-buffered saline (PBS). In some cases, the second solution includes a compound that modulates albumin conformation such as hydrophobic free radical scavengers (e.g. 2,6-di-tert-butyl-4-methylphenol, Vitamin E).

The pH of the second aqueous solution may be any suitable pH. In some cases, the pH of the aqueous solution is greater than 5.4, e.g., 5.5 or higher, 6.0 or higher, 6.5 or higher, 7.0 or higher, 7.5 or higher, 8.0 or higher, including 8.5 or higher, and may be 10.0 or less, e.g., 9.5 or less, 9.0 or less, 8.5 or less, including 8.0 or less. In some cases, the pH of the aqueous solution is in the range of 5.5 to 10.0, e.g., 6.0 to 9.5, 6.5 to 9.0, 6.5 to 8.5, including 6.5 to 8.0.

In some cases, the second aqueous solution includes an antioxidant, e.g., ascorbic acid. The antioxidant may be present in any suitable amount. In some cases, the antioxidant is present in the second aqueous solution at 0.001 mg/mL or more, e.g., 0.005 mg/mL or more, 0.01 mg/mL or more, 0.02 mg/mL or more, 0.05 mg/mL or more, including 0.1 mg/mL or more, and at 10 mg/mL or less, e.g., 1.0 mg/mL or less, 0.5 mg/mL or less, 0.1 mg/mL or less, including 0.05 mg/mL or less. In some embodiments, the antioxidant is present in the second aqueous solution at a concentration in the range of 0.001 to 10 mg/mL, e.g., 0.005 to 1.0 mg/mL, 0.01 to 0.5 mg/mL, 0.01 to 0.1 mg/mL, including 0.01 to 0.05 mg/mL.

The organic solvent (e.g., the $C_3$-$C_5$ ketone-containing solvent, such as acetone, or a combination of the $C_3$-$C_5$ ketone-containing solvent and a second solvent) may be removed from the third solution using any suitable method that retains the functional properties of the albumin and hydrophobic molecule in the complex to provide a fourth solution, wherein the fourth solution is an aqueous solution including a non-covalent complex of the hydrophobic molecule and a single albumin protein molecule. In some cases, the removing is performed by evaporating the volatile components (e.g., the first organic solvent and/or the second organic solvent) from the mixture of the first and second solutions.

In some cases, the removing, e.g., evaporating, is performed at low temperature and pressure, such as at standard temperature and pressure (STP: 1 atm and room temperature), or any other suitable condition. Evaporation of the organic solvent cools the remaining liquid, which can gradually lower the temperature. In some cases, this may be compensated for by sonicating the liquid—the sonication power raises the temperature of the liquid, and compensates for the lowering of the temperature due to evaporation. By controlling the sonication power, the temperature of the solution can be controlled. In some cases, the evaporating is performed at a temperature (of the mixture) of 0° C. or more, e.g., 5° C. or more, 10° C. or more, 15° C. or more, 20° C. or more, including 30° C. or more, and at a temperature of 40° C. or less, e.g., 38° C. or less, 36° C. or less, 30° C. or less, including 25° C. or less. In some cases, the removing, e.g., evaporating, is performed at a temperature (of the mixture) in the range of 0 to 40° C., e.g., 5 to 38° C., 10 to 38° C., 15 to 38° C., including 20 to 38° C. In some cases, the removing, e.g., evaporating, is performed at an ambient pressure over the mixture of 1 atm or less, e.g., 0.5 atm or less, 0.2 atm or less, including 0.1 atm or less. In some cases, the removing, e.g., evaporating, is performed under vacuum pressure. In some cases, the removing, e.g., evaporating, is performed using a rotary evaporator (rotavap).

In some embodiments, a solution containing albumin (e.g., the second solution, the mixture of the first and second solution, and/or the third solution) may be at a suitable temperature for maintaining a desired albumin conformation and to provide a desired affinity between the hydrophobic ligand and albumin in the complex. In some cases, a solution containing albumin is maintained at a temperature of about 0° C. or more, e.g., about 5° C. or more, about 10° C. or more, about 15° C. or more, about 20° C. or more, including about 30° C. or more, and at a temperature of about 40° C. or less, e.g., about 38° C. or less, about 36° C. or less, about 30° C. or less, including about 25° C. or less. In some cases, a solution containing albumin is at a temperature (of the mixture) in the range of about 0 to about 40° C., e.g., about 5 to about 38° C., about 10 to about 38° C., about 15 to about 38° C., including about 20 to about 38° C.

In some embodiments, the method includes (1) dissolving a hydrophobic molecule into an organic solvent; (2) mixing this organic solvent solution with acetone in an appropriate ratio (if the ligand is insoluble in acetone) or drying the organic solvent and reducing the ligand to powder form and then redissolving the powder into acetone (if the ligand is soluble in acetone); (3) mixing the acetone solution (or acetone-organic solvent mixture solution) with an aqueous solution of human serum albumin; and (4) removing the acetone and other organic solvents with low boiling points by evaporation.

In the present method, the extent of the number of hydrophobic ligands on a single albumin protein may be controlled by controlling the following factors: (a) molar ratios of the hydrophobic molecule, e.g., lycopene, to albumin in the third solution; (b) the dilution of albumin in the aqueous solution, where the more concentrated albumin solutions encourage double filling; (c) the temperature of the transfer process, where lower temperature encourages double filling; and (d) the rate of transfer of the hydrophobic molecule, e.g., lycopene, from the first solution to albumin, where a faster rate encourages double filling.

In some embodiments, the molar ratio of the hydrophobic molecule to albumin in the third solution is 0.001:1 or more, e.g., 0.005:1 or more, 0.01:1 or more, 0.02:1 or more, 0.04:1 or more, including 0.06:1 or more, and, in some embodiments, is 10:1 or less, e.g., 5:1 or less, 2:1 or less, 1:1 or less, 0.5:1 or less, including 0.2:1 or less. In some embodiments, the molar ratio of the hydrophobic molecule to albumin in the third solution is in the range of 0.001:1 to 10:1, e.g., 0.005:1 to 5:1, 0.01:1 to 2:1, 0.02:1 to 1:1, including 0.04:1 to 0.5:1.

For example, in some embodiments, where the hydrophobic molecule is lycopene, if the molar ratio is above 0.5:1, then double filled albumin is observed (this manifests as UV-Vis absorption peaks at 565 nm, an overall red coloration, and a strong background absorption at 600 nm); and if the molar ratio is kept below 0.4:1 then only single filled albumin is observed (this manifests as the absence of any UV-Vis peaks at 565 nm, an overall orange coloration, and nearly no absorption at 600 nm).

The rate of transfer of the hydrophobic molecule, e.g., lycopene, from the first solution to albumin may vary, and may depend on: the concentrations of the hydrophobic molecule in the first solution; the rate of addition of the first solution to the second solution; the vigorousness of the mixing (where less vigorous mixing encourages a faster rate of transfer); and the rate of removal of the first solution from the mixture.

Methods of using a Hydrophobic Ligand-Albumin Complex
Methods of Delivering a Hydrophobic Molecule to a Microorganism A hydrophobic ligand-albumin complex of the present disclosure finds use as a delivery vehicle to transfer the hydrophobic molecule in the complex to a target cell, e.g., a microorganism that has a cell wall, where the hydrophobic molecule becomes associated with the microorganism. In some cases, the hydrophobic ligand-albumin complex transfers and aggregates the hydrophobic molecule to a cell wall of a microorganism. Once localized, or transferred, to a microorganism, the hydrophobic molecule may exert its function, depending on the nature of the hydrophobic molecule, in or on the microorganism.

An aspect of the present disclosure includes a method of delivering a hydrophobic molecule to the cell wall of a microorganism, the method including contacting the microorganism with an aqueous solution containing a non-covalent complex of a hydrophobic molecule and a single albumin protein. It should be noted that the aqueous solution may include many such complexes, wherein each complex is a complex of a hydrophobic molecule or molecules and a single albumin protein molecule. The aqueous solution may be obtained by a method as described herein. In general terms, the method may include mixing an aqueous solution containing the hydrophobic ligand-albumin complex with a composition that contains the microorganism.

The contacting may be performed for a time sufficient to deliver the hydrophobic molecule in the hydrophobic ligand-albumin complex to the microorganism. In some cases, the aqueous solution containing the hydrophobic ligand-albumin complex is contacted with the microorganism for 1 min or more, e.g., 5 min or more, 10 min or more, 15 min or more, 20 min or more, 30 min or more, including 1 hr or more, and, in some cases, is contacted with the microorganism for 48 hrs or less, e.g., 24 hrs or less, 12 hrs or less, 6 hrs or less, 3 hrs or less, 1 hr or less, including 45 minutes or less. In some embodiments, the the aqueous solution containing the hydrophobic ligand-albumin complex is contacted with the microorganism for a length time in the range of 1 min to 48 hrs, e.g., 5 min to 24 hrs, 10 min to 24 hrs, 10 min to 6 hrs, 10 min to 3 hrs, including 10 min to 1 hr.

After the contacting, the method in some cases may include fractionating the aqueous solution, e.g, by centrifuging, to separate any microorganisms from the bulk solution.

Any suitable amount of the hydrophobic ligand-albumin complex may be used to deliver the hydrophobic molecule to the microorganism. In some cases, the concentration of the hydrophobic molecule complexed to albumin in the aqueous solution is 1.0 nM or more, e.g., 5.0 nM or more, 10 nM or more, 20 nM or more, 50 nM or more, 100 nM or more, 200 nM or more, 500 nM or more, including 1,000 nM or more, and in some embodiments, is 1.0 mM or less, e.g., 500 µM or less, 200 µM or less, 100 µM or less, 50 µM or less, 20 µM or less, 10 µM or less, 5.0 µM or less, 2.0 µM or less, including 1.0 µM or less. In some embodiments, the concentration of the hydrophobic molecule complexed to albumin in the aqueous solution is in the range of 1.0 nM to 1.0 mM, e.g., 5.0 nM to 500 µM, 10 nM to 200 µM, 20 nM to 100 µM, 50 nM to 50 µM, 100 nM to 10 µM, including 200 nM to 2.0 µM.

The aqueous solution containing the hydrophobic ligand-albumin complex may include additional components, such as buffers (e.g., PBS), antioxidants (e.g., ascorbic acid), nutrition sources (e.g., TSB), as described above. Thus, the aqueous solution may include a composition containing the hydrophobic ligand-albumin complex, as described above.

In some cases, the contacting occurs in vitro, e.g., in a vessel, tube, vial, well, multiwell plate, dish, flask, etc. In some cases, the contacting occurs in vivo, e.g., in an individual who harbors the microorganism, and to whom a composition that includes the hydrophobic ligand-albumin complex has been administered, e.g., using a therapeutic composition containing the hydrophobic ligand-albumin complex, as described above. In such cases, the aqueous solution contacting the microorganism may be a bodily fluid, e.g., blood, plasma, interstitial fluid, lymph, etc., to which the complex is deposited.

The microorganism may be any suitable microorganism that has a cell wall, and that binds albumin. The microorganism may be bacteria or fungi. In some cases, the microorganism is pathogenic or is an opportunistic pathogen. Microorganisms of interest include, without limitation, *Escherichia coli* 10418, *Esch. coli* 12241, *Staphylococcus aureus*, *Staph. epidermidis*, *Klebsiella pneumoniae*, *Enterobacter cloacae*, *Enterococcus faecalis*, *Streptococcus pneumoniae*, *Pseudomonas aeruginosa*, *Proteus mirabilis*, *Strep. pyogenes*, *Candida albicans*, *Salmonella typhimurium*, *Providencia rettgerri*, *Bacteroides fragilis*, *Acinetobacter baumannii*, *Enterococcus faecium*, *Stenotrophomonas maltophilia*, *Cand. glabrata*, *Staph aureus* (MRSA), and *Citrobacter freundii*.

Methods of Enhancing Efficacy of Antimicrobial Agents

Where the hydrophobic molecule is an antimicrobial compound, the present method may provide for an efficient method to deliver the antimicrobial compound to the target microorganism and thereby to reduce or inhibit growth of the microorganism. The efficiency of the antimicrobial may be measured by a minimum inhibitory concentration (MIC) measured in vitro. In some embodiments, the method reduces the MIC by 10% or more, e.g., 20% or more, 30% or more, 40% or more, including 50% or more, and in some embodiments, the by 99% or less, e.g., 95% or less, 90% or less, 80% or less, 70% or less, 60% or less, including 50% or less, compared to an appropriate control (e.g., the MIC of the antimicrobial compound uncomplexed to albumin tested in otherwise comparable conditions). In some cases, the method reduces the MIC of the antimicrobial compound by a percentage in the range of 10 to 99%, e.g., 20 to 95%, 20 to 90%, 30 to 80%, 40 to 70%, including 40 to 60%, compared to an appropriate control. In some cases, the MIC of the antimicrobial compound used in a complex with albumin according to a method of the present disclosure has the substantially the same MIC as the antimicrobial compound used under an appropriate control condition (e.g., compared to the MIC of the antimicrobial compound not complexed to albumin).

Methods of Determining the Presence of a Microorganism in a Sample

In some cases, the hydrophobic molecule is a compound with one or more detectable properties, e.g., a compound with detectable optical properties, that change significantly depending on intermolecular interactions, as described above, and the hydrophobic ligand-albumin complex may be used as a labeling reagent for labeling and detecting a microorganism in a sample, e.g., a clinical sample, with the hydrophobic ligand. The interaction of the metabolically active microorganisms in a sample with the albumin of the complex may result in changes in the sample that can be monitored, e.g., monitored optically. For example, in the baseline state, the hydrophobic molecule, e.g., lycopene, concentration may be substantially uniform throughout the glass vial, as may be expected if the albumin complex is truly in solution. As the metabolically active bacteria (that may have a concentration of protons on its surface) interacts with the albumin (which may have a negative surface charge), the albumin may form aggregates. The formation of these aggregates may result in optical or other changes in the sample, depending on the hydrophobic molecule complexed with the albumin, that can be monitored for the presence and/or amount of bacteria.

Thus, in general terms, a microorganism present in the sample may be detected by first delivering non-covalent complexes, each complex containing a non-covalent complex of a hydrophobic molecule and a single albumin protein, to the microorganism in the sample of interest, as described above; and then analyzing, e.g., measuring one or more properties, e.g., one or more intermolecular distance-dependent properties, of the sample to determine the presence of the microorganism. In some embodiments the intermolecular distance-dependent properties representative of the aggregate form of the hydrophobic molecule may indicate the presence of the microorganism in the sample; and intermolecular distance-dependent properties representative of the soluble or non-aggregate form of the hydrophobic molecule may indicate the absence of the microorganism in the sample.

The following are examples of aqueous solutions that find use in the present method of detecting a microorganism in sample:

0.6 µM lycopene/HSA, 1.2 µM β-carotene/HSA, 2 mL of 1×TSB, 0.02 mg/mL ascorbic acid, and 3.4 mL of PBS with an overall pH of 7.1;

1.5 µM lycopene/HSA, 2 mL of 1×TSB, 0.02 mg/mL ascorbic acid, and 3.4 mL of PBS with an overall pH of 7.5.

The sample tested for the presence of a microorganism by a method of the present disclosure may be any suitable sample, such as a body fluid sample, as long as the components of the sample do not substantially interfere with the labeling and detection of the microorganism. In some cases, the sample is a clinical sample, obtained from a healthy individual, or a patient suspected of having or diagnosed with a disease, e.g., an infectious disease. A suitable sample includes, without limitation, serum, plasma, blood, saliva, mucous, phlegm, cerebral spinal fluid, pleural fluid, tears, lactal duct fluid, lymph, sputum, cerebrospinal fluid, synovial fluid, urine, amniotic fluid, and semen, etc, and processed forms thereof. In some cases, the sample is processed to remove pigmented components, e.g., to remove red blood cells from blood, using any suitable method. In some cases, the sample includes a known amount of a known microorganism. The sample may include any suitable amount of microorganisms. In some cases, the sample includes 1 colony forming units (CFU)/mL or more, e.g., 5 CFU/mL or more, 10 CFU/mL or more, 100 CFU/mL or more, 1,000 CFU/mL or more, $10^4$ CFU/mL or more, $10^5$ CFU/mL or more, including $10^6$ CFU/mL or more, and in some embodiments, includes $10^{10}$ CFU/mL or fewer, e.g., $10^9$ CFU/mL or fewer, $10^8$ CFU/mL or fewer, $10^7$ CFU/mL or fewer, $10^6$ CFU/mL or fewer, including $10^5$ CFU/mL or fewer of the microorganisms. In some embodiments, the sample includes a concentration of the microorganisms in the range of 1 to $10^{10}$ CFU/mL, e.g., 1 to $10^9$ CFU/mL, 1 to $10^8$ CFU/mL, 1 to $10^7$ CFU/mL, 1 to $10^6$ CFU/mL, 5 to $10^5$ CFU/mL, 10 to $10^4$ CFU/mL, including 10 to $10^3$ CFU/mL. In some cases, it is not known whether or at what concentration microorganisms are present in the sample.

The intermolecular distance-dependent property of the hydrophobic molecule(s) may be any suitable property. In some cases, the intermolecular distance-dependent property is an optical property, such as, but not limited to, optical absorbance, Raman scattering, fluorescence, etc. In some cases, the intermolecular distance-dependent property is the peak absorbance at optical absorption band. In other cases, the property is the peak of a Raman band. The optical intermolecular distance-dependent property may be measured using any suitable method. In some cases, measuring includes using a Raman spectrometer that resonantly enhances the Raman scattering peak from a hydrophobic molecule, e.g., lycopene (for instance, by using a 532 nm wavelength). In some cases, measuring includes using a UV-Vis absorption spectrometer (or any other instrument).

In some cases, the measuring includes using a fluorescent microscope, fluorescence spectrometer, or fluorimeter.

In some cases, the method includes measuring the magnitude of an optical property, e.g., a Raman peak height, absorbance at a wavelength, of the sample. For example, a sample labeled with a carotenoid/albumin complex, e.g., a lycopene/HSA complex, may have a resonant Raman peak height upon illumination by a 532 nm wavelength light that is negatively correlated with the concentration of a microorganism in the sample. In some cases, the measuring is performed as soon as about 5 minutes, e.g., as soon as about 10 minutes, after starting the incubation of the microorganism with the aqueous solution containing the hydrophobic ligand-albumin complex.

In some cases, the presence or absence of the microorganism in a sample is determined by measuring a spatial distribution of or temporal change in an optical property of the hydrophobic molecule, or aggregated form thereof, where the optical property is intermolecular distance-dependent, to obtain a spatial profile or temporal profile, respectively, of the optical property of the sample labeled with the hydrophobic ligand-albumin complex.

In some cases, the method includes measuring the rate of change in an optical property of the sample, e.g., rate of change of the height of a Raman peak generated by 532 nm light illumination of a sample labeled with a carotenoid/albumin complex, at a predetermined (or fixed) spatial location along the vial or vessel in which the assay is being performed. The predetermined spatial location may be any suitable location along the assay vessel. In some cases, the predetermined spatial location is a position along a vertical dimension of the vessel. The predetermined spatial location along the vertical dimension of the vessel may be at a level above where albumin aggregated due to microorganisms segregate and accumulate. In some cases, the predetermined location is at a distance in the range of about 5 to about 10 mm, about 10 to about 15 mm, about 15 to about 20 mm, about 20 to about 25 mm, about 25 to about 30 mm, about 30 to about 35 mm, about 35 to about 40 mm, about 40 to about 45 mm, about 45 to about 50 mm, about 50 to about 55 mm, or about 55 to about 60 mm from the bottom inner surface of the assay vessel.

In some cases, the method includes measuring the spatial distribution of an optical property, e.g., the height of a Raman peak, along an axis of the assay vessel at a predetermined time after mixing the microorganisms with the aqueous solution containing the hydrophobic ligand-albumin complex. In some cases, the optical property is measured along the vertical axis. In some cases, the optical property is measured across locations in the range of about 0 to about 60 mm, e.g., about 0 to about 50 mm, about 0 to about 40 mm, including about 0 to about 30 mm from the bottom inner surface of the assay vessel.

The spatial distribution of or temporal change in an optical property of the hydrophobic molecule, or aggregated form thereof, may be at any suitable time after beginning the assay. In some cases, the optical property is measured at a time point in the range of 1 min to 6 hrs, e.g., 3 min to 3 hrs, 3 min to 1 hr, 3 min to 30 min, including 1 min to 5 min, after start of incubation of the microorganisms in the aqueous solution containing the hydrophobic ligand-albumin complex.

The present method of determining the presence or absence of a microorganism in a sample may be a rapid method. In some embodiments, the method determines the presence or absence of microorganisms in a sample in at most 12 hrs, e.g., at most 6 hrs, at most, 3 hrs, at most 2 hrs, including at most 1 hours, from first obtaining the sample, e.g., clinical sample.

Methods of Measuring the Minimal Inhibitory Concentration of Antimicrobial Agents The present methods may also find use in determining the susceptibility of a microorganism for an antimicrobial. The method may include combining microorganisms with a plurality of aqueous solutions that each contain different concentrations of an antimicrobial agent, in a concentration range that is expected to cause a concentration-dependent change in the rate of growth of the microorganisms, ranging from decreased or no growth to normal growth (e.g., as determined by growth in the absence of the antimicrobial agent). Thus the aqueous solution may contain a nutrition source that supports growth of the microorganism, in addition to any suitable additional components, as described above. The highest concentration of the antimicrobial at which there is at most no growth of the microorganism may correspond to the MIC of the antimicrobial agent for the microorganism.

The microorganism may be obtained from any suitable source. In some cases, the microorganism is obtained from a clinical sample, e.g., from blood, saliva, mucus, etc., of an individual infected with the microorganism. In some cases, the MIC for the microorganism is not known with respect to the antimicrobial agent. In some cases, the method includes growing the microorganism to provide sufficient numbers for dividing into multiple aliquots and testing multiple concentrations of the antimicrobial agent.

The present method of determining the MIC of an antimicrobial agent may be a rapid method. In some embodiments, the present method determines the MIC of an antimicrobial agent in at most 12 hours, e.g., at most 10 hours, at most 8 hours, at most 6 hours, at most 5 hours, including at most 4 hours. In some cases, the method is a high-throughput method of determining the MIC of multiple antimicrobial agents for one or more microorganisms. Any suitable number of antimicrobial agents may be tested. In some cases, the number of antimicrobial agents tested is 2 or more, e.g., 3 or more, 5 or more, 10 or more, 20 or more, 50 or more, 100 or more, including 1,000 or more, and in some embodiments, is 100,000 or less, e.g., 10,000 or less, 1,000 or less, including 100 or less.

Methods of Dispersing Albumin Aggregates

Also provided herein is a method of dispersing an aggregate of albumin. The method may include suspending the albumin aggregate in a solution having a pH above 8.0, e.g., 8.2 or higher, 8.4 or higher, 8.6 or higher, 8.8 or higher, including 9.0 higher, and sonicating the suspension to disperse the aggregate. In some cases, the albumin aggregate is an aggregate of hydrophobic ligand-albumin complexes, as described above. The pH of the solution may in some cases be 10.0 or lower, e.g., 9.5 or lower, including 9.0 or lower. In some embodiments, the pH of the solution is in the range of 8.2 to 10.0, e.g., 8.2 to 9.5, including 8.2 to 9.0.

The sonicating may be performed for any suitable amount of time. In some cases, the sonication is performed for 5 min or more, e.g., 10 min or more, including 15 min or more, and in some cases, is performed for 60 min or less, e.g., 45 min or less, including 30 min or less. In some embodiments, the sonicating is performed for a duration in the range of 5 to 60 min, e.g., 5 to 45 min, including 10 to 30 min.

In some cases, the albumin aggregate may be formed by storing a solution of dissolved albumin at a temperature below 37° C., e.g., 35° C. or less, 30° C. or less, 20° C. or less, 10° C. or less, including 5° C. or less, and may be formed by storing at a temperature of 0° C. or more, e.g., 5° C. or more, 10° C. or more, 15° C. or more, including 20° C. or more. In some embodiments, the albumin aggregate is formed by storing a solution of dissolved albumin at a temperature in the range of 0 to 35° C., e.g., 0 to 30° C., 0 to 20° C., including 0 to 10° C.

Kits

Also provided herein is a kit that includes a composition containing a non-covalent complex of a hydrophobic molecule and an albumin protein, as described herein. In some cases, the composition is an aqueous composition, or a substantially dry composition. In some cases, the kit further includes a buffer that may or may not include one or more additional components (e.g., antioxidant, nutrition source, etc.), as described herein.

In some cases, the present kit includes instructions for using a composition including a non-covalent complex of a hydrophobic molecule and an albumin protein of the present disclosure. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

Components of a subject kit can be in separate containers; or can be combined in a single container.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-59 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A method of forming a solution comprising a non-covalent complex of a hydrophobic molecule and an albumin protein, the method comprising:
dissolving the hydrophobic molecule in:
i) a first organic solvent comprising a $C_3$-$C_5$ ketone; or
ii) a combination of the first organic solvent and a second organic solvent in a ratio of from about 0.001:1 to about 1000:1 v/v,
to provide a first solution;
combining the first solution with a second solution to provide a third solution, wherein the second solution is an aqueous solution comprising an albumin protein; and
removing the first organic solvent or the combination of the first organic solvent and the second organic solvent from the third solution to provide a fourth solution, wherein the fourth solution is an aqueous solution comprising a non-covalent complex of the hydrophobic molecule and a single albumin protein.

2. The method of 1, wherein the $C_3$-$C_5$ ketone is acetone.

3. The method of 1 or 2, wherein the hydrophobic molecule is dissolved in the combination of a first organic solvent and a second organic solvent, and wherein the ratio of the first organic solvent and the second organic solvent is in the range of about 1:1 to about 5:1.

4. The method of 3, wherein the hydrophobic molecule is dissolved in the combination, and wherein the combination comprises the first organic solvent and the second organic solvent in a ratio of about 2:1.

5. The method of any one of 1-4, wherein the hydrophobic molecule is dissolved in the combination, and wherein the method comprises:
dissolving the hydrophobic molecule in the second organic solvent, to provide a fifth solution; and
combining the fifth solution with the $C_3$-$C_5$ ketone to provide the first solution prior to combining the first solution with the second solution.

6. The method of any one of 1-5, wherein the removing is performed by evaporation.

7. The method of any one of 1-6, wherein the method comprises contacting a microorganism comprising a cell wall with an aqueous solution comprising the non-covalent complex of the hydrophobic molecule and a single albumin protein, wherein the hydrophobic molecule functionally associates with the microorganism.

8. The method of 7, wherein the microorganism is a pathogenic microorganism.

9. The method of 7 or 8, wherein the contacting occurs in vitro.

10. The method of 7 or 8, wherein the contacting occurs in vivo.

11. The method of any one of 1-10, wherein the hydrophobic molecule is a carotenoid.

12. The method of 11, wherein the carotenoid is a carotene.

13. The method of 12, wherein the carotene is lycopene or β-carotene.

14. The method of any one of 1-10, wherein the hydrophobic molecule is an antimicrobial.

15. The method of 14, wherein the antimicrobial is an antibacterial.

16. The method of 14, wherein the antimicrobial is an antifungal.

17. The method of any one of 13-16, wherein the antimicrobial has increased efficacy when provided in the non-covalent complex relative to the antimicrobial in an un-complexed state, or when the antimicrobial is incorporated into other delivery systems.

18. The method of any one of 1-10, wherein the hydrophobic molecule is a pharmacologically active agent.

19. The method of 18, wherein the pharmacologically active agent is selected from an anti-cancer drug, an anti-viral drug, and a cardiovascular drug.

20. The method of any one of 1-19, wherein the albumin protein is a human serum albumin protein.

21. The method of any one of 1-19, wherein, the method does not comprise the use of a potassium phosphate containing reagent.

22. A method of delivering a hydrophobic molecule to the cell wall of a microorganism, the method comprising contacting a microorganism comprising a cell wall with an aqueous solution comprising a non-covalent complex of a hydrophobic molecule and a single albumin protein, wherein the hydrophobic molecule functionally associates with the microorganism.

23. The method of 22, wherein the microorganism is a pathogenic microorganism.

24. The method of 22 or 23, wherein the contacting occurs in vitro.

25. The method of 22 or 23, wherein the contacting occurs in vivo.

26. The method of any one of 22-25, wherein the hydrophobic molecule is a carotenoid.

27. The method of 26, wherein the carotenoid is a carotene.

28. The method of 27, wherein the carotene is lycopene or β-carotene.

29. The method of any one of 22-25, wherein the hydrophobic molecule is an antimicrobial.

30. The method of 29, wherein the antimicrobial is an antibacterial.

31. The method of 29, wherein the antimicrobial is an antifungal.

32. The method of any one of 22-31, wherein the albumin protein is a human serum albumin protein.

33. A method for determining the presence or absence of a microorganism in a sample, the method comprising:
i) contacting the sample with an aqueous solution comprising a plurality of non-covalent complexes, each non-covalent complex comprising a hydrophobic molecule and a single albumin protein, wherein the hydrophobic molecules are detectable and functionally associate with a microorganism when present in the sample;
ii) detecting one or more properties of the hydrophobic molecules; and
iii) determining that the microorganism is present or absent in the sample based on the detecting.

34. The method of 33, wherein the hydrophobic molecules have one or more intermolecular distance-dependent properties, wherein the detecting comprises measuring in the sample one or more profiles of the one or more intermolecular distance-dependent properties, and wherein the determining comprises determining that the microorganism is present when the one or more profiles indicates the presence of aggregates of the hydrophobic molecule in the sample, or determining that the microorganism is absent when the one or more profiles indicates the absence of aggregates of the hydrophobic molecule in the sample.

35. The method of any one of 33-34, wherein the microorganism is a pathogenic microorganism.

36. The method of 34 or 35, wherein the one or more intermolecular distance-dependent properties are one or more optical properties.

37. The method of 36, wherein the one or more intermolecular distance-dependent properties comprise an optical absorption band and/or a Raman band.

38. The method of 36, wherein the one or more intermolecular distance-dependent properties comprise Förster resonance energy.

39. The method of any one of 33-37, wherein the hydrophobic molecule is a carotenoid.

40. The method of 39, wherein the carotenoid is a carotene.

41. The method of 40, wherein the carotene is lycopene or β-carotene.

42. The method of any one of 34-41, wherein the one or more profiles comprises a) a temporal profile at a fixed spatial point, and/or b) a spatial profile at a fixed time point, of the height of Raman scattered light for the sample obtained by analyzing the sample with a spectrometer,
and wherein the determining comprises determining the presence or absence the microorganism in the sample based on the height of one of a plurality of characteristic Ramen peaks in the spatial profile, and/or the rate of change of one of the plurality of characteristic Raman peaks in the temporal profile, relative to a corresponding set of reference profiles.

43. The method of any one of 33-42, wherein the albumin protein is a human serum albumin protein.

44. A method for determining the presence or absence of a microorganism in a sample, the method comprising:
contacting the sample with an aqueous solution comprising a non-covalent complex of a hydrophobic molecule and a single albumin protein, wherein the hydrophobic molecule is a carotenoid and functionally associates with a microorganism, when present in the sample;
illuminating the sample with a broadband light source;
collecting and analyzing with a spectrometer light transmitted through the sample, wherein a temporal profile at a fixed spatial point, or a spatial profile at a fixed time point, of the height of a UV-Vis absorption peak is analyzed, and wherein
the height of one of a plurality of characteristic Raman peaks is used as an indicator when compared with a set of control values, or
the rate of change of one of the plurality of characteristic Raman peaks is used as an indicator, of the presence of the detectable hydrophobic molecule bound to the microorganism in the sample.

45. The method of 44, wherein the microorganism is a pathogenic microorganism.

46. The method of 44 or 45, wherein the carotenoid is a carotene.

47. The method of 46, wherein the carotene is lycopene or β-carotene.

48. The method of any one of 44-47, wherein the albumin protein is a human serum albumin protein.

49. A composition comprising:
an aqueous solution comprising a non-covalent complex of a hydrophobic molecule and a single albumin protein.

50. The composition of 49, wherein the hydrophobic molecule is a carotenoid.

51. The composition of 50, wherein the carotenoid is a carotene.

52. The composition of 51, wherein the carotene is lycopene or β-carotene.

53. The composition of 49, wherein the hydrophobic molecule is an antimicrobial.

54. The composition of 53, wherein the antimicrobial is an antibacterial.

55. The composition of 53, wherein the antimicrobial is an antifungal.

56. The composition of 53, wherein the hydrophobic molecule is a pharmacologically active agent.

57. The composition of 56, wherein the pharmacologically active agent is selected from an anti-cancer drug, an anti-viral drug, and a cardiovascular drug.

58. The composition of any one of 49-57, wherein the albumin protein is a human serum albumin protein.

59. A method to disperse aggregates of albumin, the method comprising:
suspending the aggregate in a solution with a pH above 8.0 to provide a suspension; and/or
sonicating the suspension, wherein the aggregate is dispersed.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Materials and Methods

The following material and methods were used in the Examples, where applicable.

Reagents: The following reagents were purchased from commercial sources listed as follows: Acetone & hexane: Macron; Ethyl acetate and ethanol: EMD; Pooled human serum: Innovative Research Inc.; Human Serum Albumin HSA: Gemini Bio Products; Lycopene: Sigma-Aldrich; Tryptic Soy Broth TSB powder: Becton Dickinson; Synthetic defined dropout media powder SDM: Sunrise Science Products. 1× and 4×SDM solutions are 27.49 and 109.96 grams, respective, of SDM powder in 1 L of DI water.

Pathogen Stock Solution: An overnight culture of a known isolate of a particular microorganism in a rich medium (TSB) was centrifuged into a pellet, passaged once for 3 hours, centrifuged into a pellet again and then re-suspended in PBS. The optical density of the isolate was characterized, and adjusted by adding more PBS as necessary until OD=0.25 at 600 nm, which was treated as $10^8$ CFU/mL (upon checking with an overnight culture on a plate, the actual concentration was generally found to be within 2× of the inferred concentration). Serial dilutions was then performed to prepare stock solutions in PBS at $10^1$-$10^8$ CFU/mL.

Instrumentation: For the UV-Vis absorption spectroscopy, METASH Visible Spectrophotometer (en(dot)metash(dot)com/ProductShow(dot)asp?ID=148) was used with a USB interface. For the circular dichroism measurements, A VIV Circular Dichroism Spectrometer, Model 62 DS was used. For the Raman and fluorescence measurements, a commercial spectrometer with a 532 nm/100 mW laser, and a CCD that is cooled to −50° C. (vendor: Enwave Optronics, now TSI Inc) were used.

Example 2

β-Carotene Incorporated into Albumin

Aqueous solutions of β-carotene incorporated into human serum albumin (and which can be used to incorporate into other albumins) were prepared using the following steps: (1) To a 15 mL-centrifuge tube, 23 mg of β-carotene (extracted from carrots using hexane; followed by removal of hexane using evaporation) and 12 mL of acetone were added. The mixture was vortexed for 1 min and sonicated for 5 min. The mixture was then centrifuged for 5 min at 4000 RPM, and the yellow solution on top is decanted off and used for the subsequent steps. (2) To a 500 mL-round bottom flask, 1.0 gm of commercial human serum albumin HSA, 145 mL of commercial PBS buffer, and 0.5 mL of vitamin C PBS buffer solution (10 mg/mL) were added. The mixture was shaken well and sonicated for 5 min and used in the next step. (3) After adding a magnetic stirring bar, the HSA solution was stirred vigorously, and β-carotene/acetone solution was added slowly via a pipette. After 12 mL of this solution was added, the UV-Vis absorption spectrum of the resulting dark yellow solution was monitored. Typically, the absorbance was observed at 456 nm $A_{456}$=2.09. After adding 20 mL of PBS buffer, the resulting mixture was concentrated using a rotavapor in order to remove all acetone (no bubbling was observed during this process and a significant amount of water was condensed on to the trap surface). The resulting yellow solution was filtered through a membrane (200 nm). The UV-Vis spectrum of the filtered yellow solution was monitored and recorded; in this case, the typical $A_{456}$=1.50 and final volume was 170 mL. Because β-carotene was insoluble in water, and because all organic solvents had been removed in the final step, the β-carotene was incorporated into the human serum albumin. Also, based on the UV-Vis absorbance profiles at >600 nm, it was concluded that the albumin was present in monomeric form (aggregation of albumin results in enhanced Rayleigh scattering, which could be detected in the UV-Vis absorbance above 600 nm). Based on the extinction coefficient at 456 nm as 158,000 $M^{-1}$ $cm^{-1}$ (obtained through hexane extraction and UV absorption in hexane with the known extinction coefficient as 144,000 $M^{-1}$ $cm^{-1}$ at 446 nm), the concentrations were estimated as [β-carotene]=1.5/158,000=9.49 uM, [HSA]=1000/66000/0.170=90 uM. [HSA]/[β-carotene]=90/9.49=9.48.

Example 3

Lycopene Incorporated into Albumin

Solutions of lycopene in human serum albumin were prepared using the following steps. Lycopene acetone solution: To a 15 mL-centrifuge tube, 28 mg lycopene and 14 mL acetone were added. The mixture was vortexed for 1 min, sonicated for 5 min and centrifuged for 5 min at 4000 RPM. The reddish solution on top was decanted off and used for the subsequent steps. HSA/PBS buffer solution: To a 500 mL-round bottom flask, 0.2 g HSA, 200 mL PBS buffer and 0.5 mL ascorbic acid/PBS solution mixture (10 mg/mL ascorbic acid concentration) were added. The mixture was shaken well and sonicated for 5 min. Lycopene/HSA complex solution: After adding a magnetic stirring bar, the HSA solution was vigorously stirred, and 16 ml of the lycopene acetone solution was added slowly using a pipette. The UV-Vis absorption spectra of the resulting reddish solution was monitored, with a typical absorbance $A_{476}$=1.3031, and acetone was removed using a rotavapor. The resulting reddish solution was filtered through a 0.2 µm membrane, and typical absorbance was $A_{476}$=0.959, and the typical final volume was about 200 mL. Based on the calculated extinction coefficient at 476 nm as 155,500 $M^{-1}$ $cm^{-1}$ (obtained through hexane extraction and UV absorption in hexane with the known extinction coefficient as 200,000 $M^{-1}$ $cm^{-1}$ at 470 nm), [Lycopene]=0.959/155,5000=6.16 µM, [HSA]=1000/66000/0.203=75 µM. [HSA]/[Lycopene]=75/6.16=12.17.

Figure 5A:
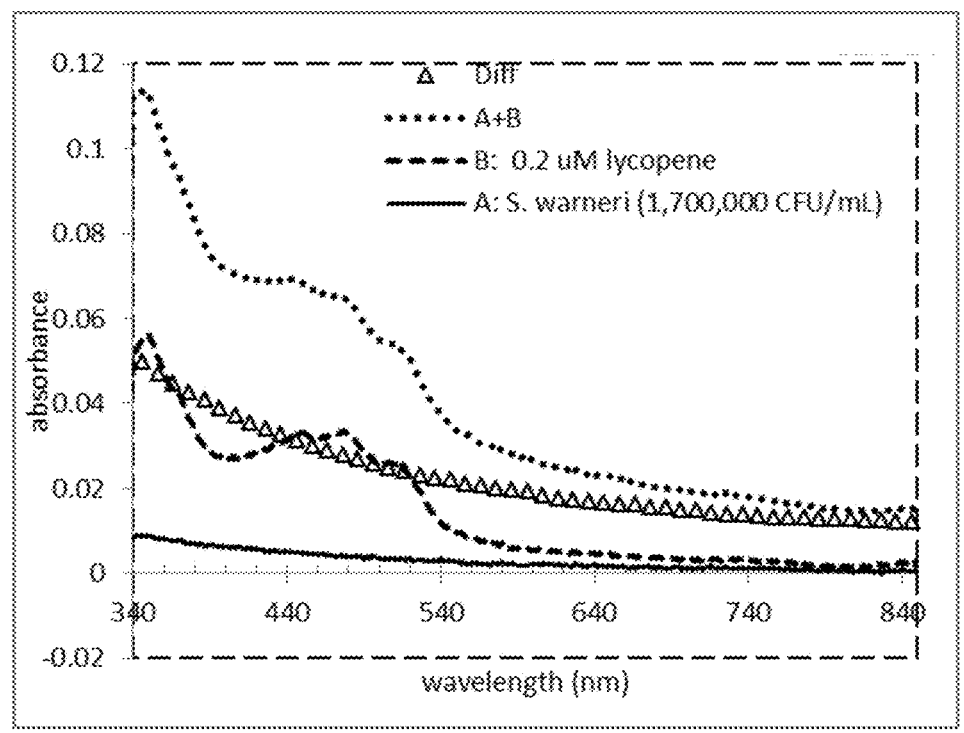
FIG. 5A is a graph showing UV-Vis absorbance spectra of lycopene/HSA in the presence or absence of *Staphylococcus warneri*, according to embodiments of the present disclosure.
Figure 5B:
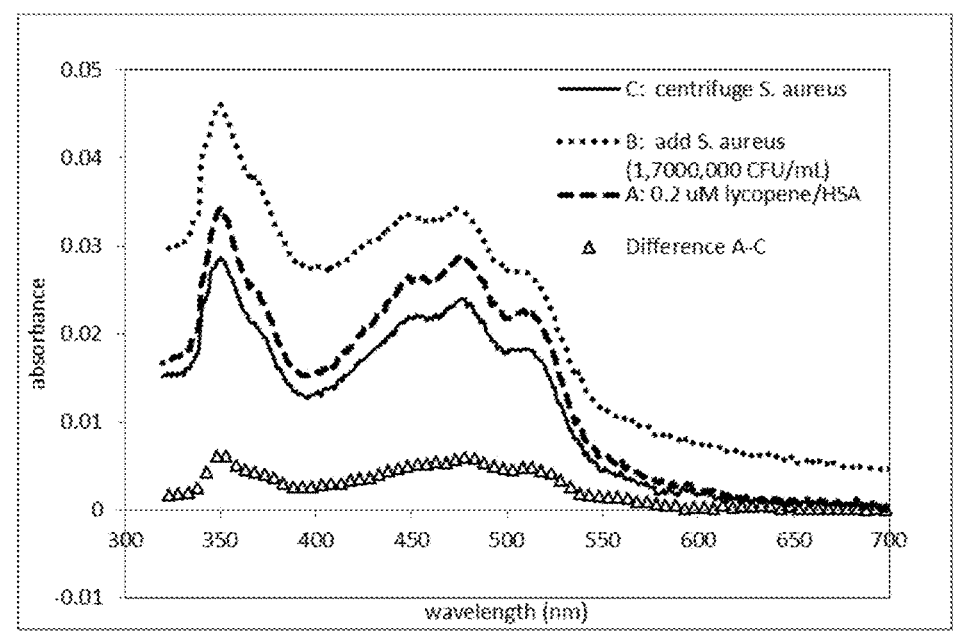
FIG. 5B is a graph showing UV-Vis absorbance spectra of lycopene/HSA in the presence or absence of *Staphylococcus aureus*, according to embodiments of the present disclosure.

Binding experiments of FIG. 5B: To three 15 mL centrifuge tubes, 200 µL of 4×SDM, 125 µL, or 250 µL or 500 µL (for the three tubes) of 9.8 µM Lycopene/HSA solution, and 5575 µL or 5450 µL or 5200 µL of PBS (for the three tubes) were added. Each centrifuge tube was vortexed for 1 min and the solution in each tube was analyzed in a UV-Vis absorbance spectrometer using 1 cm cuvettes. This UV-Vis profile was marked as the "HSA/Lycopene only" spectrum. The entire solution was then transferred back to the original centrifuge tube. To these centrifuge tubes, 100 µL of a pathogen suspended in PBS were added at $10^8$ CFU/mL. The final concentration of the pathogen in each tube is $1.7 \times 10^6$ CFU/mL. For "control" samples, 100 µL of PBS were added without any microorganism. The centrifuge tubes were wrapped in Al foil and vortexed for 1 min and incubated with a loose cap in a 37° C. shaker for 30 min. The tubes were then vortexed again for 1 min, and analyzed in the UV-Vis spectrometer. This UV-Vis profile was marked as the "add bacteria" spectrum. The entire solution was then transferred back to the original tube and centrifuged for 5 min at 4,000 RPM. The supernatant from the centrifuge tubes was carefully aliquoted into the cuvette and analyzed again in the UV-Vis spectrometer. This UV-Vis profile was marked as the "after centrifuge" spectrum.

Example 4

Amphotericin B Incorporated into Albumin

Amphotericin B is slightly soluble in methanol and insoluble in acetone. To form a complex of amphotericin B with albumin, a solution of Amphotericin B in methanol was diluted in acetone with a 1:2 dilution (dilutions of less than 1:2 did not result in the incorporation of significant amounts of Amphotericin B into albumin). The acetone/methanol solution was mixed with the aqueous albumin solution, and the acetone and methanol removed from the mixture in a rotavapor. The ligand transferred to albumin (FIG. 3).

Figure 3:
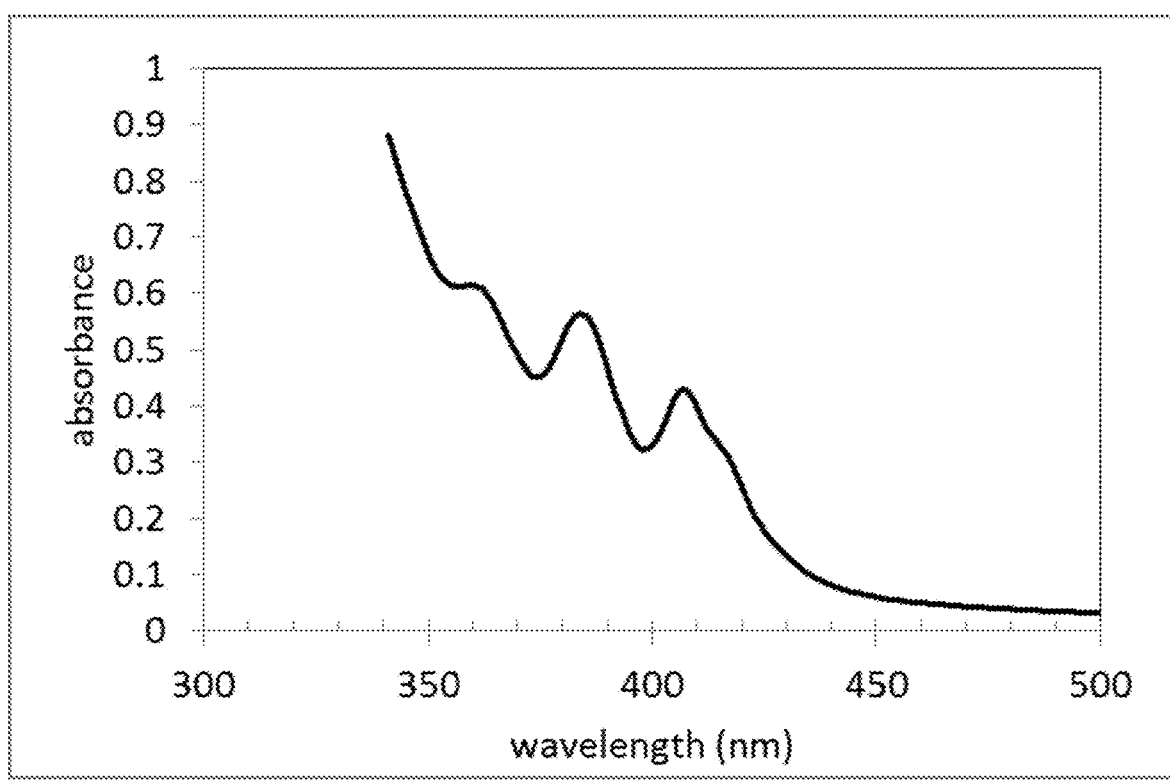
FIG. 3 is a graph showing the UV-Vis spectrum of an aqueous solution of Amphotericin-B incorporated into bovine serum albumin (BSA), according to embodiments of the present disclosure.

FIG. 3. UV-Vis spectrum of an aqueous solution of Amphotericin-B incorporated into bovine serum albumin (BSA).

Example 5

Camptothecin Incorporated into Albumin

The anticancer therapeutic agent camptothecin (CPT) dissolves in dichloromethane and small amount of methanol. To form a complex of CPT with albumin, 30 mg of CPT was dissolved in 75 mL of dichloromethane and 10 mL of methanol. The resulting dichloromethane/methanol CPT solutions were diluted by adding 2 times of acetone in volume (once again, dilutions of less than 2 parts acetone did not result in the formation of albumin-CPT complexes). The clear acetone/dichloromethane/methanol CPT solution was added into the aqueous Albumin solution, and the CPT formed a complex with the albumin as the acetone and dichloromethane was removed with a rotavapor (FIG. 4).

Figure 4:
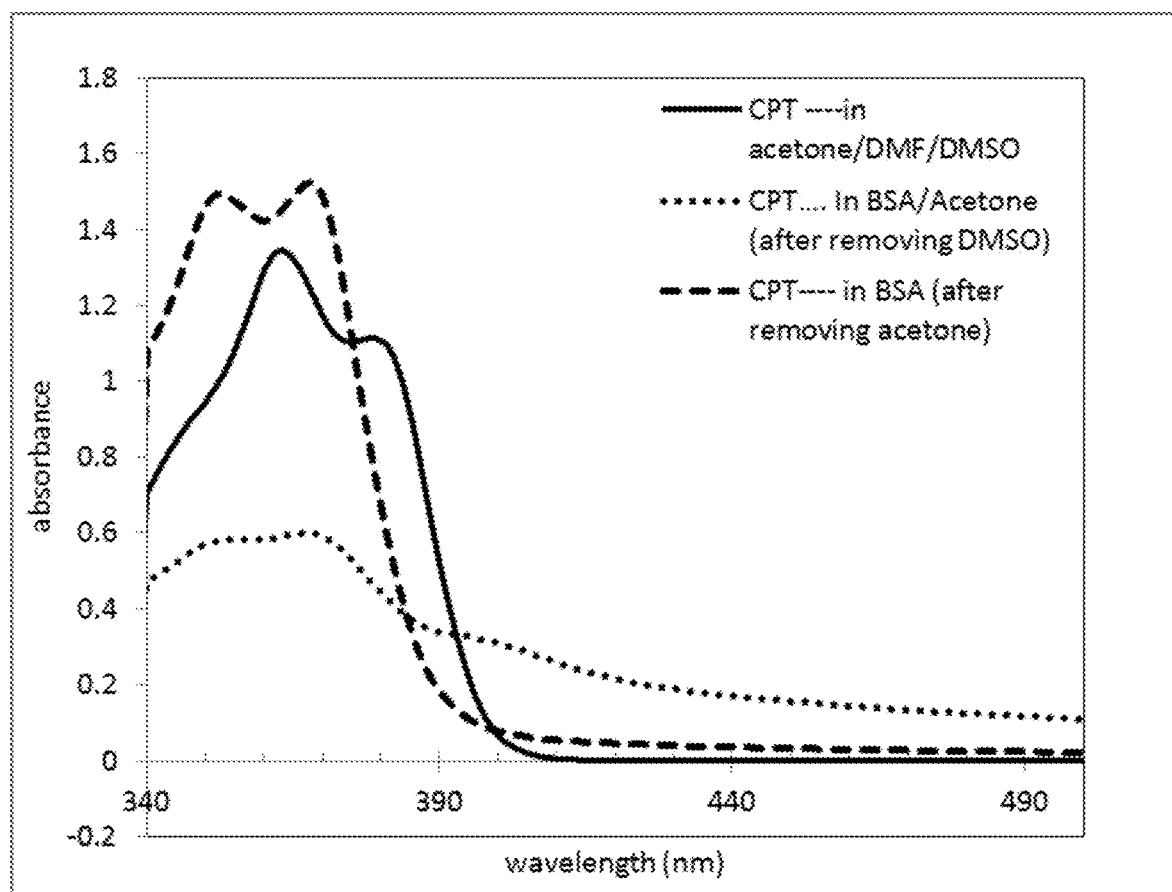
FIG. 4 is a graph showing the UV-Vis spectra of an aqueous solution of Camptothecin (CPT) incorporated into bovine serum albumin (BSA), according to embodiments of the present disclosure.

FIG. 4. UV-Vis spectrum of an aqueous solution of Camptothecin incorporated into bovine serum albumin (BSA).

Example 6

The Effect of Organic Solvent in the Production of Hydrophobic Ligand-Albumin Complexes The effect of the organic solvent used in the preparation of a hydrophobic ligand-albumin complex was tested. Several pure volatile and water soluble organic solvents such as terahydrofuran, methanol, ethanol, and acetone were tested. Of these, only acetone worked; for other solvents, when the solvent was removed, the hydrophobic ligand precipitated out instead of transferring to albumin.

Several non-volatile solvents, such as DMSO and DMF (boiling point >150° C.), which were removed with a dialysis bag (molecular weight cutoff of 1 KDa), were also tested. However, the hydrophobic ligand precipitated out instead of transferring to albumin. Without intending to be bound by any particular theory, acetone may be effective as a transfer agent due to a particular combination of properties (solubility parameter, miscibility with water, presence of polar groups, and the ability to alter albumin conformation) that makes it particularly suitable for this purpose.

Example 7

Reconstituting Freeze Dried Hydrophobic Ligand-Albumin Complexes

The effect of freeze drying on hydrophobic ligand-albumin complexes was tested. Lycopene in HSA was prepared as described, freeze dried into sheets, and the dried powder resuspended in solution, and the pH of the solution raised above 8. The resuspension was further sonicated using an 800 W sonicator for 10 minutes. The UV-Vis spectrum of the solution after sonication was nearly identical to the starting solution (FIG. 2).

Figure 2:
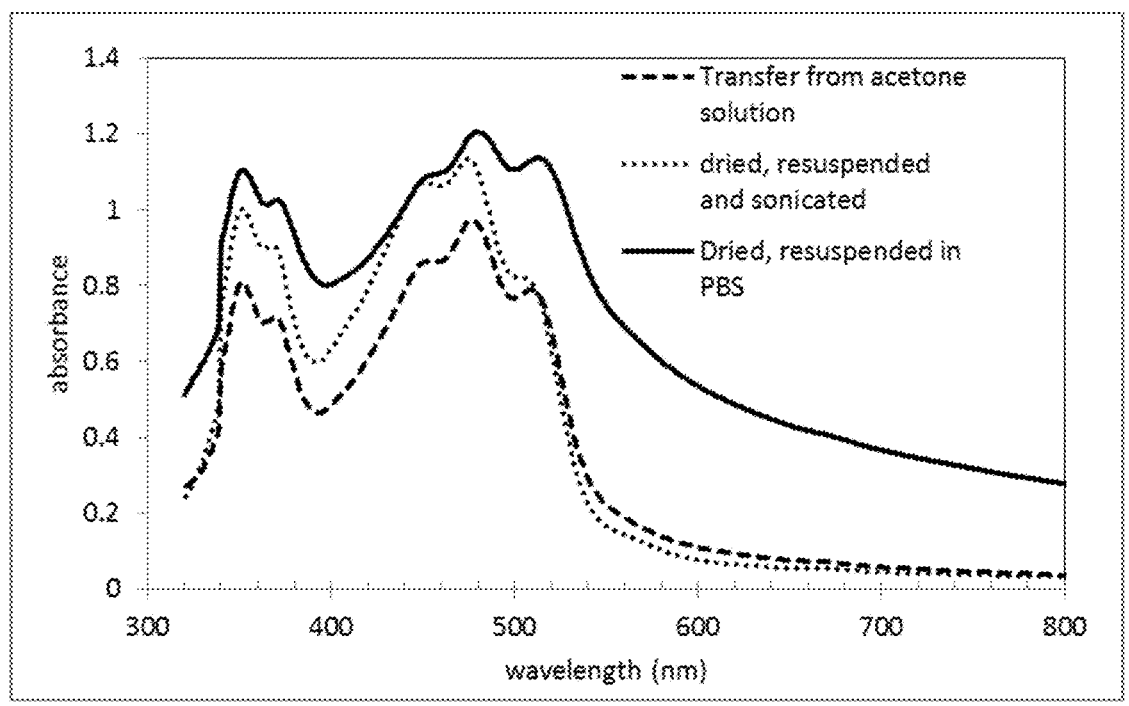
FIG. 2 is a graph showing an ultraviolet-visible (UV-Vis) spectrum of lycopene in HSA in an aqueous solution as it is first formulated by transferring from acetone, compared to the spectrum when the lycopene in HSA is dried and resuspended in water, and when the water suspension is sonicated using an 800 W sonicator for 10 minutes, according to embodiments of the present disclosure.

FIG. 2. UV-Vis spectrum of lycopene in HSA in an aqueous solution, as prepared, or freeze dried and resuspended, with and without sonication.

Example 8

Optical Changes in Lycopene Optical Spectrum Due to Aggregation

In most chromophores, changes in the chromophore concentration do not change the chromophores color—the absorption spectrum does not shift to lower, or higher, wavelengths. However, in some chromophores, optical exchanges come into play when the concentration of the chromophore increases beyond a critical level, and two adjacent chromophores can indulge in various optical interactions.

Figure 11:
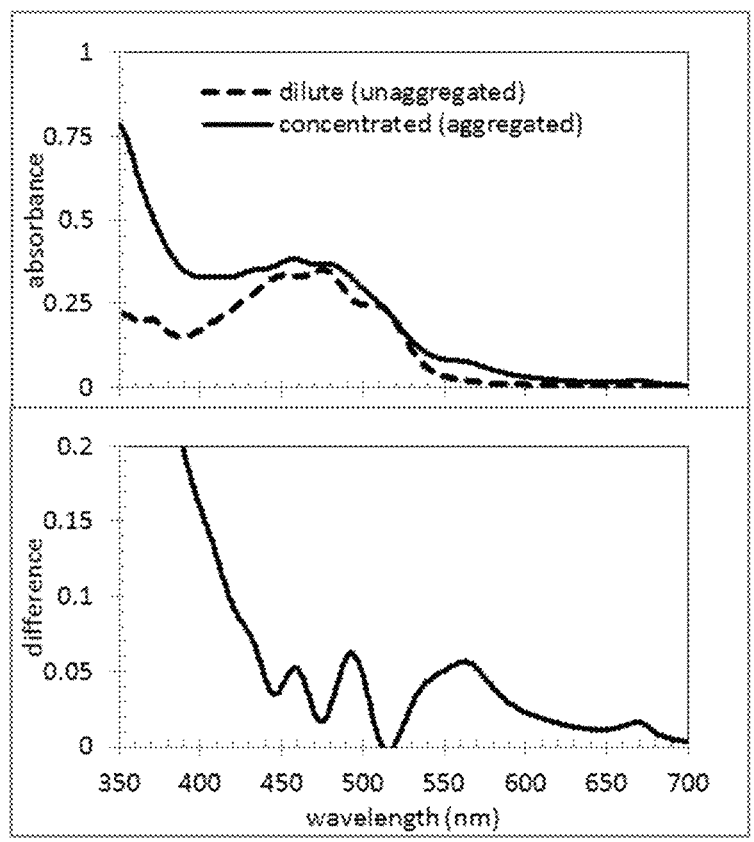
FIG. 11 is a collection of graphs showing UV-Vis absorption spectra of two lycopene solutions in hexane.

The absorption spectrum of lycopene was compared in dilute and concentrated forms. In dilute form, absorption spectrum of lycopene had three main peaks at 510, 480 and 450 nm, while in concentrated form, an additional absorption band at 670 nm and 565 nm were observed (FIG. 11). This may be due to formation of hydrophobic pockets that have a very different optical signature as a result of interaction between molecules in lycopene aggregates formed in a concentrated solution. Further, the creation of the red shifted absorption bands was accompanied by a redistribution of available vibrational states, i.e., the shape of the 450-510 nm triplet changes.

FIG. 11. UV-Vis absorption spectrum of two lycopene solutions in hexane. When care is taken to ensure that they remain in the dilute form, (presumably, when there are no lycopene aggregates), the spectrum was dominated by a triplet between 450 and 510 nm. In concentrated solutions (presumably, when aggregates are formed) that are subsequently diluted to about the same level as the dilute solution, there were additional absorption bands at 670, and 565, with potentially a weaker band at 530 nm. Also, the distribution of vibrational energies in the 450-510 nm triplet have changed.

Figure 12:
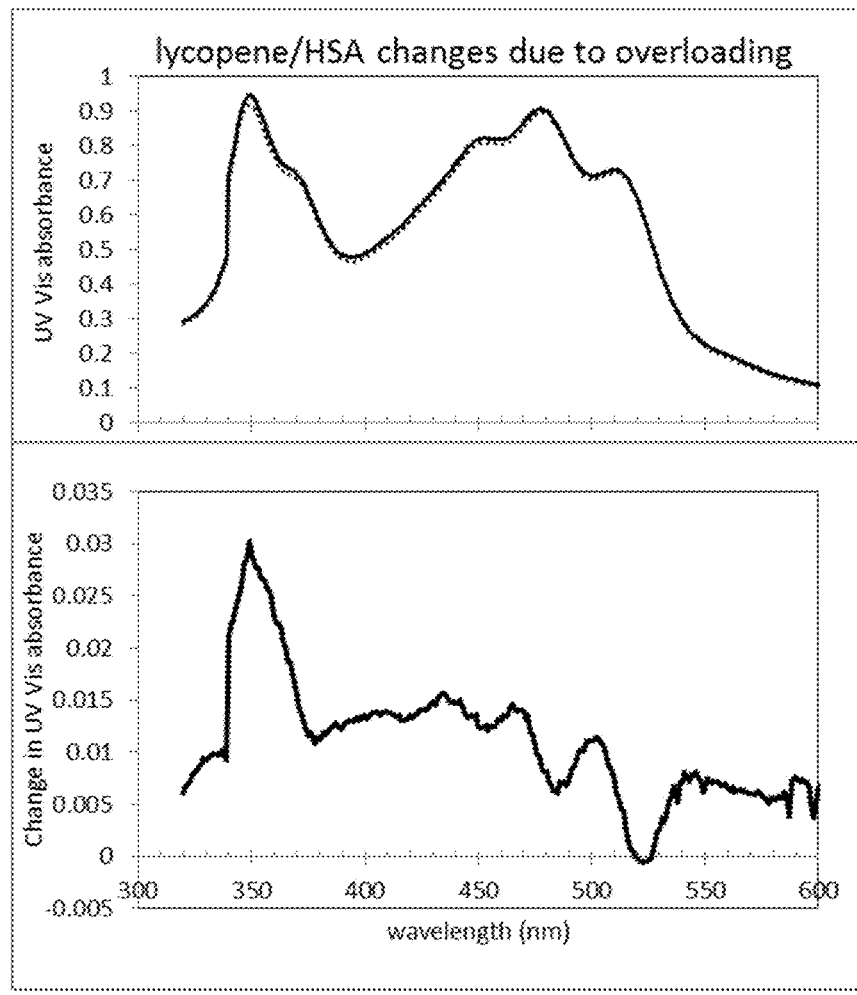
FIG. 12 is a collection of graphs showing changes in the UV-Vis absorption spectrum of overloaded lycopene/HSA upon addition of HSA.

A similar result was obtained for lycopene incorporated into the binding sites in HSA, as depicted in FIG. 12. HSA was added to a solution containing HSA bound at both of the 2 possible binding sites (Sudlow I and II) by lycopene. The difference spectrum showed a red shifted peak at 540 nm (FIG. 12). This suggests that the binding sites can potentially coordinate to enable some lycopene-lycopene interaction. Addition of new HSA may have redistributed the lycopene from Sudlow II to the newly added HSA (thereby reducing the aggregation). This absorption band is interesting because it affords the possibility of a simple diagnostic tool based on the resonant Raman spectrum collected with the 532 nm laser without the possibility of any interference from other absorption bands.

FIG. 12. Changes in the UV-Vis absorption spectrum of overloaded lyc/HSA upon addition of HSA. The UV-Vis spectra on top are from 2 samples: (1) Lycopene/HSA 0.55/0.43 mM in PBS (ie, some HSA has both Sudlow I and Sudlow II binding sites occupied). (2) 0.86 mM HSA was then added, and sonicated for 20 minutes, thereby promoting the exchange of lycopene from some Sudlow II binding sites to unoccupied Sudlow I sites in the newly added HSA. The two UV-Vis spectra were nearly identical, and the chart on the bottom depicts the difference between the two spectrum. The difference spectrum clearly reveals features at 532 nm, these features may be ascribed to the aggregated form of lycopene (which is likely when both binding sites are occupied).

Thus, aggregation of albumin should also enable the aggregation of lycopene via a coordination of binding sites. This should change the optical spectrum of lycopene in a similar manner as was observed upon increasing the concentration of lycopene.

Potentially, other molecules can also be used. For instance, in the context of FIG. 12, β-carotene shows an absorption band at 510 nm, which is blue-shifted compared to the absorption bands of lycopene by about 20 nm.

In addition to the red shifting of the optical spectrum of lycopene, an enhanced absorption was observed as the wavelength decreased below 400 nm for concentrated lycopene (FIGS. 11 and 12). This enhanced absorption may not be due to any absorption band, but may be due to Rayleigh scattering from the clumps of albumin.

Raman scattering from the concentrated lycopene was about 10× less efficient than that from dilute lycopene, probably because of the enhanced Rayleigh scattering.

Example 9

Aggregation on the Bacterial Cell Wall of Hydrophobic Ligands Delivered Via Hydrophobic Ligand-Albumin Complexes The binding of HSA/lycopene to bacteria, and the accumulation of lycopene on the bacterial cell wall, were characterized by adding bacteria to a solution of HSA/lycopene in phosphate buffer saline (PBS), removing the bacteria (via a centrifuge step), and comparing the concentrations of lycopene after the centrifuge step with the concentration before bacteria addition. If some of the lycopene accumulated on the bacteria, then the addition and subsequent removal of the bacteria would have also removed some of the lycopene.

The measured UV-Vis absorption profiles of the lycopene/HSA complex in PBS before the addition of bacteria, with the added bacteria, and after the centrifuge step are illustrated in FIG. 5A for *Staphylococcus warneri*, at $1.7 \times 10^6$ CFU/mL and 0.8 µM lycopene, with 4.5% HSA in PBS (this concentration mimicked human serum). The 4 peaks in the absorption profile were due to lycopene, with the peak at 350 nm due to the cis form only and the triplet at 440-520 nm due to both cis and trans forms.

Figure 6:
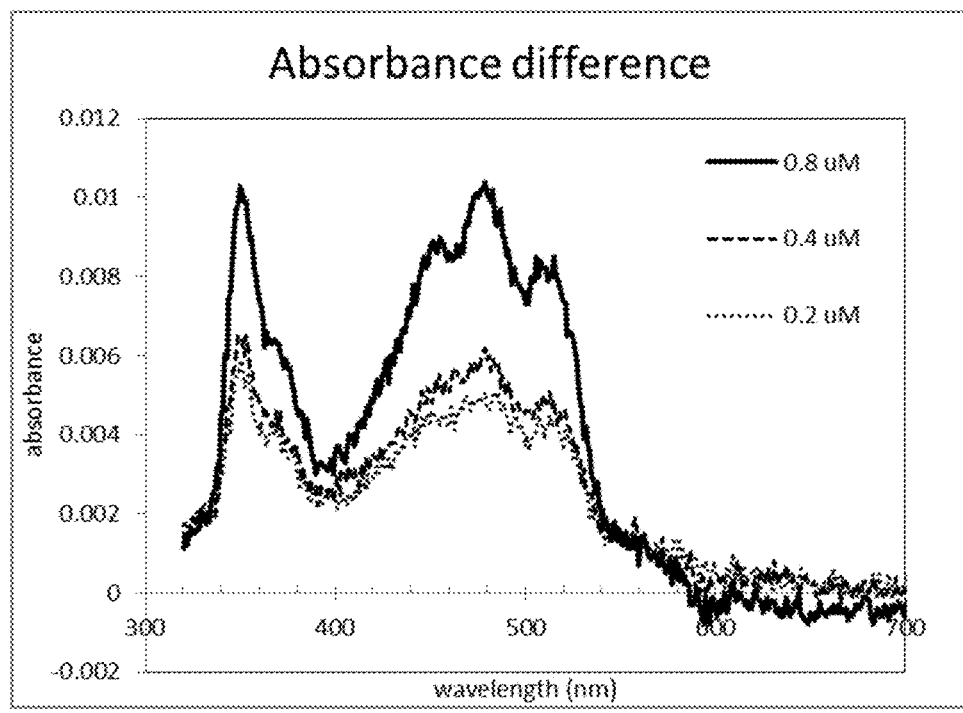
FIG. 6 is a graph showing the difference between the UV-Vis absorption profiles of initial and final states (defined as Profile A-Profile C in FIG. 5B) for 3 different concentrations of lycopene in HSA for *S. aureus* at $1.7 \times 10^6$ CFU/mL, according to embodiments of the present disclosure.

As can be seen in FIG. 5B, Profile A (HSA/lycopene only in the "before" state) is greater than Profile C (after bacteria has been added to it, and then removed via a centrifuge step; the "after centrifuge" state). FIG. 6 summarizes the difference between "initial" state (Profile A in FIG. 5B) and the final state (after centrifuge Profile C in FIG. 5B) for 3 different concentrations of lycopene. In all cases, some loss of the lycopene was observed. The loss scales with lycopene concentration indicating that the same amount of albumin is being lost during the centrifuge step.

FIGS. 5A. UV-Vis absorbance spectrum of bacteria only (Profile A), lycopene/HSA (Profile B), and the two mixed together (Profile C). As can be seen, the two parts, when mixed together, have a much greater background absorbance, compared to the sum of the two parts. The difference profile can be fitted with a power function of exponent 2, indicating aggregation of the lycopene/HAS that results in enhanced Rayleigh scattering.

FIGS. 5B. UV-Vis spectra of the Lycopene/HSA solution in the "before" state (profile A), after adding $1.7 \times 10^6$ CFU/mL of *S. aureus* (profile B) and after the final centrifuge (profile C). The difference profile indicates that a substantial amount of lycopene/HSA (nearly 20% of the original) is lost during the centrifuge step.

FIG. 6. Difference between the UV-Vis absorption profiles of initial and final states (Profile A-Profile C in FIG. 5B) for 3 different concentrations of lycopene in HSA for *S. aureus* at $1.7 \times 10^6$ CFU/mL.

Figure 7:
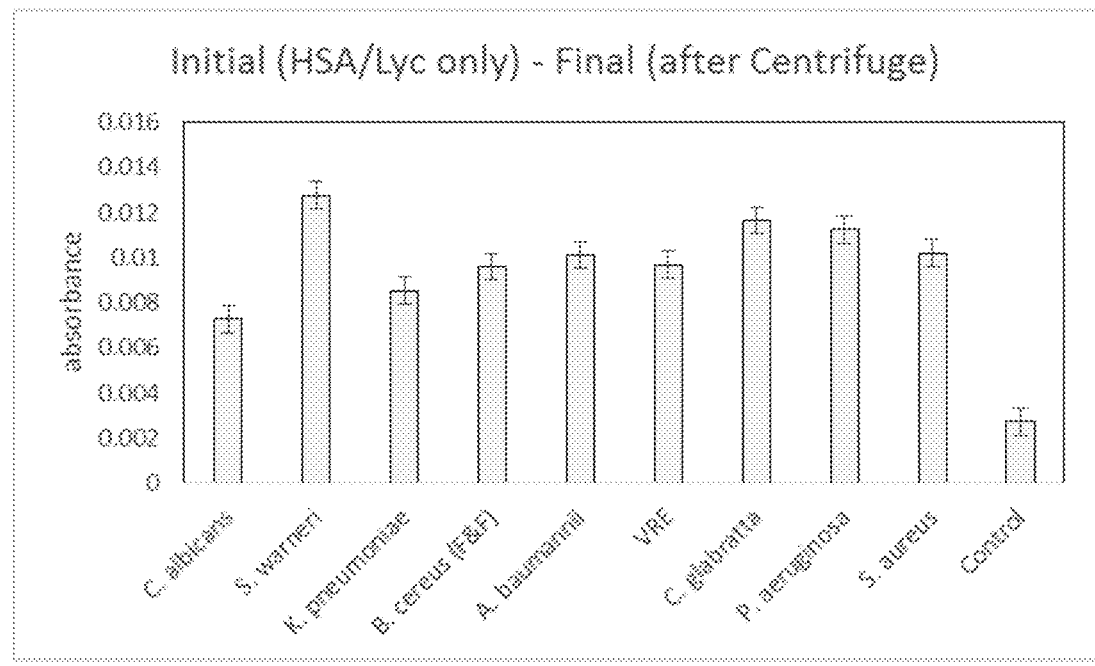
FIG. 7 is a graph summarizing binding of HSA to different microorganisms.

FIG. 7 summarizes the maximum in this UV-VIS difference plot depicted in FIG. 5B, for 0.8 µM lycopene/HSA for different bacterial and fungal microorgansism (all at $1.7 \times 10^6$ CFU/mL), along with the observed difference in a control sample. Some lycopene loss was observed in the control sample. This is believed to be due to the adsorption of the HSA/lycopene to the centrifuge tube. In all cases, the lycopene loss in samples with the microorganism was significantly greater than that in the control sample. Thus, it appeared that the transfer and aggregation of lycopene to the microorganism was common to these different types of microorganisms.

FIG. 7. Summary of binding of HSA to different microorganisms. In the control sample, no bacteria were added, but all other steps (including the centrifuge step) were performed. The decrease in the UV/Vis absorption profile in the control sample was probably due to the adsorption of a small amount of HSA on the centrifuge tube. The decrease in the samples that contains any microorganism was about 4-5× larger. The difference was likely due to the amount of HSA lost because it was bound to the bacteria which was pelletized by the centrifuge step.

The length of time bacteria was incubated in solution of HSA/lycopene to transfer and aggregate the lycopene to the microorganism cell wall varied depending on the source of the microorganism. For microorganisms suspended in PBS, 30 minutes was sufficient. For microorganisms in a clinical sample, 10 minutes was sufficient. Thus, the incubation time for transfer and aggregation of lycopene to the microorganism cell wall may depend on the whether the microorganism is in a latent state or an active state.

Example 10

Enhanced Killing Efficacy of Antimicrobials Via Antimicrobial-Albumin Complexes

In this example, the aggregation of the hydrophobic ligand on the pathogen cell surface was tested using the fungal pathogens *Candida albicans* (ATCC 90028) and *C. glabrata* (ATCC 2001). The efficacy of the disclosed formulation of Amphotericin B (Sigma Aldrich catalogue A4888) incorporated into bovine serum albumin (AmpB/BSA) was tested using the methods described herein, with the efficacy of the commercially available liposomal Amphotericin B (LAMB Sigma Aldrich catalogue A2942). It has been previously reported that the minimum inhibitory concentration MIC of Amphotericin B required for inhibiting growth of *C. glabrata* and *C. albicans* is about 0.5 µg/mL.

The measurements were set up by calibrating the Amphotericin B content in the AmpB/BSA formulation described herein, with the commercially available LAMB formulation. The Amphotericin from both were dissolved in DMSO:$H_2O$(1:1), and then the UV-Vis absorption curves of AmpB/BSA dissolved in DMSO/$H_2O$ were calibrated with LAMB dissolved in DMSO/$H_2O$, and then used to calibrate the UV-Vis absorption curve of the aqueous solution of AmpB/BSA.

Figure 8:
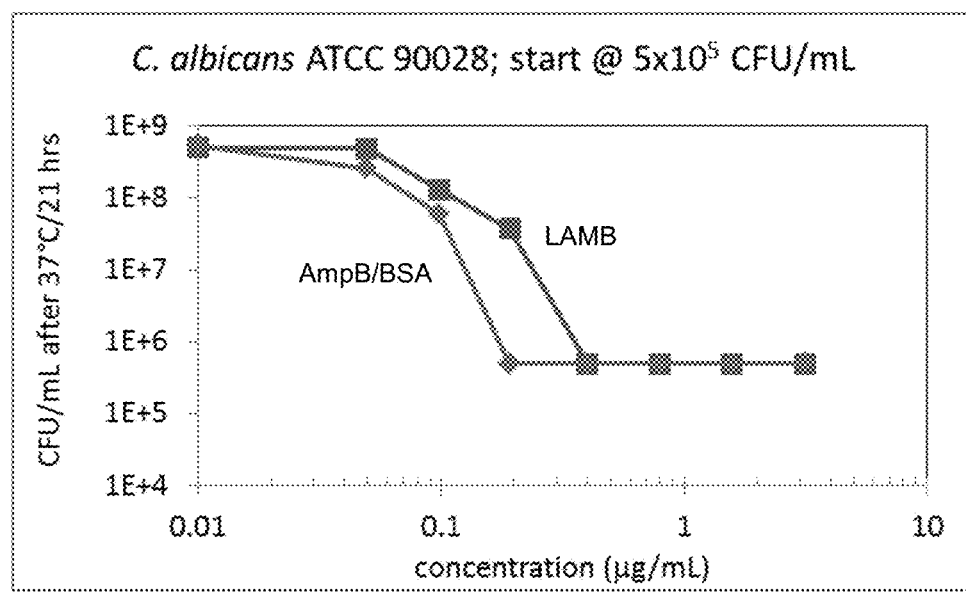
FIG. 8 is a graph showing growth curves of *Candida albicans* (ATCC 90028), with an initial concentration of $5 \times 10^5$ CFU/mL under different concentrations of Amphotericin B/bovine serum albumin complex (AmpB/BSA) or liposomal Amphotericin B (LAMB), according to embodiments of the present disclosure.

The efficacy was demonstrated by comparing the growth of *C. albicans* and *C. glabrata* from a starting concentration of $5 \times 10^5$ CFU/mL with varying amounts of Amphotericin B introduced into the solution as either the AmpB/BSA aqueous solution, or the LAMB formulation. Results are depicted in FIG. 8 for *C. albicans* and FIG. 9 for *C. glabrata*. In both cases, the commercially available LAMB formulation suppressed growth when the concentration of Amphotericin B exceeded 0.4 µg/mL, which was consistent with the previously reported MIC values. The AmpB/BSA formulation suppressed growth when the Amphotericin B concentration exceeded 0.2 µg/mL, which corresponded to a very significant reduction of MIC by 2×. This reduction in MIC is consistent with a concentration of the hydrophobic ligand on the cell surface.

FIG. 8. Growth curves of *C. albicans* (ATCC 90028) with an initial concentration of $5 \times 10^5$ CFU/mL under different concentrations of Amphotericin B. LAMB is liposomal Amphotericin B, which is a commercially available water soluble form purchased from Sigma (catalogue A2942). AmpB/BSA is the present water soluble formulation wherein the Amphotericin B is suspended in bovine serum albumin. As can be seen, *C. albicans* growth is suppressed when the concentration exceeds 0.4 µg/mL for LAMB, and 0.2 µg/mL for the disclosed AmpB/BSA formulation.

Figure 9:
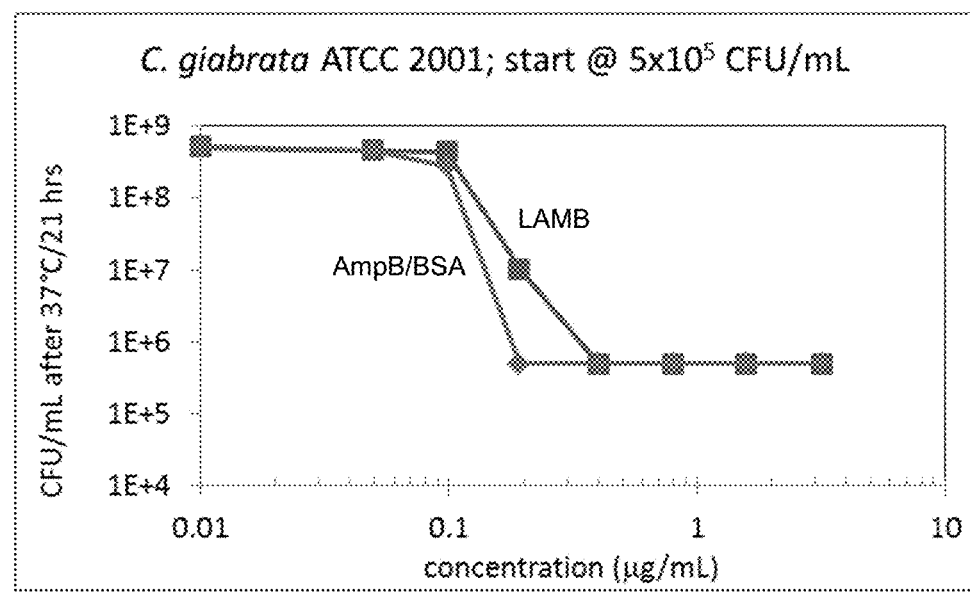
FIG. 9 is a graph showing growth curves of *Candida glabrata*, with an initial concentration of $5 \times 10^5$ CFU/mL under different concentrations of AmpB/BSA or LAMB, according to embodiments of the present disclosure.

FIG. 9. Growth curves of *C. glabrata* with an initial concentration of $5 \times 10^5$ CFU/mL under different concentrations of Amphotericin B. Similar conditions were used as FIG. 8. Once again, the MIC is suppressed from 0.4 µg/mL for LAMB to 0.2 µg/mL for AmpB/BSA.

Example 11

Improved Formulation of Hydrophobic Ligands Via Hydrophobic Ligand-Albumin Complexes An albumin based delivery system, as described herein, can be used to expand the antimicrobial space. There are several existing antimicrobial compounds with documented in-vitro efficacy when used in an organic solvent, but which are not used because they are insoluble in water and the poor solubility poses significant pharmacokinetic challenges. One such example is Clofazimine, which is on the World Health Organization (WHO) list of essential medicines. Clofazimine is an anti-inflammatory and anti-mycobacterial compound, with an impressive in vitro performance against multidrug-resistant strains of *Mycobacterium tuberculosis*. However, its use is currently limited to the treatment of leprosy because it is not water soluble; and thus provides for poor pharmacokinetics against bacteria: Clofazimine is administered as a microcrystalline suspension in an oil-wax base; and ingestion of a 200 mg tablet results in a peak plasma concentration of only 0.41 µg/mL with a time to $C_{max}$ of 8 hours. Since the MIC of this drug against most gram positive organisms is also about 0.4 µg/mL, the pharmacokinetic (PK) issues prevent its use. Aside from these PK issues, clofazimine is known to be active against several Gram positive bacteria (via in vitro studies wherein it is dissolved in DMSO or in acidic ethanol).

Figure 10:
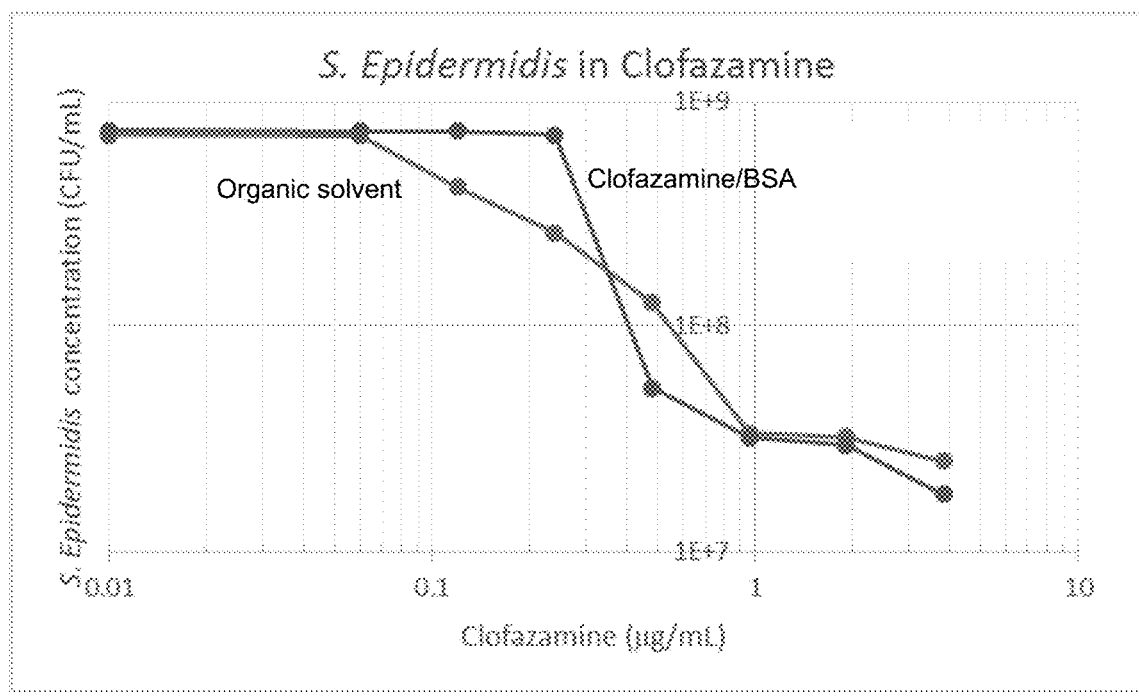
FIG. 10 is a graph showing growth curves of *S. Epidermidis*, with an initial concentration of $5 \times 10^5$ CFU/mL under different concentrations of Clofazamine/BSA or Clofazamine in an organic solvent formulation, according to embodiments of the present disclosure.

To test the feasibility of using albumin as a carrier for Clofazamine, Clofazamine was incorporated in albumin using methods as describe herein, and thus into a water soluble formulation. The in vitro activity of the Clofazamine-albumin complex, water soluble formulation against *Staphylococcus epidermidis* is shown in FIG. 10. As shown in the figure, the water soluble formulation had an in vitro activity that was just as good as the organic formulation. With this formulation, it is possible that the PK issues will be addressed by the long retention time of albumin in the body.

FIG. 10. *S. Epidermidis* in Clofazamine. The two traces represent the concentration of *S. Epidermidis* after an 18 hour incubation period, with a starting concentration of 500,000 CFU/mL and a varying concentration of drug, as indicated on the X-axis. The two traces represent the drug in an organic solvent (2 mg/mL concentration of Clofazamine in 10 mM acetic acid/ethanol; this organic solvent formulation has been previously demonstrated against several gram positive organisms) and the water soluble formulation wherein Clofazamine was incorporated into BSA. As can be seen, the water formulation affords an MIC of about 0.5 µg/mL, which is identical to that from the organic solvent formulation.

Example 12

Detection of Microorganisms in Clinical Samples Via Hydrophobic Ligand-Albumin Complexes The following experiments demonstrated that a hydrophobic ligand-albumin complex of the present disclosure can be used to detect microorganisms in clinical samples.

Detection of Microorganism-Induced Red Shift in the Lycopene Optical Spectrum.

Figure 13:
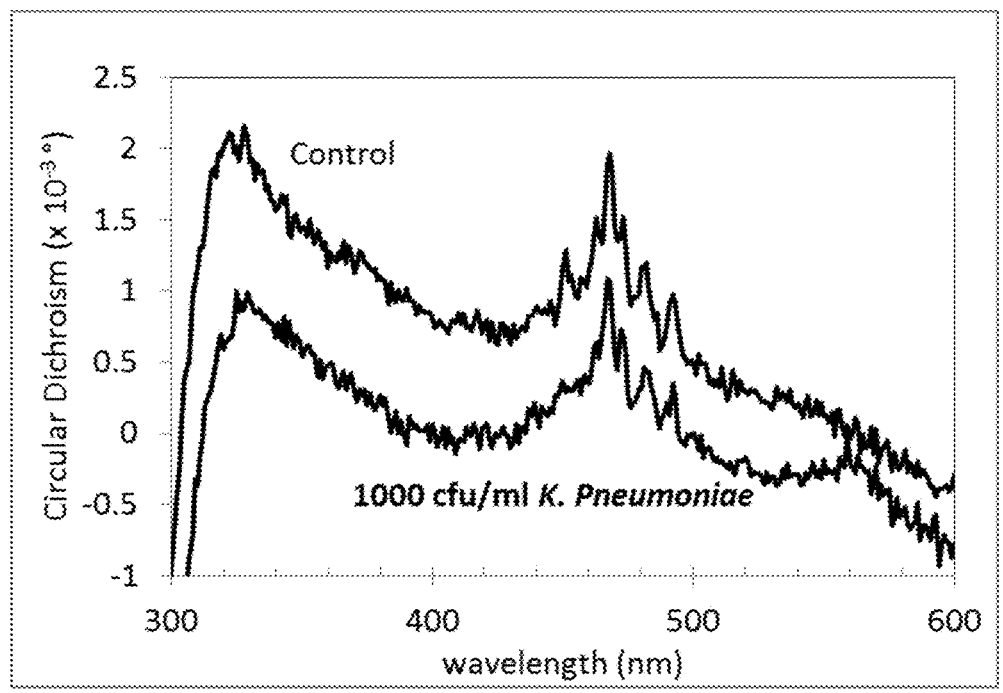
FIG. 13 is a graph showing circular dichroism spectra of two samples containing lycophene/HSA, without and with added 1000 CFU/mL Klebsiella pneumoniae, according to embodiments of the present disclosure.

The hydrophobic ligand-albumin complex-based sensor system included lycopene (that has been substantially isomerized into the cis form) incorporated into HSA; when a pathogenic microorganism was present in the vicinity, then the HSA changed conformation. This was observed by circular dichroism measurements which showed that the distribution of vibrational energies of the albumin-lycopene complex shifted as a result of the presence of the microorganism (FIG. 13). While both infected and uninfected samples showed a CD spectra that are dominated by the absorption triplet of lycopene, in samples that contain a microorganism, the circular dichroism spectrum showed additional absorption bands at 565 nm that were not normally seen in the uninfected samples.

FIG. 13. Circular dichroism spectra of two samples without and with added 1000 CFU/mL *K pneumoniae*; both prepared with 0.6 ml PHS and 5.4 ml PBS. In the infected sample, there is an additional peak at 565 nm, which is due to aggregation of lycopene.

Figure 24:
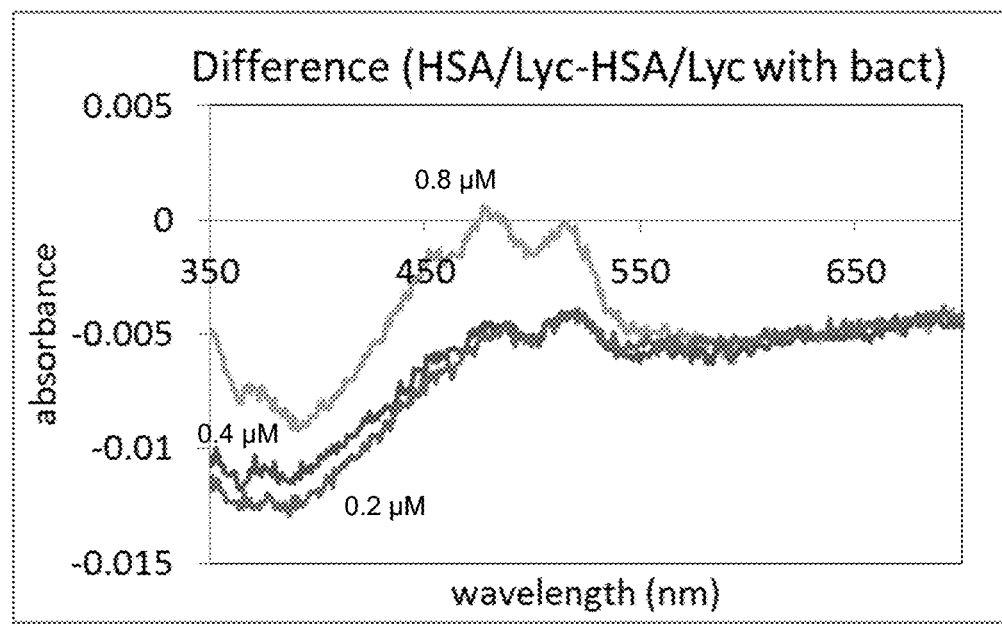
FIG. 24 is a graph showing UV-Vis absorption profile difference between lycopene/HSA and lycopene/HSA with S. aureus, for 3 different concentrations of lycopene.

Interestingly, the UV-Vis absorbance from the lycopene triplet also changed with bacteria addition. FIG. 24 summarizes the change in the UV-Vis absorbance when bacteria are added to the HSA/Lycopene. The profile included a broad change in the background, consistent with the Rayleigh scattering due to the bacteria, but also included features that resembled the absorbance triplet of lycopene along with a minor peak at 565 nm. These features were consistent with transfer and aggregation of lycopene from the HSA complex to the bacteria cell wall—aggregation of carotenoids changed the UV-Vis absorbance.

FIG. 24. Difference between the UV-Vis absorption profiles of initial and final states (Profile A-Profile C in FIG. 5B) for 3 different concentrations of lycopene in HSA for *S. aureus* at $1.7 \times 10^6$ CFU/mL.

Based on these and other findings, two methods to detect microorganisms in a sample, e.g., clinical sample, were developed: (a) First, a probe that characterizes the optical signature from lycopene was used to characterize this signature at a fixed spatial point within the test vial, and as a function of time. As an example, the probe is a Raman spectrometer using 532 nm illumination, and monitors the lycopene peaks at 1516 and 1156 $cm^{-1}$. The probe was used to monitor the lycopene Raman peaks in the glass vial at a point well above the level at which the aggregated albumin segregates. The energy of the probe is sufficient to alter the conformation of the aggregated albumin—in the examples provided herein, 532 nm illumination lasers with powers of 25 mW, 50 mW and 100 mW were used. If pathogenic microorganisms are present, then this results in the formation of aggregated albumin, whose conformation is altered by the energy of the incident laser light, which results in a steady decrease of the observed lycopene Raman peaks. Thus, a decrease in the measured lycopene over time is indicative of the presence of pathogenic microorganisms. (b) The second method involved a probe that can move along a linear axis, and which was used to monitor changes in the spatial profile of the lycopene Raman peak. If any pathogenic microorganisms were present in the assay, then this results in the presence of aggregated albumin (which are not entirely in solution), and thus the spatial profile is not uniform.

Figure 15:
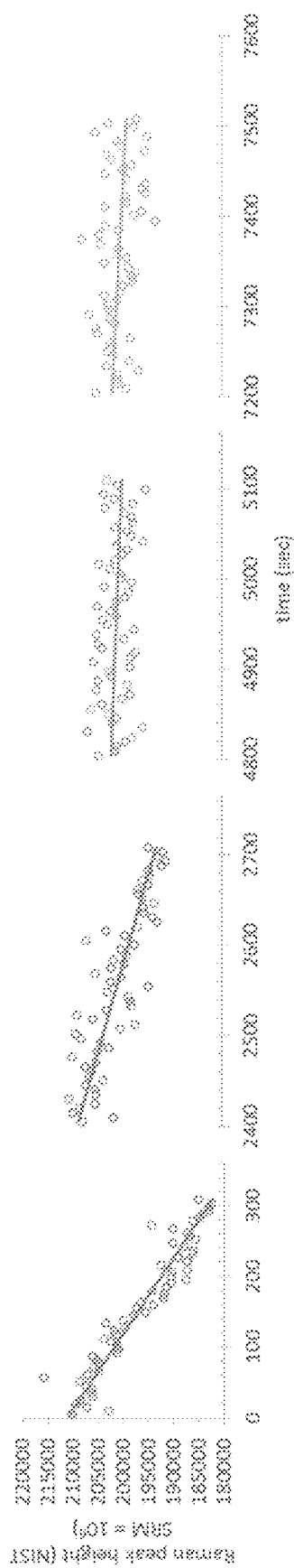
FIG. 15 is a collection of graphs showing lycopene Raman peak height as a function of time for a test sample with 100 CFU/6 mL of S. aureus, according to embodiments of the present disclosure.

Detection of Microorganism-Induced Shift in the Temporal Profile of the Lycopene Raman Peak Height Upon exposure to laser light that is absorbed by the lycopene ligand, with some of this energy being transferred to the host albumin and thus altering albumin conformation, there was a net decrease in the Raman cross section of lycopene within the aggregates the albumin aggregate (FIG. 15). These changes are reversible, as illustrated in FIG. 15, which plots the lycopene Raman peak height as a function of time at 20 mm from the bottom of the test vial. As can be seen in the figure, the lycopene Raman peak height decreased steadily upon laser illumination, and recovers to nearly the original value when the light is turned off. A similar decrease was observed upon subsequent illumination, albeit the magnitude of this decrease was reduced. Because the changes were reversible, they could not be due to any chemical changes, or the formation of any new aggregates of albumin/lycopene. Instead, these changes were likely due to photo-induced conformation changes of the host albumin when it was in the aggregated form. It is believe that the host albumin in the aggregates rearranged itself so as to enable a coordination of the lycopene binding sites. This coordination results in a red shifting of the optical spectrum of lycopene, and thus a decrease in the Raman peak intensity.

FIG. 15. The lycopene peak height as a function of time for a test sample with 100 CFU/6 mL of S. aureus. The sample vial was continuously illuminated with laser light (100 mW laser power, at a fixed position 20 mm from the bottom of the vial) from 0-300, 2400-2700, 4800-5100 and 7200-7500 seconds. Upon laser illumination, the lycopene peak height decreases steadily, but recovers to nearly the original value when the illumination is turned off.

Figure 16:
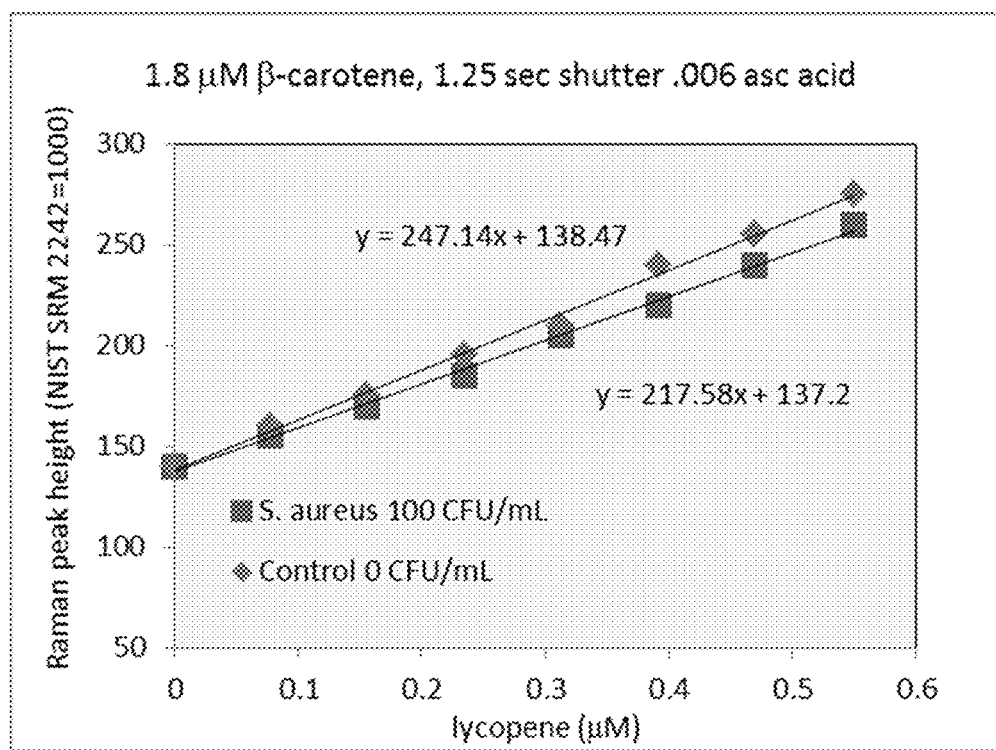
FIG. 16 is a graph showing the height of the resonant Raman peak at 1156 cm$^{-1}$ as a function of lycopene content for uninfected samples, and samples that contain 100 CFU/mL S. aureus, according to embodiments of the present disclosure.
Figure 17:
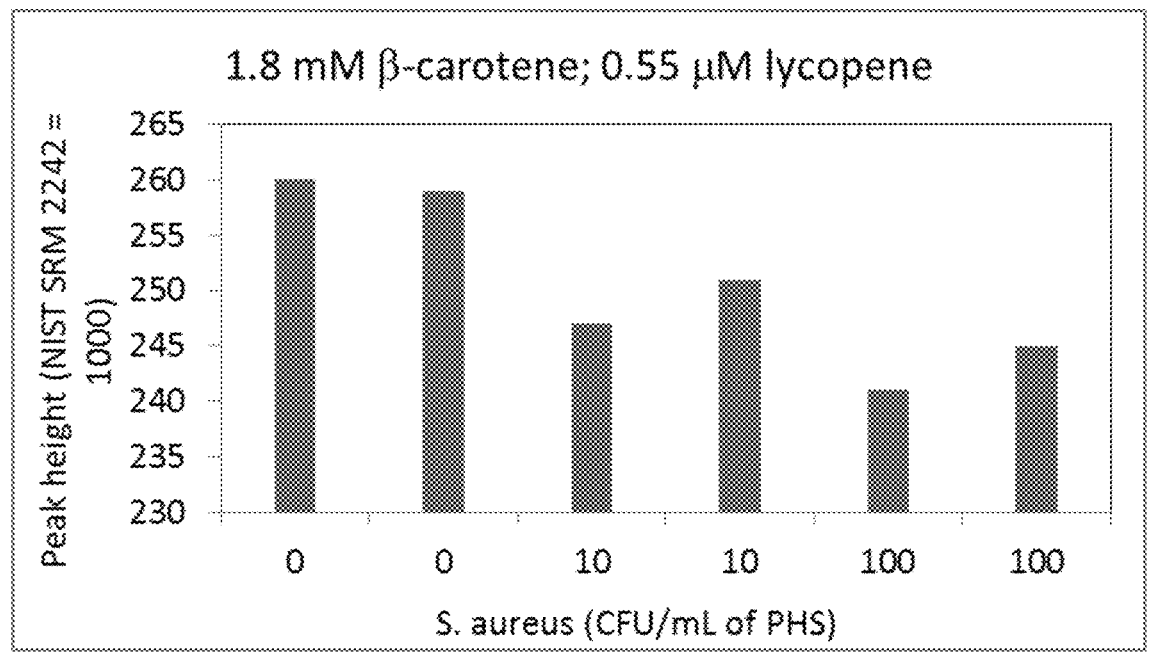
FIG. 17 is graph showing lycopene Raman peak height as a function of pathogen concentration, according to embodiments of the present disclosure PHS: pooled human serum.

The temporal profile of the two dominant Raman peaks was measured when the sample was illuminated with 532 nm light. For infected samples, the time profile of the Raman peak heights showed a decrease over time, with the changes initiating with laser exposure and saturating out within a relatively short period of time, about 5 to 10 minutes for most samples. As depicted in FIG. 16, the presence of a pathogenic microorganism in a sample could be detected by mixing a sample with the lycopene/HSA formulation, and measuring the absolute values of the resonant Raman peaks after a 10 min incubation step. These changes were semi-quantitative, as depicted in FIG. 17. However, the serum from a potentially sick patient will have an unknown (and variable) level of lycopene in it, and so a diagnostic test is developed wherein the rate of change of the Resonant Raman peak can be used as an indicator instead of the absolute level. One example of this is illustrated in FIG. 18 for S. aureus.

FIG. 16. The height of the resonant Raman peak at 1156 $cm^{-1}$ as a function of lycopene content for uninfected samples, and samples that contain 100 CFU/mL S. aureus. These measurements were done 20 mm from the bottom of the glass vial.

FIG. 17. Raman peak height as a function of pathogen concentration. All samples were 6 mL total, including 500 mL pooled human serum with either 0, or 5 or 50 CFUs of added S. aureus (corresponding to pathogen concentrations of 0, 10 and 100 CFU/mL of PHS).

Figure 18:
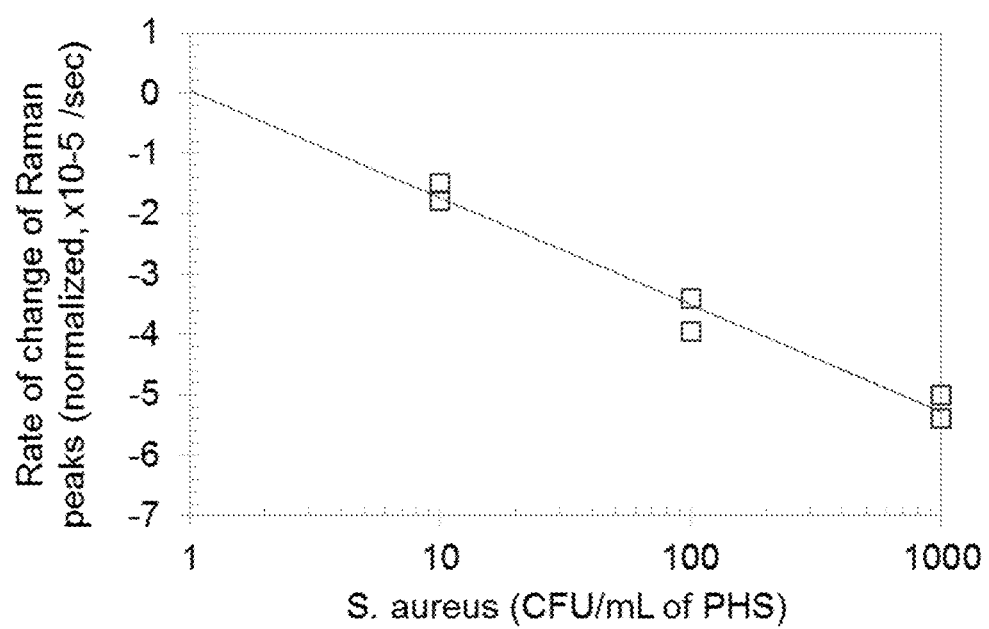
FIG. 18 is a graph showing the rate of change of the Raman peaks with varying amounts of S. aureus, according to embodiments of the present disclosure.

FIG. 18. Rate of change of the Raman peaks in 6 samples, each with 6 mL total sample volume and 500 mL of PHS with varying amounts of S. aureus as indicated.

Figure 19:
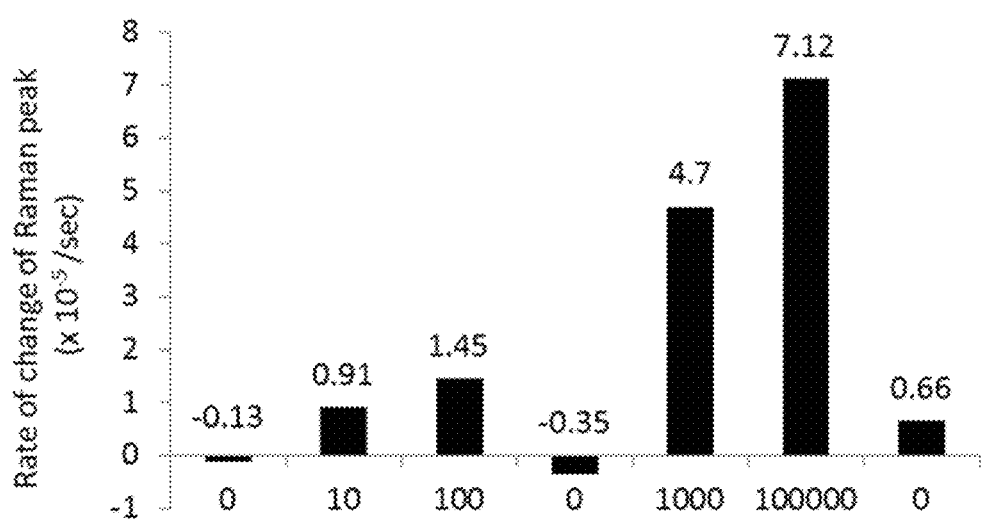
FIG. 19 is a graph showing the negative of the rate of change of the lycopene Raman peak with varying concentrations of vancomycin resistant Enterococci, according to embodiments of the present disclosure.

FIG. 19 illustrates results from a notional diagnostics test that seeks to detect the presence of pathogens in 7 samples that include 3 that are uninfected and 4 infected inoculated with different amounts of vancomycin resistant enterococci (VRE). As depicted in the figure, there is a clean separation between uninfected and infected samples using this method.

FIG. 19. The negative of the rate of change of the lycopene Raman peak for 7 samples with varying concentrations of vancomvcin resistant Enterococci.

TABLE 1

Summary of tested microorganisms, the signal average from the 3 uninfected control samples, from the 3 infected sampes, and the ratio of the pathogen concentrations based on culture and McFarland standards.

| Pathogen | 0 CFU/Ml | 10; 100; 1000 CFU/mL | Obs/Exp conc. |
| --- | --- | --- | --- |
| E. coli 10418 | 0.21 | −4.36; −4.08; −3.29 | 0.20 |
| E. coli 12241 | 0.00 | −3.51; −3.07; −1.17 | 0.18 |
| S. Aureus | 0.01 | −1.62; −1.97; −1.60 | 0.44 |
| S. epidermidis | −0.18 | −4.23; −3.85; −3.51 | 0.71 |
| K. pneumoniae | 0.96 | −3.41; −3.61; −3.90 | 0.58 |
| E. cloacae | −0.46 | −2.03; −1.87; −2.98 | 0.51 |
| E. faecalis | 0.43 | −2.56; −2.77; −2.45 | 0.18 |
| S. pneumoniae | −0.35 | −5.76; −8.97; −4.37 | 0.24 |
| P. aeruginosa | −0.33 | −3.10; −2.16; −3.20 | 0.70 |
| P. mirabilis | 0.86 | −9.80; −1.00; −2.40 | 1.41 |
| S. pyogenes | 0.39 | −1.46; −2.59; −2.47 | 0.95 |
| C. albicans | 0.04 | −0.86; −1.14; −1.78 | 2.85 |
| S. typhimurium | −0.50 | −3.81; −0.60; −2.71 | 0.45 |
| P. rettgerri | 0.94 | −1.17; −2.13; −1.06 | 1.05 |
| B. fragilis | −1.51 | −1.80; −2.52; −2.86 | 4.30 |
| A. baumannii | 0.78 | −2.48; −2.76; −1.63 | 2.32 |
| E. faecium | 0.28 | −1.87; −4.00; −1.51 | 1.35 |
| S. maltophilia | −0.51 | −8.01; −4.40; −1.16 | 1.23 |
| C. glabrata | 0.63 | −9.17; −2.15; −2.76 | 0.33 |
| S. aureus (MRSA) | 0.13 | −2.67; −2.40; −2.08 | 0.74 |
| C. freundii | −0.03 | −4.32; −4.94; −2.71 | 1.96 |
| Average | 0.09 | −3.71; −3.00; −2.46 | |
| Stdev | 0.60 | 2.54; 1.78; 0.92 | |

21 different pathogenic microorganisms were tested at clinically relevant concentrations (10 CFU/mL) in a 20 min test, to demonstrate the clinical applicability of the detection method. Results are presented in Table 1, which summarizes the signal output for 21 different microorganisms. In this case, the signal refers to the rate of change of the lycopene peak height (all measured 20 mm from the bottom of the test vial), as a function of time. The 0 CFU/mL refers to the average value for the 3 uninfected control samples; and Obs/Exp concentration refers to the ratio between the number of viable colonies observed in the test samples compared to the number expected from the McFarland standard. In some cases, this ratio was as low as 0.2; the corresponding 10 CFU/mL sample was in fact 2 viable CFU/mL. From the table, it is clear that the signal from the average uninfected sample was clearly different than the signal from any of the infected samples.

To gauge the applicability of the disclosed methods to human samples, multiple samples were tested in parallel. In the standard setup that can measure 8 samples at a time, 9 experiments spread over 4 days were performed, whereby 4 control and 4 infected samples in each experiment were tested. For all samples, the evolution of the Raman peak was monitored for 10 minutes, at a fixed point in the glass vial.

All samples were created with 0.6 mL pooled human serum, and had a total sample volume of 6 mL containing 0.6 µM lycopene/HSA and 1.5 µM β-carotene/HSA and had 2 mL of 1× trypticase soy broth (this is added to support pathogen viability). In all cases, the pH was controlled to 7.4 using a phosphate buffer saline (PBS) with a starting pH of 7.4 and the addition of a small amount of ascorbic acid. The assay was prepared using the methods described earlier, and stored in a refrigerator at 5° C. Prior to use, it was incubated in a 37° C. water bath for 30 minutes (this is done so that the albumin conformation reverts to the standard one in the human body), and sonicated using a 100 W ultrasonicator for 30 minutes (this is done to break up any aggregates of albumin as it is known that albumin can form aggregates when it is stored below 37° C. for extended periods).

Figure 20:
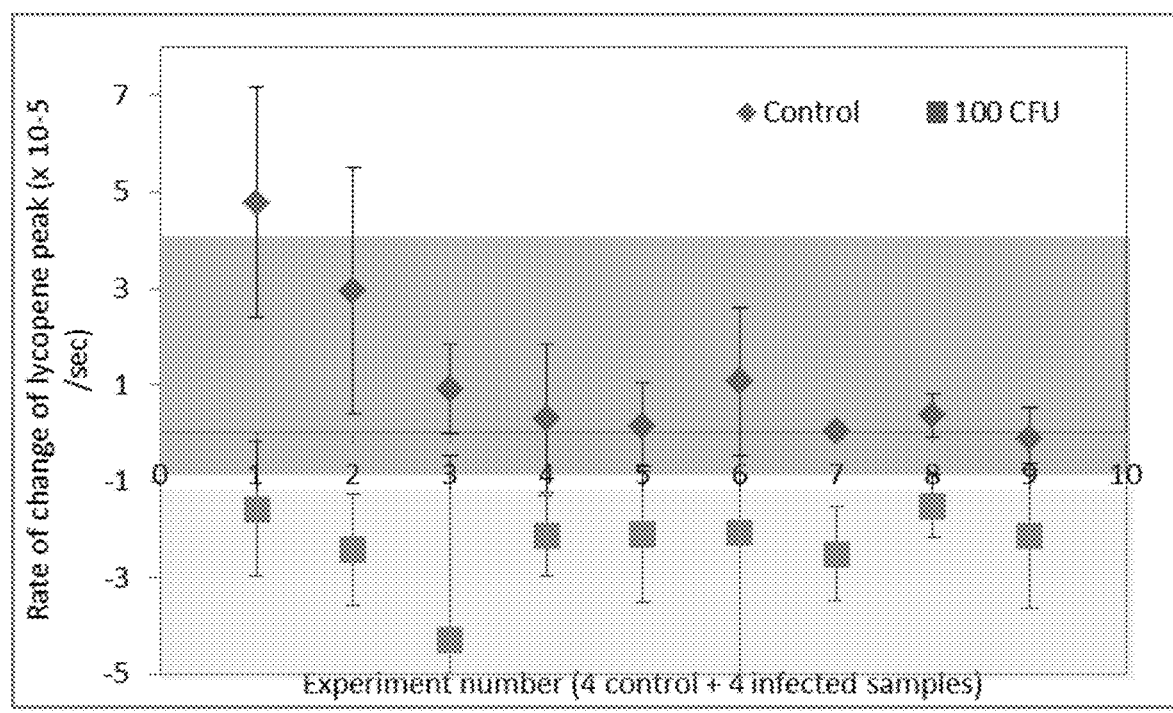
FIG. 20 is a graph showing the negative of the rate of change of the lycopene Raman peak from different experimental samples with or without addition of 100 CFUs of S. aureus, according to embodiments of the present disclosure.

All the infected samples were created with 0.6 mL pooled human serum and the addition of 100 CFUs of S. aureus in 0.1 mL of PBS and the control samples were created with the addition of 0.6 mL of pooled human serum and 0.1 mL of PBS. The rate of change of the two lycopene peaks at 1516 and 1156 cm$^{-1}$ were measured using 532 nm laser light (at this illumination wavelength, the Raman spectrum was dominated by the contribution of lycopene), and FIG. 20 depicts the results of the 9 experiments, whereby the data points and error bars represent the average and +/− one standard deviation of the 4 control and infected samples. It can be seen that the infected samples lie in the red band, and the control sample lie in the blue band.

FIG. 20. Test results from 9 experiments, each experiment with 4 control and 4 infected samples.

Figure 21:
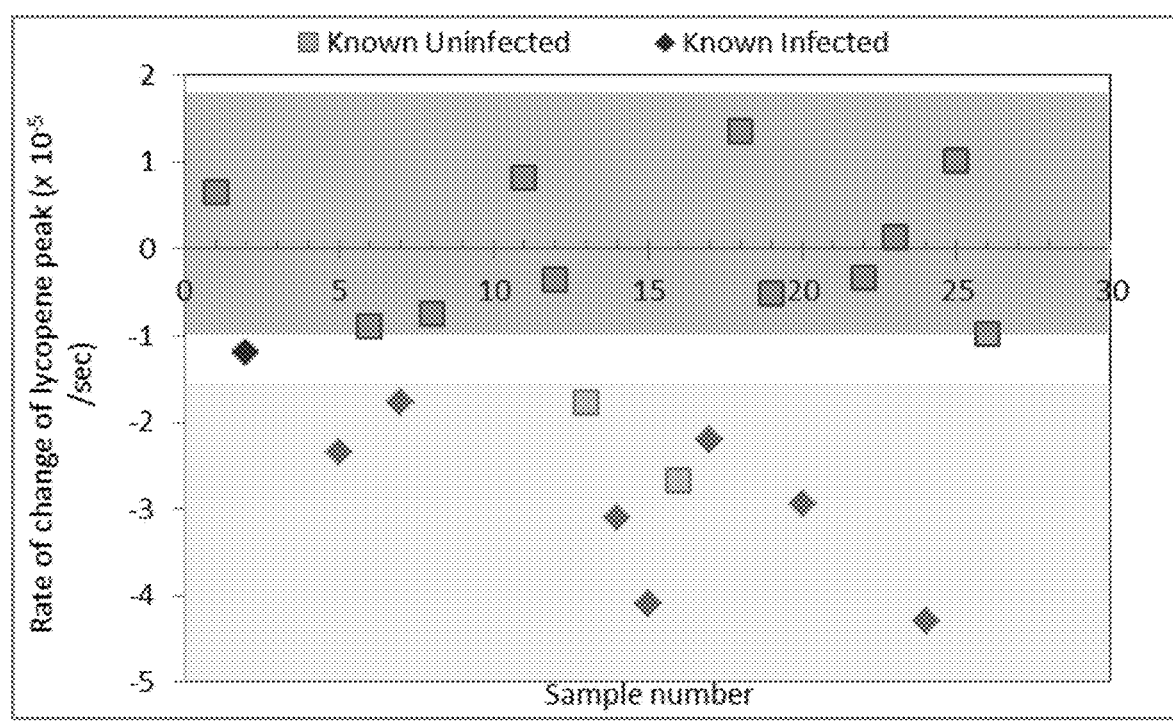
FIG. 21 is a graph showing the rate of change of the lycopene Raman peak from clinical samples having known infection status, according to embodiments of the present disclosure.

Then, detection thresholds established in FIG. 20 were used to test and characterize 25 samples created from real human patients and were either known infected or known uninfected depending on the eventual outcome of the blood culture testing (in most cases, the blood culture test results were not available during the tests). Results are depicted in FIG. 21. In general, there was good concordance between the results and the blood culture method. The plasma samples were significantly more noisy. This may be due to the presence of white blood cells in the plasma samples; in general, febrile patients tend to have a higher white blood cell count. The two samples that would have been incorrectly diagnosed (sample #s 13 and 16) were excessively noisy due to a very high white blood cell count.

It may also be due to the use of potassium phosphate based buffers. It is known that potassium phosphate reacts with calcium chloride (which is dissolved in the patient plasma) to form potassium chloride and calcium phosphate. Calcium phosphate is insoluble in water, and likely binds to the albumin. The signal traces are cleaner when all potassium phosphate is removed from the reagents utilized in the disclosed methods. As an example, buffers were created using HEPES and sodium hydroxide, and the TSB broth was also reformulated using the ingredients and replacing potassium phosphate with HEPES—these reagents provided for cleaner signal traces.

FIG. 21. Results from 25 samples using plasma from human patients. In all cases, the "known uninfected" samples are those for which both the blood culture test (from a different draw on the same patient) and a culture of the test vial comes in negative, and the "known infected" samples are those for which either the blood culture, or the culture of the test vial is positive. In some of the "known infected" samples, 100 CFUs of S. aureus were added to "known uninfected" plasma.

Detection of Microorganism-Induced Shift in the Spatial Profile of the Lycopene Raman Peak Height.

Figure 14:
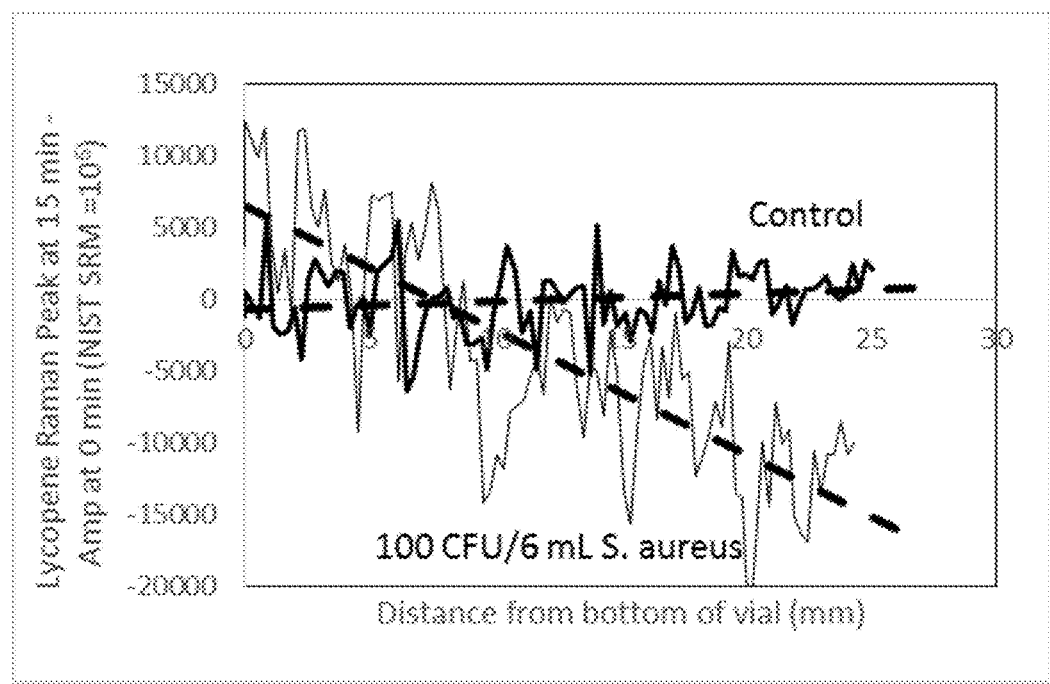
FIG. 14 is a graph showing the difference between the amplitude of the lycopene Raman peak at 1516 cm$^{-1}$ at time t=0 and t=15 min for a control (uninfected) sample, and one that contains 100 CFU/6 mL S. aureus, according to embodiments of the present disclosure.

It was found that the presence of microorganisms in a sample generates a spatial profile in the Raman peak from lycopene that is distinct from that in the absence of the microorganism (FIG. 14). This is consistent with the aggregates of lycopene-albumin crashing out of solution. Thus aggregation of the lycopene-albumin into a complex that segregates to a separate layer may be used to detect microorganisms in a sample.

FIG. 14. The difference between the amplitude of the lycopene Raman peak at 1516 cm$^{-1}$ at time t=0 and t=15 min for a control (uninfected) sample, and one that contains 100 CFU/6 mL S. aureus. The two plots depict the difference as a function of distance from the bottom of the glass vial, for a 6 mL test assay that is about 25 mm in height. As shown in the figure, for the uninfected sample, there is no change in the Raman peak height, either at the bottom, or at the top of the glass vial. For the infected sample, the Raman peak height decreases at the top of the glass vial.

Figure 22A:
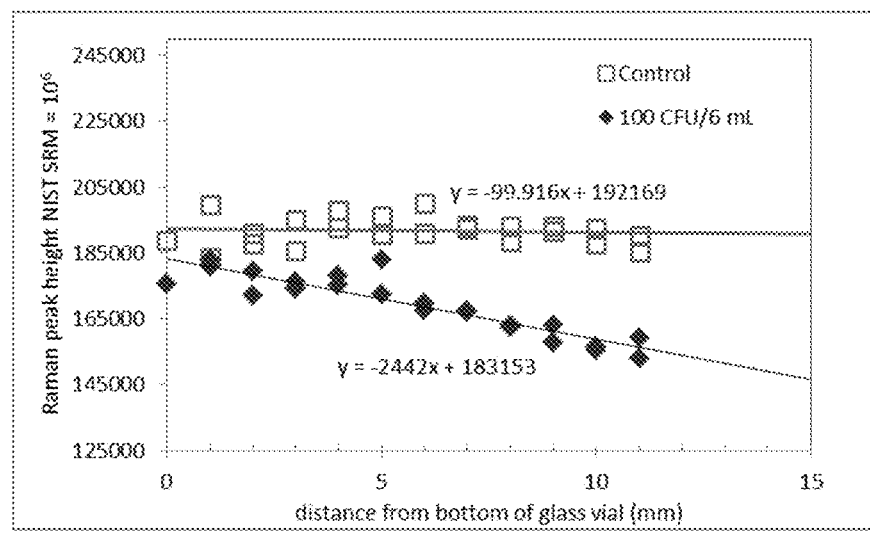
FIGS. 22A and 22B are a collection of graphs characterizing the spatial profile of lycopene Raman peak height in a vial, according to embodiments of the present disclosure.
Figure 22B:
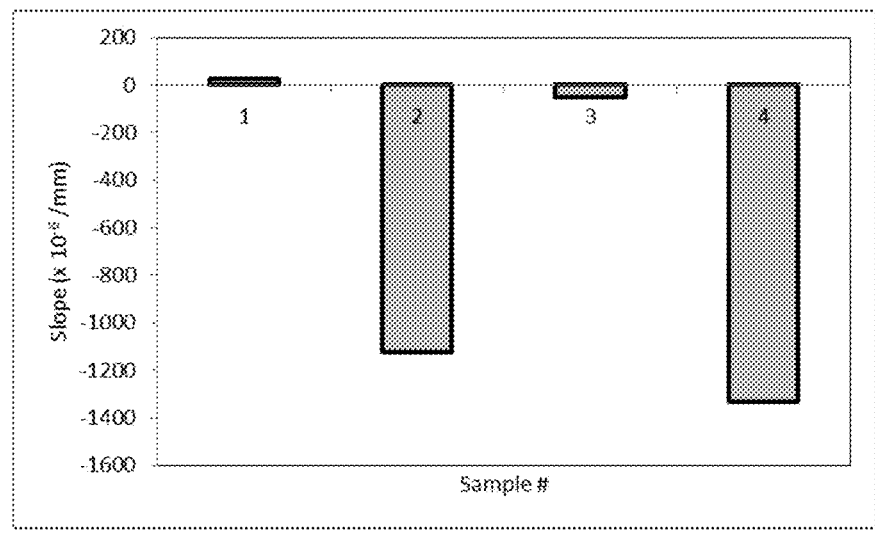

The presence of microorganisms in an unknown test sample was diagnosed by characterizing the vertical spatial profile of lycopene (FIGS. 22A and 22B). The unknown test sample was mixed with lycopene incorporated into albumin (lycopene concentration 1.5 µM), as described previously. The mixture was left for 15 minutes for the lycopene-albumin complex to interact with the bacteria, and tested samples immediately afterwards.

For uninfected samples, because the albumin-lycopene system was in solution, the concentration remained invariant over distance. For infected samples, if the albumin had aggregated, then there was a higher concentration at the bottom of the test vial, as illustrated in FIGS. 22A and 22B.

FIGS. 22A and 22B. (FIG. 22A) The vertical profile of lycopene for two test samples that both contain a disclosed assay (with 1 µM lycopene). The profile in blue represents an uninfected control sample, and the profile in red represents a sample that has 100 CFU of S. aureus in a 6 mL test sample. (FIG. 22B) Slope of the vertical profile, for 4 samples; Samples 1 and 3 are uninfected control samples and Samples 2 and 4 have 100 CFU of S. aureus in a 6 mL sample.

Example 13

Diagnosing Antimicrobial Susceptibility Using Lycopene/HSA Complexes

Figure 23:
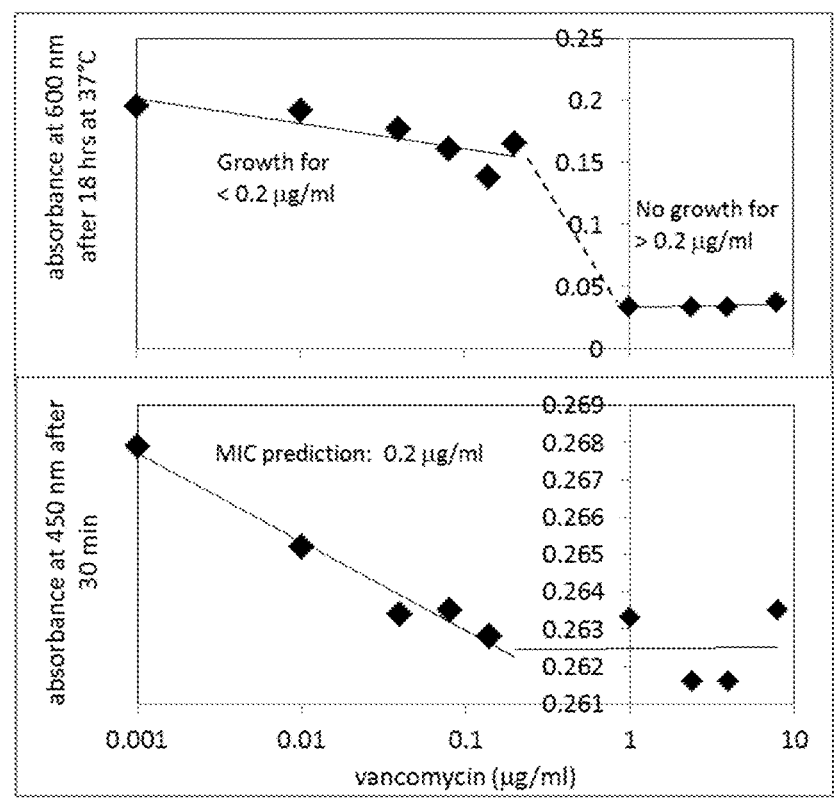
FIG. 23 is a collection of graphs showing a prediction of the minimal inhibitory concentration (MIC) of S. aureus at 200 CFU/mL, according to embodiments of the present disclosure.

The present lycopene/HSA complexes were used to characterize the minimum inhibitory concentration (MIC) of antimicrobial compounds. A lycopene/HSA complex, prepared as described herein, was mixed with a series of samples that all had the same initial amount of S. aureus (200 CFU/mL of PHS), and which was incubated with a varying amount of vancomycin for 30 minutes. FIG. 23 shows a plot of the UV-Vis absorbance at 350 nm against the varying amounts of vancomycin. Upon the addition of the lycopene/HSA assay, aggregation of the lycopene/HSA increased in a manner that scales with S. aureus concentration (and thus on the vancomycin concentration). These changes were characterized via the changes in the UV-Vis spectrum, depicted at the bottom in FIG. 23. The chart on the top in FIG. 23 depicts the absorbance at 600 nm for these samples after another 18 hours of incubation. This absorbance was dominated by the pathogen concentration after 18 hours of growth. As can be seen from the figure, the bottom trace predicted an MIC of about 0.6 µg/mL, which is consistent with the chart on top, and also with previously reported MIC values for vancomycin/S. aureus, which are in the range of 0.5 to 1 µg/ml.

FIG. 23. Rapid prediction of the MIC of S. aureus at 200 CFU/mL. In this experiment, each 2560 µl sample had 1860 µl of PBS, 200 µl SDM, 500 µl of PHS and 600 cfu of added S. aureus, (for an effective concentration of about 234 CFU/mL) along with a variable amount of vancomycin. Each sample was incubated for 30 min at 37° C. Lycopene (1.125 mM), fucoxanthin (0.375 mM), additional vancomycin (so as to maintain the same concentration of vancomycin) and additional 3440 µl PBS (to bring the total volume to 6 ml) was added and the UV-Vis absorbance was measured. The chart on the bottom depicts the absorbance at 450 nm; with the break point representing the predicted MIC of 0.2 mg/ml. The chart on the top depicts the absorbance at 600 nm after 18 hour incubation at 37° C. The break point of 0.2 µg/ml represents the actual MIC.

This showed that lycopene/HSA complexes can be used to predict the antimicrobial susceptibility of the causative pathogen against an candidate antimicrobial. Other factors being constant, the signal scales with the number of viable pathogenic microorganisms in the sample. For a set of samples that have the same number of microorganisms, a 20 min incubation step with an increasing concentration of a candidate antimicrobial may result in a decreasing number of microorganisms when the antimicrobial concentration exceeds the minimum inhibitory concentration. Thus, a small incubation step can be combined with the lycopene/HSA complexes to characterize the MIC.

Starting from the initial blood draw, this test for MIC required a sample preparation time of about 3 hours (so that the pathogen concentration can be increased to >1000 CFU/mL; so that the sample could be aliquoted into multiple parts with nearly identical pathogen concentrations), an additional incubation time of 30 minutes and a testing time of less than 5 minutes. Thus, the antimicrobial susceptibility information could be developed well within 6 hours, and could be used to influence a $2^{nd}$ antimicrobial dose.

Example 14

The Molar Ratio of Lycopene to Albumin can Determine Single or Double Filling of Albumin Lycopene/albumin complexes were prepared in a similar way as Example 3, except the ratio of lycopene to albumin that were mixed was varied. When the molar ratio of lycopene to albumin was above 0.5, the UV-Vis absorption peaked at 565 nm, an overall red coloration of the solution was observed after acetone removal and filtering, and a strong background absorption at 600 nm then double filled albumin was observed. This indicated that the albumin was double filled. When the molar ratio was kept below 0.4, UV-Vis peaks at 565 nm were absent, an overall orange coloration was observed after acetone removal and filtering, and nearly no absorption at 600 nm only single filled albumin was observed. This indicated that the albumin was single filled.

Example 15

Breaking up Aggregates of Albumin by Sonication Under Raised pH

In some solutions of the hydrophobic ligand-albumin complexes, aggregation was detected (via an uptick in the absorbance at 600 nm) after a few days of storage at 5° C. This happens at faster rates as the number/amount of double filled albumin increased, and if the isomerization of lycopene (from the trans form to the cis form) is not carried out. In such cases, the nucleation/growth kinetics of aggregated albumin is facilitated. But when all the necessary steps to minimize double filled albumin are performed, and the cis form is used, storage at room temperature will eventually result in the formation of aggregated albumin.

For solutions that formed aggregates of hydrophobic ligand-albumin complexes during storage, the aggregates were broken up by raising the pH of the solutions to above 8.5 and sonicating for a short period (5 to 10 minutes), or incubating the complexes at 37° C. for 30 min to 60 min.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method for determining a minimum inhibitory concentration (MIC) of an antimicrobial for a microorganism, the method comprising:
   a) contacting a plurality of compositions with the antimicrobial, wherein each composition of the plurality of compositions comprises a microorganism comprising a cell wall and wherein each composition is contacted with a different amount of the antimicrobial
   b) contacting each composition formed in step a) with an aqueous solution comprising a non-covalent complex of a hydrophobic molecule and a single albumin protein, wherein the hydrophobic molecule functionally associates with the microorganism;
   c) detecting one or more properties of the hydrophobic molecule in each composition formed in step b); and
   d) determining the minimum inhibitory concentration of the antimicrobial for the microorganism based on the detecting.

2. The method of claim 1, wherein the microorganism is a pathogenic microorganism.

3. The method of claim 1, wherein the hydrophobic molecule is a carotenoid.

4. The method of claim 3, wherein the carotenoid is a carotene.

5. The method of claim 4, wherein the carotene is lycopene or β-carotene.

6. The method of claim 1, wherein the antimicrobial is an antibacterial.

7. The method of claim 1, wherein the antimicrobial is an antifungal.

8. The method of claim 1, wherein the albumin protein is a human serum albumin protein.

9. The method of claim 1, wherein the method further comprises forming the aqueous solution comprising the non-covalent complex of hydrophobic molecule and single albumin protein by:

dissolving the hydrophobic molecule in:

i) a first organic solvent comprising a $C_3$-$C_5$ ketone; or ii) a combination of the first organic solvent and a second organic solvent in a ratio of from about 0.001:1 to about 1000:1 v/v, to provide a first solution;

combining the first solution with a second solution to provide a third solution, wherein the second solution is an aqueous solution comprising an albumin protein; and removing the first organic solvent or the combination of the first organic solvent and the second organic solvent from the third solution to provide a fourth solution, wherein the fourth solution is an aqueous solution comprising a non-covalent complex of the hydrophobic molecule and a single albumin protein.

10. The method of claim 9, wherein the $C_3$-$C_5$ ketone is acetone.

11. The method of claim 9, wherein the hydrophobic molecule is dissolved in the combination of a first organic solvent and a second organic solvent, and wherein the ratio of the first organic solvent and the second organic solvent is in the range of about 1:1 to about 5:1.

12. The method of claim 11, wherein the hydrophobic molecule is dissolved in the combination, and wherein the combination comprises the first organic solvent and the second organic solvent in a ratio of about 2:1.

13. The method of claim 9, wherein the hydrophobic molecule is dissolved in the combination, and wherein the method comprises:

dissolving the hydrophobic molecule in the second organic solvent, to provide a fifth solution; and combining the fifth solution with the $C_3$-$C_5$ ketone to provide the first solution prior to combining the first solution with the second solution.

14. The method of claim 9, wherein the removing is performed by evaporation.

* * * * *